(12) United States Patent
Jones et al.

(10) Patent No.: US 7,691,877 B2
(45) Date of Patent: Apr. 6, 2010

(54) PHARMACEUTICALS

(75) Inventors: Peter Jones, Sandwich (GB); David Pryde, Sandwich (GB); Thien Duc Tran, Sandwich (GB)

(73) Assignee: Pfizer Inc., New York, NY (US)

( * ) Notice: Subject to any disclaimer, the term of this patent is extended or adjusted under 35 U.S.C. 154(b) by 157 days.

(21) Appl. No.: 11/675,667

(22) Filed: Feb. 16, 2007

(65) Prior Publication Data

US 2007/0197478 A1   Aug. 23, 2007

Related U.S. Application Data

(60) Provisional application No. 60/774,580, filed on Feb. 17, 2006, provisional application No. 60/829,730, filed on Oct. 17, 2006, provisional application No. 60/870,020, filed on Dec. 14, 2006.

(51) Int. Cl.
   *C07D 513/02*   (2006.01)
   *C07D 515/02*   (2006.01)
   *A01N 43/42*    (2006.01)
   *A61K 31/44*    (2006.01)

(52) U.S. Cl. ...................................... 514/303; 546/118

(58) Field of Classification Search ................. 546/118; 514/303
   See application file for complete search history.

(56) References Cited

FOREIGN PATENT DOCUMENTS

| | | |
|---|---|---|
| EP | 1104764 | 6/2001 |
| JP | 11193282 | 7/1999 |
| WO | 9907703 | 2/1999 |
| WO | 0043394 | 7/2000 |
| WO | 0075145 | 12/2000 |
| WO | 2004029054 | 4/2004 |
| WO | 2004043913 | 5/2004 |
| WO | 2005002520 | 1/2005 |
| WO | 2005025583 | 3/2005 |
| WO | 2005051317 | 6/2005 |
| WO | 2005118555 | 12/2005 |
| WO | 2006015263 | 2/2006 |
| WO | 2006030031 | 3/2006 |
| WO | 2007028129 | 3/2007 |

OTHER PUBLICATIONS

Barrat et al., The Journal of experimental medicine, (Oct. 17, 2005), vol. 202, No. 8, pp. 1131-1139.*
Yutilov et al., Khimiya Geterotsiklicheskikh Soedinenii (1986), (1), 97-102.*
Hemmi, et al., "Small Anti-viral compounds activate immune cells via the TLR7 MyD88-dependent signaling pathway", Nature Publishing Group, vol. 3, No. 2, 2002, pp. 196-200.
Isobe, Y., et al. "Synthesis and Structure-Activity Relationships of 2-substituted-8-hydroxyadenine Derivatives as Orally Available Interferon Inducers without Emetic Side Effects", Bioorganic & Medinical Chemistry, vol. 11, No. 17, 2003, pp. 3641-3647.
Serbina, L., et al., Ukrainskii Khimicheskii Zhurnal, Russian, 2002, 68 (3-4) 114-118, (CAS Accession No. 2002:426855, Chemical Abstract 137:247644).
Yutilov, Y., et al., Khimiya, Geterotsiklicheskikh Soedinenii, 1986(1) 97-102, (CAS Accession No. 1987:32918, Chemical Abstract 106:32918).

* cited by examiner

*Primary Examiner*—D. Margaret Seaman
*Assistant Examiner*—Niloofar Rahmani
(74) *Attorney, Agent, or Firm*—Gregg C. Benson; J. Michael Dixon

(57) ABSTRACT

The present invention relates to immune response modifiers of formula (I), which act selectively through agonism, of Toll-Like Receptors (TLRs), uses thereof, processes for the preparation thereof, intermediates used in the preparation thereof and compositions containing said inhibitors. These inhibitors have utility in a variety of therapeutic areas including the treatment of infectious disease such as Hepatitis (e.g. HCV, HBV), genetically related viral infection and cancer.

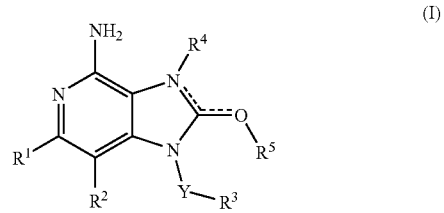

(I)

22 Claims, No Drawings

PHARMACEUTICALS

This application claims the benefit of U.S. Provisional Application No. 60/774,580, filed Feb. 17, 2006, U.S. Provisional Application No. 60/829,730, filed Oct. 17, 2006, and U.S. Provisional Application No. 60/870,020, filed Dec. 14, 2006, all of which are herein incorporated by reference in their entirety.

The invention relates to 3-deazapurine derivatives. The invention further relates to processes for the preparation of, intermediates used in the preparation of, pharmaceutical compositions containing, and uses of such 3-deazapurine derivatives.

Toll-Like Receptors (TLR) are primary transmembrane proteins characterized by an extracellular leucine-rich domain and a cytoplasmic tail that contains a conserved region named the Toll/IL-1 receptor (TIR) domain. They are expressed predominantly on immune cells (for example dendritic cells, T lymphocytes, macrophages, monocytes and natural killer cells), which serve as a key part of the innate immune system. They are a group of pattern recognition receptors which bind to pathogen-associated molecular patterns [for reviews, see for example, Ulevitch, R. J., Nature Reviews: Immunology, 4, 512-520, 2004 and Akira, S., Takeda, K., and Kaisho, T., Annual Rev. Immunol., 21, 335-376, 2003]. Their name derives from sequence homology to the Drosophila melanogaster gene Toll, which was found in fruit flies to play a key role in protecting the fly from fungal infections [Hoffmann, J. A., Nature, 426, 33-38, 2003]. There are 11 TLRs which have been identified in mammalian systems, and other non-mammalian TLRs have been found in other vertebrates. All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-, interleukins, MIP-1 and MCP-1 which contribute to the killing and clearance of the pathogenic invasion.

Accordingly, there is an ongoing need to provide TLR7 modulators, in particular agonists. Preferably, such compounds should have one or more of the following properties: they should bind selectively to the TLR7 receptor, be well absorbed from the gastrointestinal tract, be metabolically stable and possess favourable pharmacokinetic properties, demonstrate few side effects and be easily formulated.

We have now found a series of 3-deazapurine derivatives which are modulators, in particular agonists, of the TLR7 receptor and have utility in a variety of therapeutic areas in which modulation, in particular agonism, of the TLR7 receptor is implicated, including the treatment of viral infections (such as HCV or HBV), cancers and tumours, and T2 Helper cell (TH2) mediated diseases.

According to a first aspect of the invention, there is provided a compound of formula (I)

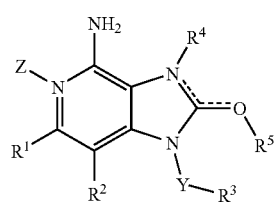

(I)

or a pharmaceutically acceptable salt or solvate of said compound, wherein (a) Y is a direct bond, and $R^3$ is selected from aryl, $(C_1\text{-}C_6)$ alkyl and —$(C_1\text{-}C_4)$alkylene-O—$(C_1\text{-}C_4)$alkyl; or (b) Y is $(C_{1-4})$alkylene, and $R^3$ is selected from aryl, $(C_3\text{-}C_7)$ cycloalkyl and a 3 to 10-membered heterocyclyl;

Z is an oxygen or is absent;

$R^1$ is selected from H, halo, OH, CN, $(C_1\text{-}C_6)$alkyl, $(C_3\text{-}C_7)$ cycloalkyl, $(C_1\text{-}C_6)$alkoxy, —$NHSO_2R^6$, —$NR^6R^7$, —$C(O)R^6$, —$CO_2R^6$, —$C(O)NR^6R^7$, —$C(O)NR^6SO_2R^8$, aryl and 3 to 10-membered heterocyclyl;

$R^2$ is selected from H, halo, OH, $(C_1\text{-}C_6)$alkyl, $(C_3\text{-}C_7)$cycloalkyl, $(C_1\text{-}C_6)$alkoxy, —$NR^6R^7$, —$CO_2R^6$, —$C(O)NR^6R^7$, —$C(O)NR^6SO_2R^8$, and 3 to 10-membered heterocyclyl; or $R^1$ and $R^2$ may be joined to form a $(C_2\text{-}C_5)$alkylene link, said link optionally incorporating 1 or 2 heteroatoms each independently selected from N, O and S;

$R^5$ is absent and $R^4$ is selected from H, $(C_3\text{-}C_7)$cycloalkyl, aryl, —$(CH_2)$aryl, —$C(O)R^9$, —$CO_2R^9$, —$(C_1\text{-}C_6)$alkylene-O—$C(O)R^9$, —$(C_1\text{-}C_6)$alkylene-O—$CO_2R^9$), —$C(O)NR^9R^{10}$, —$(C_1\text{-}C_6)$alkylene-O—$C(O)NR^9R^{10}$ and —$(C_1\text{-}C_6)$alkylene-O—$P(O)(OH)_2$; or $R^4$ is absent and $R^5$ is selected from $R^9$, —$C(O)R^9$, —$CO_2R^9$, —$(C_1\text{-}C_6)$alkylene-O—$C(O)R^9$, —$(C_1\text{-}C_6)$alkylene-O—$CO_2R^9$, —$C(O)NR^9R^{10}$, —$(C_1\text{-}C_6)$alkylene-O—$C(O)NR^9R^{10}$ and —$(C_1\text{-}C_6)$alkylene-O—$P(O)(OH)_2$;

$R^6$ and $R^7$ are each independently selected from H, $(C_1\text{-}C_6)$ alkyl, $(C_3\text{-}C_7)$cycloalkyl, and —$(C_1\text{-}C_6)$alkylene$(C_3\text{-}C_7)$ cycloalkyl; or $R^6$ and $R^7$ taken together with the nitrogen to which they are attached form a 3 to 6 membered saturated heterocycle optionally containing a further one or two heteroatoms selected from N, O and S;

$R^8$ is selected from $(C_1\text{-}C_6)$alkyl, $(C_3\text{-}C_7)$cycloalkyl and phenyl;

$R^9$ and $R^{10}$ are each independently selected from H, $(C_1\text{-}C_6)$ alkyl, $(C_3\text{-}C_7)$cycloalkyl, aryl, —$(CH_2)$aryl and 3 to 10-membered heterocyclyl; or $R^9$ and $R^{10}$, taken together with the nitrogen to which they are attached, form a 3 to 10-membered heterocyclyl group;

$R^{11}$ and $R^{12}$ are independently selected from H and $(C_1\text{-}C_6)$ alkyl; or $R^{11}$ and $R^{12}$ together with the N to which they are attached form a 3 to 6 membered saturated heterocyclyl optionally containing a further one or two heteroatoms selected from N, O and S;

said alkyl, cycloalkyl, alkoxy, aryl and heterocyclyl groups being optionally substituted by one or more atoms or groups independently selected from halo, OH, oxo, $CF_3$, CN, $(C_1\text{-}C_6)$alkyl, $(C_3\text{-}C_7)$cycloalkyl, $(C_1\text{-}C_6)$alkoxy, —$(C_1\text{-}C_6)$alkylene-O—$(C_1\text{-}C_6)$alkyl, —$(C_1\text{-}C_6)$alkylene-OH, —$NR^{11}R^{12}$, —$(C_1\text{-}C_6)$alkylene-$NR^{11}R^{12}$, aryl and 3 to 10-membered heterocyclyl;

with the proviso that when $R^1$ and $R^2$ are H, and Z and $R^5$ are absent, then (a) $R^4$ is not methyl when Y—$R^3$ is ethyl; and (b) $R^4$ is not H or methyl when Y—$R^3$ is methyl.

Unless otherwise indicated, alkyl and alkoxy groups may be straight or branched and contain 1 to 6 carbon atoms and preferably 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Cycloalkyl includes cyclopropyl, cyclobutyl, cyclopentyl, cyclohexyl, cycloheptyl and bicycloheptanes.

Halo means fluoro, chloro, bromo or iodo and is preferably fluoro or chloro.

Aryl includes phenyl, naphthyl, anthracenyl and phenanthrenyl and is preferably phenyl.

Unless otherwise stated, a heterocycle may be saturated, partially saturated or aromatic and contain one or more heteroatoms independently selected from N, O and S. For example, the heterocyle may be a 5 to 6 membered saturated, partially saturated or aromatic heterocycle. Examples of saturated heterocyclic groups are tetrahydrofuranyl, pyrrolidinyl, pyrrolinyl, imidazolidinyl, imidazolinyl, dioxolanyl, dihydropyranyl, tetrahydropyranyl, piperidinyl, pyrazolinyl, dioxanyl, morpholinyl, dithianyl, thiomorpholinyl, piperazinyl, azepinyl, oxazepinyl and thiazepinyl. Examples of aromatic monoheterocyclic groups are pyrrolyl, furanyl, thiophenyl, pyrazolyl, imidazolyl, isoxazolyl, oxazolyl, isothiazolyl, thiazolyl, triazoles (such as 1,2,3 triazolyl and 1,2,4-triazolyl), oxadiazoles (such as 1-oxa-2,3-diazolyl, 1-oxa-2,4-diazolyl, 1-oxa-2,5-diazolyl and 1-oxa-3,4-diazolyl), thiadiazoles (such as 1-thia-2,3-diazolyl, 1-thia-2,4-diazolyl, 1-thia-2,5-diazolyl and 1-thia-3,4-diazolyl), tetrazolyl, pyridinyl, pyridazinyl, pyrimidinyl, pyrazinyl and triazinyl. Examples of bicyclic aromatic heterocyclic groups are benzofuranyl, benzothiophenyl, indolyl, benzimidazolyl, indazolyl, benzotriazolyl, quinolinyl and isoquinolinyl.

In the case where a plurality of substituents may be selected from a number of alternative groups, the selected groups may be the same or different.

In one embodiment, Z is oxygen such that N-oxides are formed.

In a further embodiment of the invention, Z is absent.

In a yet further embodiment of the invention $R^1$ is selected from
(a) H;
(b) CN;
(c) halo
(d) $(C_1-C_6)$alkyl optionally substituted by one to three halo atoms;
(e) tetrahydrofuranoxy;
(f) $(C_1-C_6)$alkyl substituted by a 3 to 6 membered saturated heterocycyl containing 1 to 3 hetero atoms independently selected from N, O and S wherein said heterocyclyl is optionally substituted by one to three groups independently selected from $CF_3$, $(C_1-C_6)$alkyl, $(C_1-C_6)$alkoxy and —$(C_1-C_6)$alkylene-O—$(C_1-C_6)$alkyl;
(g) —$(C_1-C_4)$alkylene-O—$(C_1-C_6)$alkyl;
(h) —$(C_1-C_4)$alkylene-N(H)—$(C_1-C_4)$alkylene-O—$(C_1-C_4)$alkyl;
(i) $(C_1-C_6)$alkoxy optionally substituted by OH or cyclopropyl;
(j) $(C_3-C_7)$cycloalkyl;
(k) —$(C_1-C_4)$alkylene$(C_3-C_7)$cycloalkyl;
(l) —$C(O)NR^6R^7$;
(m) —$CO_2R^6$;
(n) —$C(O) R^6$;
(o) a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; or a 6-membered aromatic heterocyclyl comprising 1 to 3 nitrogen atoms, said 5 and 6 membered aromatic heterocyclyl being optionally substituted by one to three atoms or groups independently selected from halo, OH, $CF_3$, $(C_1-C_6)$alkyl, $(C_1-C_6)$alkoxy, —$(C_1-C_6)$alkylene-O—$(C_1-C_6)$alkyl, —$(C_1-C_6)$alkylene-OH , —$NR^{11}R^{12}$ and —$(C_1-C_6)$alkylene-$NR^{11}R^{12}$;
(p) phenyl optionally substituted by 1 to 3 halo atoms;
(q) —$NR^6R^7$;
(r) —NH—$(C_1-C_4)$alkylene-O—$(C_1-C_6)$alkyl;
(s) or $R^1$ and $R^2$ may be joined to form a $(C_2-C_5)$alkylene link;

wherein
$R^6$, $R^7$, $R^{11}$ and $R^{12}$ are as defined in the first aspect of the invention.

In a further embodiment, $R^1$ is selected from
(a) H;
(b) CN;
(c) halo
(d) $(C_1-C_6)$alkyl optionally substituted by one to three halo atoms;
(e) tetrahydrofuranoxy;
(f) $(C_1-C_6)$alkyl substituted by morpholine, piperazine or pyrrolodine which are optionally substituted by one or two methyl groups;
(h) —$(C_1-C_4)$alkylene-N(H)—$(C_1-C_4)$alkylene-O—$(C_1-C_4)$alkyl;
(i) $(C_1-C_6)$alkoxy optionally substituted by OH or cyclopropyl;
(j) $(C_3-C_7)$cycloalkyl;
(k) —$(C_1-C_4)$alkylene$(C_3-C_7)$cycloalkyl;
(l) —$C(O)NR^6R^7$;
(m) —$CO_2R^6$;
(n) —$C(O) R^6$;
(o) a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; or a 6-membered aromatic heterocyclyl comprising 1 to 3 nitrogen atoms, said 5 and 6 membered aromatic heterocyclyl being optionally substituted by one to three atoms or groups independently selected from halo, OH, $CF_3$, $(C_1-C_6)$alkyl, $(C_1-C_6)$alkoxy, —$(C_1-C_6)$alkylene-O—$(C_1-C_6)$alkyl, —$(C_1-C_6)$alkylene-OH , —$NR^{11}R^{12}$ and —$(C_1-C_6)$alkylene-$NR^{11}R^{12}$;
(p) phenyl optionally substituted by 1 to 3 halo atoms;
(q) —$NR^6R^7$;
(r) —NH—$(C_1-C_4)$alkylene-O—$(C_1-C_6)$alkyl;

wherein
$R^6$, $R^7$, $R^{11}$ and $R^{12}$ are as defined in the first aspect of the invention.

In a yet further embodiment, $R^1$ is selected from $(C_1-C_4)$alkyl optionally substituted by one to three halo atoms; $(C_3-C_7)$cycloalkyl; or a 5 to 6 membered aromatic heterocyclyl optionally substituted by one to three atoms or groups independently selected from halo, OH, $CF_3$, $(C_1-C_6)$alkyl, $(C_1-C_6)$alkoxy, —$(C_1-C_6)$alkylene-O—$(C_1-C_6)$alkyl and —NH$(C_1-C_6)$alkyl.

In a yet further embodiment, $R^1$ is selected from methyl or ethyl substituted by one to three fluoro atoms; cyclopropyl; —$(C_1-C_2)$alkylene-O—$(C_1-C_2)$alkyl; $(C_1-C_4)$alkoxy optionally substituted by OH or cyclopropyl; —$COCH_3$; —$CH_2OCH_3$; and —$CO_2CH_3$.

In a yet further embodiment, $R^1$ is cyclopropyl or $CF_3$.

In a yet further embodiment, $R^1$ is a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom, said 5 membered aromatic heterocyclyl being optionally substituted by one to three atoms or groups independently selected from halo, OH, $CF_3$, $(C_1-C_6)$alkyl, $(C_1-C_6)$alkoxy, —$(C_1-C_3)$alkylene-O—$(C_1-C_4)$alkyl, —$(C_1-C_4)$alkylene-OH, —$NR^{11}R^{12}$ and —$(C_1-C_3)$alkylene-$NR^{11}R^{12}$, wherein $R^{11}$ and $R^{12}$ are as defined in claim in the first aspect of the invention.

In a yet further embodiment, $R^1$ is selected from imadazolyl, oxazolyl, oxadiazolyl, triazole, pyrazole and thiazole, all of which are optionally substituted by one to three atoms or groups independently selected from halo, OH, $CF_3$, $(C_1-C_6)$alkyl, $(C_1-C_6)$alkoxy, —$(C_1-C_3)$alkylene-O—$(C_1-C_4)$alkyl, —$(C_1-C_4)$alkylene-OH and —$(C_1-C_3)$alkylene-$NR^{11}R^{12}$, wherein $R^{11}$ and $R^{12}$ are as defined in the first aspect of the invention.

In a yet further embodiment, $R^1$ is selected from unsubstituted oxazolyl, triazole, pyrazole and thiazole.

In a yet further embodiment, $R^1$ is oxazolyl.

In a yet further embodiment, $R^2$ is selected from
(a) H;
(b) halo
(c) $(C_1-C_6)$alkyl optionally substituted by one to three halo atoms;
(d) tetrahydrofuranoxy;
(e) $(C_1-C_6)$alkyl substituted by a 3 to 6 membered saturated heterocycyl containing 1 to 3 hetero atoms independently selected from N, O and S wherein said heterocyclyl is optionally substituted by one to three groups independently selected from $CF_3$, $(C_1-C_6)$alkyl, $(C_1-C_6)$alkoxy and —$(C_1-C_6)$alkylene-O—$(C_1-C_6)$alkyl;
(f) —$(C_1-C_4)$alkylene-O—$(C_1-C_6)$alkyl;
(g) —$(C_1-C_4)$alkylene-N(H)—$(C_1-C_4)$alkylene-O—$(C_1-C_4)$alkyl;
(h) $(C_1-C_6)$alkoxy optionally substituted by OH or cyclopropyl;
(i) $(C_3-C_7)$cycloalkyl;
(j) —$(C_1-C_4)$alkylene$(C_3-C_7)$cycloalkyl;
(k) —$C(O)NR^6R^7$;
(l) —$CO_2R^6$;
(m) —$C(O)R^6$;
(n) a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; or a 6-membered aromatic heterocyclyl comprising 1 to 3 nitrogen atoms, said 5 and 6 membered aromatic heterocyclyl being optionally substituted by one to three atoms or groups independently selected from halo, OH, $CF_3$, $(C_1-C_6)$alkyl, $(C_1-C_6)$alkoxy, —$(C_1-C_6)$alkylene-O—$(C_1-C_6)$alkyl, —$(C_1-C_6)$alkylene-OH, —$NR^{11}R^{12}$ and —$(C_1-C_6)$alkylene-$NR^{11}R^{12}$;
(o) phenyl optionally substituted by 1 to 3 halo atoms;
(p) —$NR^6R^7$;
(q) —NH—$(C_1-C_4)$alkylene-O—$(C_1-C_6)$alkyl;

wherein $R^6$, $R^7$, $R^{11}$ and $R^{12}$ are as defined in the first aspect of the invention.

In a yet further embodiment, $R^2$ is H or methyl.

In a yet further embodiment, $R^2$ is H.

In a yet further embodiment, Y is methylene; and $R^3$ is aryl, or a 5 to 6 membered heterocyclyl containing one to three heteroatoms independently selected from N, O and S, said aryl and heterocyclyl being optionally substituted by one to three atoms or groups independently selected from halo, OH, oxo, $CF_3$, CN, $(C_1-C_6)$alkyl, $(C_3-C_7)$cycloalkyl, $(C_1-C_6)$alkoxy, —$(C_1-C_6)$alkylene-O—$(C_1-C_6)$alkyl, —NH$(C_1-C_6)$alkyl, —N($(C_1-C_6)$alkyl)$_2$, aryl and 3 to 10-membered heterocyclyl.

In a yet further embodiment, Y is methylene; and $R^3$ is selected from aryl; a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; and a 6-membered aromatic heterocyclyl comprising 1 to 3 nitrogen atoms; said aryl and aromatic heterocycle being optionally substituted by one to three atoms or groups independently selected from halo, OH, oxo, $CF_3$, CN, $(C_1-C_6)$alkyl, $(C_3-C_7)$cycloalkyl, $(C_1-C_6)$alkoxy, —$(C_1-C_6)$alkylene-O—$(C_1-C_6)$alkyl, —$(C_1-C_6)$alkylene-OH, —$NR^{11}R^{12}$, —$(C_1-C_6)$alkylene-$NR^{11}R^{12}$, aryl and 3 to 10-membered heterocyclyl, wherein $R^{11}$ and $R^{12}$ are as defined in the first aspect of the invention.

In a yet further embodiment, Y is methylene; and $R^3$ is selected from phenyl, pyridyl, pyrimidyl, pyridizinyl and pyrazinyl each of which are optionally substituted by one to three atoms or groups independently selected from halo, $(C_{1-4})$alkyl, $(C_1-C_4)$alkoxy and $CF_3$.

In a yet further embodiment, Y is methylene; and $R^3$ is selected from phenyl, pyridin-3-yl and 6-methyl-pyridin-3-yl.

In a yet further embodiment,

Y is methylene;

$R^1$ is selected from $(C_1-C_4)$alkyl substituted by one to three halo atoms; $(C_3-C_7)$cycloalkyl; and a 5 to 6 membered aromatic heterocyclyl optionally substituted by one to three groups independently selected from halo, OH, $CF_3$, $(C_1-C_6)$alkyl, $(C_1-C_6)$alkoxy, —$(C_1-C_6)$alkylene-O—$(C_1-C_6)$alkyl and —NH$(C_1-C_6)$alkyl;

$R^2$ is H;

$R^3$ is phenyl or 3-pyridyl each of which are optionally substituted by one to three atoms or groups independently selected from halo, $(C_{1-4})$alkyl and $CF_3$;

$R^4$ is H; and $R^5$ is absent.

In a yet further embodiment,

Y is methylene;

$R^1$ is selected from $CF_3$; cyclopropyl; and oxazole;

$R^2$ is H;

$R^3$ is selected from phenyl, pyridin-3-yl and 6-methyl-pyridin-3-yl.

$R^4$ is H; and $R^5$ is absent.

In a yet further embodiment, $R^5$ is absent; and $R^4$ is selected from —$(C_1-C_6)$alkylene-O—$C(O)R^9$, —$(C_1-C_6)$alkylene-O—$CO_2R^9$, —$(C_1-C_6)$alkylene-O—C(O)$NR^9R_{10}$ and —$(C_1-C_6)$alkylene-O—P(O)(OH)$_2$, wherein Y, Z, $R^1$, $R^2$ $R^3$ $R^9$ and $R^{10}$ are as defined in the first aspect of the invention, to give a compound of formula (Ia):

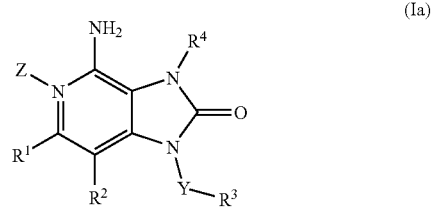

In a yet further embodiment, $R^4$ is H and $R^5$ is absent.

In a yet further embodiment, $R^4$ is absent; and $R^5$ is selected from —$(C_1-C_6)$alkylene-O—$C(O)R^9$, —$(C_1-C_6)$alkylene-O—$CO_2R^9$), —$(C_1-C_6)$alkylene-O—C(O)$NR^9R^{10}$ and —$(C_1-C_6)$alkylene-O—P(O)(OH)$_2$, wherein Y, $R^1$, $R^2$, $R^3$, $R^9$ and $R^{10}$ are as defined hereinbefore, to give a compound of formula (Ib):

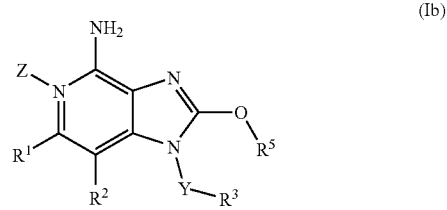

The examples of the invention form a yet further embodiment of the invention.

Preferred compounds of the invention are those of examples 1-4, 12, 15-18, 26, 27, 36-38, 4054, 60, 70, 76, 78, 82, 83, 86, 92-94, 96-98 and 100-102 and tautomers thereof and pharmaceutically acceptable salts or solvates of said compound or tautomer.

Yet further preferred compounds are selected from:
4-Amino-1-benzyl-6-cyclopropyl-1,3-dihydro-imidazo[4,5-c]pyridin-2-one (example 1);
4-Amino-1-benzyl-6-oxazol-2-yl-1,3-dihydro-imidazo[4,5-c]pyridin-2-one (Example 12);
4-Amino-1-benzyl-6-trifluoromethyl-1,3-dihydro-imidazo[4,5-c]pyridine-2-one (Example 15);

and tautomers thereof and pharmaceutically acceptable salts or solvates of said compound or tautomer.

In a further embodiment of the invention, there is provided a compound of formula (Ic)

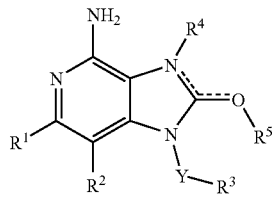

(Ic)

wherein
Y is methylene;
$R^1$ and $R^2$ are each independently selected from H, halo, OH, $(C_1-C_6)$alkyl, $(C_3-C_7)$cycloalkyl, $(C_1-C_6)$alkoxy, —$NR^6R^7$, —$CO_2R^6$, —$C(O)NR^6R^7$, —$C(O)NR^6SO_2R^8$, aryl and 3 to 10-membered heterocyclyl; or
$R^1$ and $R^2$ may be joined to form a $(C_2-C_5)$alkylene link, said link optionally incorporating 1 or 2 heteroatoms each independently selected from N, O and S;
$R^3$ is selected from $(C_1-C_6)$alkyl, $(C_3-C_7)$cycloalkyl, aryl and 3 to 10-membered heterocyclyl;
$R^4$ is selected from $R^9$, —$C(O)R^9$, —$CO_2R^9$ and —$C(O)NR^9R^{10}$, and $R^5$ is absent; or
$R^5$ is selected from $R^9$, —$C(O)R^9$, —$CO_2R^9$ and —$C(O)NR^9R^{10}$, and $R^4$ is absent;
$R^6$ and $R^7$ are each independently selected from H and $(C_1-C_6)$alkyl;
$R^8$ is selected from $(C_1-C_6)$alkyl, $(C_3-C_7)$cycloalkyl and phenyl;
$R^9$ and $R^{10}$ are each independently selected from H, $(C_1-C_6)$alkyl, $(C_3-C_7)$cycloalkyl, aryl, —$(CH_2)$aryl and 3 to 10-membered heterocyclyl; or
$R^9$ and $R^{10}$, taken together with the nitrogen to which they are attached, form a 3 to 10-membered heterocyclyl group;

said alkyl, cycloalkyl, alkoxy, aryl and heterocyclyl groups being optionally substituted by one or more groups independently selected from halo, OH, oxo, $CF_3$, CN, $(C_1-C_6)$alkyl, $(C_3-C_7)$cycloalkyl, $(C_1-C_6)$alkoxy, $(C_1-C_6)$alkoxy$(C_1-C_6)$alkyl, $NH(C_1-C_6)$alkyl, $N((C_1-C_6)$alkyl$)_2$, aryl and 3 to 10-membered heterocyclyl;

or a pharmaceutically acceptable salt or solvate of said compound;
with the proviso that when $R^1$ and $R^2$ are H, and Z and R5 are absent, then
(a) $R^4$ is not methyl when Y—$R^3$ is ethyl; or
(b) $R^4$ is not H or methyl when Y—$R^3$ is methyl.

A yet further embodiment of the invention, comprises compounds of formula (Ic) wherein $R^4$ is selected from $R^9$, —$C(O)R^9$, —$CO_2R^9$ and —$C(O)NR^9R^{10}$; $R^5$ is absent; and Y, $R^1$, $R^2$, $R^3$, $R^9$ and $R^{10}$ are as defined in the second aspect of the invention, to give the compound of formula (Ia) as shown hereinbefore.

A yet further embodiment of the invention, comprises compounds of formula (Ic) wherein
Y is methylene;
$R^1$ and $R^2$ are each independently selected from H, $(C_1-C_6)$alkyl, $(C_3-C_7)$cycloalkyl, —$CO_2H$, —$CO_2(C_1-C_6)$alkyl and —$C(O)NH(C_1-C_6)$alkylene$(C_3-C_7)$cycloalkyl; or $R^1$ and $R^2$ may be joined to form a $(C_2-C_5)$alkylene link;
$R^3$ is phenyl, which is optionally substituted by one or more groups independently selected from halo, OH, $CF_3$, CN, $(C_1-C_6)$alkyl, $(C_3-C_7)$cycloalkyl, $(C_1-C_6)$alkoxy, $NH(C_1-C_6)$alkyl and $N((C_1-C_6)$alkyl$)_2$;
$R^5$ is absent; and
$R^4$ is H.

A yet further embodiment of the second aspect of the invention, comprises compounds of formula (Ic)
wherein
Y is methylene;
$R^1$ and $R^2$ are each independently selected from H, $(C_1-C_6)$alkyl, $(C_3-C_7)$cycloalkyl, —$CO_2H$, —$CO_2(C_1-C_6)$alkyl and —$C(O)NH(C_1-C_6)$alkylene$(C_3-C_7)$cycloalkyl; or $R^1$ and $R^2$ may be joined to form a $(C_2-C_5)$alkylene link;
$R^3$ is phenyl, which is optionally substitued by one or more groups independently selected from halo and $CF_3$;
$R^5$ is absent; and
$R^4$ is H.

A yet further embodiment of the second aspect of the invention, comprises compounds of formula (Ic) wherein $R^5$ is selected from $R^9$, —$C(O)R^9$, —$CO_2R^9$ and —$C(O)NR^9R^{10}$; $R^4$ is absent; and Y, $R^1$, $R^2$ and $R^3$ are as hereinbefore defined, to give the compound of formula (Ib) as shown hereinbefore.

A yet further embodiment of the second aspect of the invention, comprises compounds of formula (Ic) wherein $R^1$ and $R^2$ are each independently selected from H, $(C_1-C_6)$alkyl, $(C_3-C_7)$cycloalkyl, —$CO_2R^6$, —$C(O)NR^6R^7$ and —$C(O)NR^6SO_2R^8$; or $R^1$ and $R^2$ may be joined to form a $(C_2-C_5)$alkylene link, said link optionally incorporating 1 or 2 heteroatoms each independently selected from N, O and S.

A yet further embodiment of the second aspect of the invention, comprises compounds of formula (Ic) wherein $R^1$ and $R^2$ are each independently selected from H, $(C_1-C_6)$alkyl, $(C_3-C_7)$cycloalkyl, —$CO_2H$, —$CO_2(C_1-C_6)$alkyl and —$C(O)NH(C_1-C_6)$alkylene$(C_3-C_7)$cycloalkyl; or $R^1$ and $R^2$ may be joined to form a $(C_2-C_5)$alkylene link.

A yet further embodiment of the second aspect of the invention, comprises compounds of formula (Ic) wherein $R^1$ and $R^2$ are each independently selected from H, $(C_1-C_3)$alkyl, cyclopropyl, —$CO_2H$, —$CO_2CH_3$ and —$C(O)NH(CH_2)$cyclopropyl; or $R^1$ and $R^2$ may be joined to form a $C_5$-alkylene link.

A yet further embodiment of the second aspect of the invention, comprises compounds of formula (Ic) wherein, $R^1$ is selected from H, methyl, n-propyl, isopropyl, cyclopropyl, —$CO_2H$, —$CO_2CH_3$ and —$C(O)NH(CH_2)$cyclopropyl; and $R^2$ is selected from H and methyl; or $R^1$ and $R^2$ may be joined to form a $C_5$-alkylene link.

A yet further embodiment of the second aspect of the invention, comprises compounds of formula (Ic) wherein $R^3$ is aryl, which is optionally substitued by one or more groups independently selected from halo, OH, oxo, $CF_3$, CN, ($C_1$-$C_6$)alkyl, ($C_3$-$C_7$)cycloalkyl, ($C_1$-$C_6$)alkoxy, ($C_1$-$C_6$)alkoxy ($C_1$-$C_6$)alkyl, NH($C_1$-$C_6$)alkyl, N(($C_1$-$C_6$)alkyl)$_2$, aryl and 3 to 10-membered heterocyclyl.

A yet further embodiment of the second aspect of the invention, comprises compounds of formula (Ic) wherein $R^3$ is phenyl, which is optionally substituted by one or more groups independently selected from halo, OH, $CF_3$, CN, ($C_1$-$C_6$)alkyl, ($C_3$-$C_7$)cycloalkyl, ($C_1$-$C_6$)alkoxy, NH($C_1$-$C_6$) alkyl and N(($C_1$-$C_6$)alkyl)$_2$. Yet more preferably, $R^3$ is phenyl, which is optionally substituted by one or more groups independently selected from halo and $CF_3$.

A yet further embodiment of the second aspect of the invention, comprises compounds of formula (Ic) wherein $R^3$ is selected from 2-fluorophenyl, 3-fluorophenyl, 4-fluorophenyl and 3-trifluoromethylphenyl.

Unless otherwise indicated, reference to compounds of the invention includes compounds of formula (I), (Ia), (Ib) and (Ic).

It is to be understood that the invention covers all combinations of particular embodiments of the invention as described hereinabove, consistent with the definition of the compounds of formula (I).

In a third aspect of the invention, there is provided a process for preparing a compound of formula (Ic)

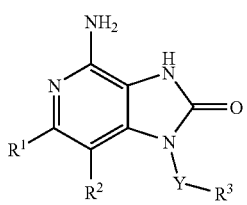
(Ic)

wherein in each of formulae Ia, XVIII, XVIIIa, XIX, XIXa, XXa, XXb, XIV, XV, LIV and LXIII, Y—$R^3$ is as defined in claim 14, $R^1$ is as defined in claim 2, $R^2$ is as defined in claim 10, $PG^1$ and $PG^2$ are nitrogen protecting agents and $R^{13}$ is ($C_{1-6}$)alkyl, said process comprising (a) Reaction of a compound of formula (XVIII) or (XVIIIa) with a carbonyl donating agent

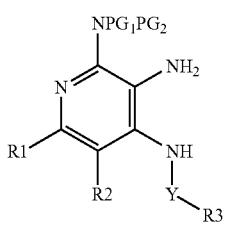
(XVIII)

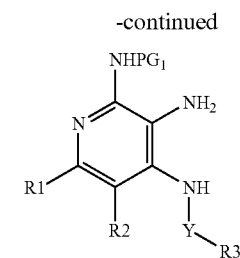
(XVIIIa)

to form a corresponding compound of formula (XIX) or (XIXa)

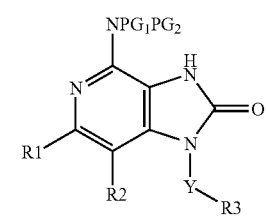
(XIX)

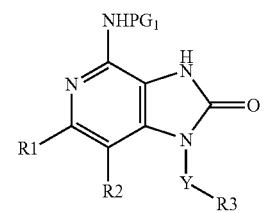
(XIXa)

then subsequent deprotection of the compound of formula (XIX) or (XIXa); or (b) reduction of a compound of formula (XXa)

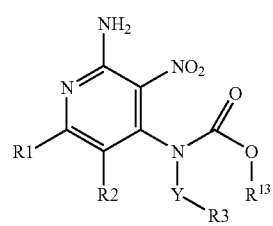
(XXa)

to form a compound of formula (XXb)

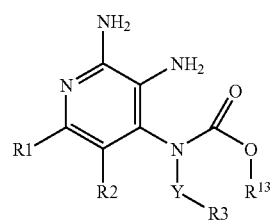
(XXb)

and then cyclisation of the compound of formula (XXb) by treatment with a protic acid; or (C) reduction of a compound of formula (XIV)

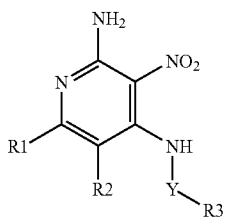

to form a compound of formula (XV)

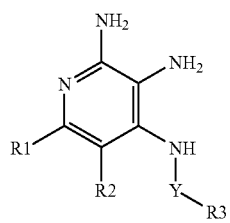

and then cyclisation of a compound of formula (XV) in the presence of a carbonyl moiety; or (e) cyclisation of a compound of formula (LIV) in the presence of diphenylphosphonyl azide to a corresponding compound of formula (XIXA) hereabove and then subsequent deprotection of the amino protection group

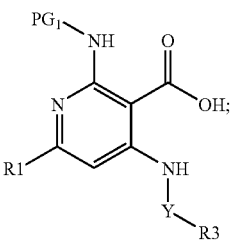

or
(f) hydrolysis of a compound of formula (LXIII)

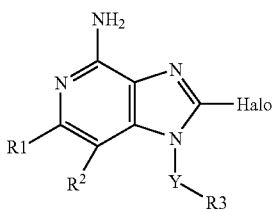

In a fourth aspect of the invention there is provided intermediates of formulae XVIII, XVIIIa, XIX, XIXa, XXa, XXb, XIV, XV, LIV and LXIII, wherein Y—$R^3$ is as defined in claim 14, $R^1$ is as defined in claim 2, $R^2$ is as defined in claim 10, $PG^1$ and $PG^2$ are nitrogen protecting agents and $R^3$ is $(C_{1-6})$alkyl.

Pharmaceutically acceptable salts of the compounds of formula (I) comprise the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

Hereinafter all references to compounds of formula (I) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include (i) where the compound of formula I contains a carboxylic acid functionality, an ester thereof, for example, a compound wherein the hydrogen of the carboxylic acid functionality of the compound of formula (I) is replaced by (C$_1$-C$_8$)alkyl; and (ii) where the compound of formula (I) contains a primary or secondary amino functionality, an amide thereof, for example, a compound wherein, as the case may be, one or both hydrogens of the amino functionality of the compound of formula (I) is/are replaced by (C$_1$-C$_{10}$)alkanoyl.

Further examples of replacement groups in accordance with the foregoing examples and examples of other prodrug types may be found in the aforementioned references. Moreover, certain compounds of formula (I) may themselves act as prodrugs of other compounds of formula (I).

Specifically, compounds of the present invention of formula (I) wherein R$^4$ is as herein defined, other than H, and R$^5$ is absent (i.e compounds of formula (Ia)), may be converted into compounds of formula (I) wherein R$^4$ is H and R$^5$ is absent via metabolic actions or solvolysis. Additionally, compounds of the present invention of formula (I) wherein R$^4$ is absent and R$^5$ is as herein defined, other than H (i.e compounds of formula (Ib)), may be converted into compounds of formula (I) wherein R$^4$ is absent and R$^5$ is H via metabolic actions or solvolysis.

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof (—CH$_3$→—CH$_2$OH):

(ii) where the compound of formula (I) contains an alkoxy group, an hydroxy derivative thereof (—OR→—OH);

(iii) where the compound of formula (I) contains a tertiary amino group, a secondary amino derivative thereof (—NR$^1$R$^2$→—NHR$^1$ or —NHR$^2$);

(iv) where the compound of formula (I) contains a secondary amino group, a primary derivative thereof (—NHR$^1$→—NH$_2$);

(v) where the compound of formula (I) contains a phenyl moiety, a phenol derivative thereof (-Ph>-PhOH);

(vi) where the compound of formula (I) contains an amide group, a carboxylic acid derivative thereof (—CONH$_2$→COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, a keto group, or so-called valence tautomerism in compounds which contain an aromatic moiety. It follows that a single compound may exhibit more than one type of isomerism.

For example and for explanation of the dotted line in formula (I), the compound of formula (Ia) wherein $R^4$ is H is the tautomer of the compound of formula (Ib) wherein $R^5$ is H:

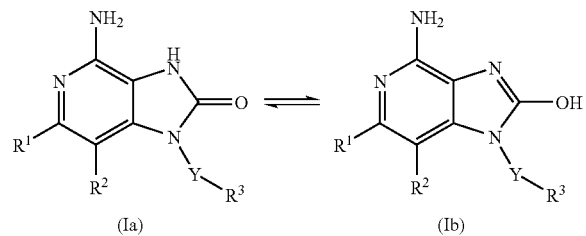

Included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, N.Y., 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of intermediate which provides the best combination of features for this purpose. Such features include the melting point, solubility, processability and yield of the intermediate form and the resulting ease with which the product may be purified on isolation.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, N.Y., 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999). Other means of topical administration include delivery by electroporation, iontophoresis, phonophoresis, sonophoresis and microneedle or needle-free (e.g. Powderject™, Bioject™, etc.) injection. Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

In order to improve dissolution properties, a solid amorphous spray-dried dispersion (SDD) of 4-Amino-1-benzyl-6-trifluoromethyl-1,3-dihydro-imidazo[4,5-c]pyridine-2-one (example 15 hereinafter) and hydroxypropyl methyl cellulose (HPMC E3 Prem LV, Methocel®, available from Dow Chemical Company, Midland, Mich.) was prepared as follows. First, a spray solution was formed containing 2.97 g water, 16.83 g methanol, and 250 µL 1 M KOH (containing 9.8 mg potassium cations), to which was added 51.27 mg of the crystalline neutral form of 4-Amino-1-benzyl-6-trifluoromethyl-1,3-dihydro-imidazo[4,5-c]pyridine-2-one. Next, 140.4 mg HPMC was added to the solution and the solution was stirred for 5 minutes and sonicated for 2 minutes. The solution was pumped via a Cole Parmer 74900 series rate-controlling syringe pump at a rate of 1.1 ml/min into a small-scale spray-drying apparatus consisting of an 11-cm diameter stainless steel chamber. The solution was atomized through a two-fluid nozzle (Spraying Systems Co., Wheaton, Ill., Model No. SU1A) using a heated stream of nitrogen at a flow rate of 1 standard ft$^3$/min. The heated gas entered the chamber at an inlet temperature of 85° C. and exited at an outlet temperature of 22° C. The resulting solid amorphous dispersion was collected on Whatman #1 microcellulose filter media (11 µm pore size, 11 cm outer diameter), dried under vacuum, and stored in a desiccator. The dispersion contained 25.4 wt % 4-Amino-1-benzyl-6-trifluoromethyl-1,3-dihydro-imidazo[4,5-c]pyridine-2-one, 4.9 wt % potassium cations, and 69.7 wt % HPMC. The yield was about 60%.

For the avoidance of doubt, references herein to "treatment" include references to curative, palliative and prophylactic treatment.

The following schemes illustrate general methods for the preparation of compounds of formula (I), and intermediates thereto.

It will be appreciated by those skilled in the art that certain of the procedures described in the schemes for the preparation of compounds of formula (I) or intermediates thereto may not be applicable to some of the possible substituents.

It will be further appreciated by those skilled in the art that it may be necessary or desirable to carry out the transformations described in the schemes in a different order from that described, or to modify one or more of the transformations, to provide the desired compound of formula (I).

It will be still further appreciated by those skilled in the art that, as illustrated in the schemes that follow, it may be necessary or desirable at any stage in the synthesis of compounds of formula (I) to protect one or more sensitive groups in the molecule so as to prevent undesirable side reactions. In particular, it may be necessary or desirable to protect amino groups. The protecting groups used in the preparation of compounds of formula (I) may be used in conventional manner. See, for example, those described in 'Protective Groups in Organic Synthesis' by Theodora W Green and Peter G M Wuts, third edition, (John Wiley and Sons, 1999), in particular chapter 7, pages 494-653 ("Protection for the Amino Group"), incorporated herein by reference, which also describes methods for the removal of such groups.

The amino protecting groups boc, benzyloxycarbonyl, benzyl and acetyl are of particular use in the preparation of compounds of formula (I) and intermediates thereto.

Unless otherwise indicated, $R^1$ to $R^7$ and Y in the schemes are as defined herein. $PG^1$ and $PG^2$ are nitrogen protecting groups.

The compounds of formula (I) may be prepared as depicted in Scheme 1, and preparations 1 to 27 hereinafter further illustrate scheme 1.

It will be appreciated that the amino protected group $N(PG1)(PG^2)$ in formulae (XVII) to (XIX) is some instances may be $N(H)PG^1$.

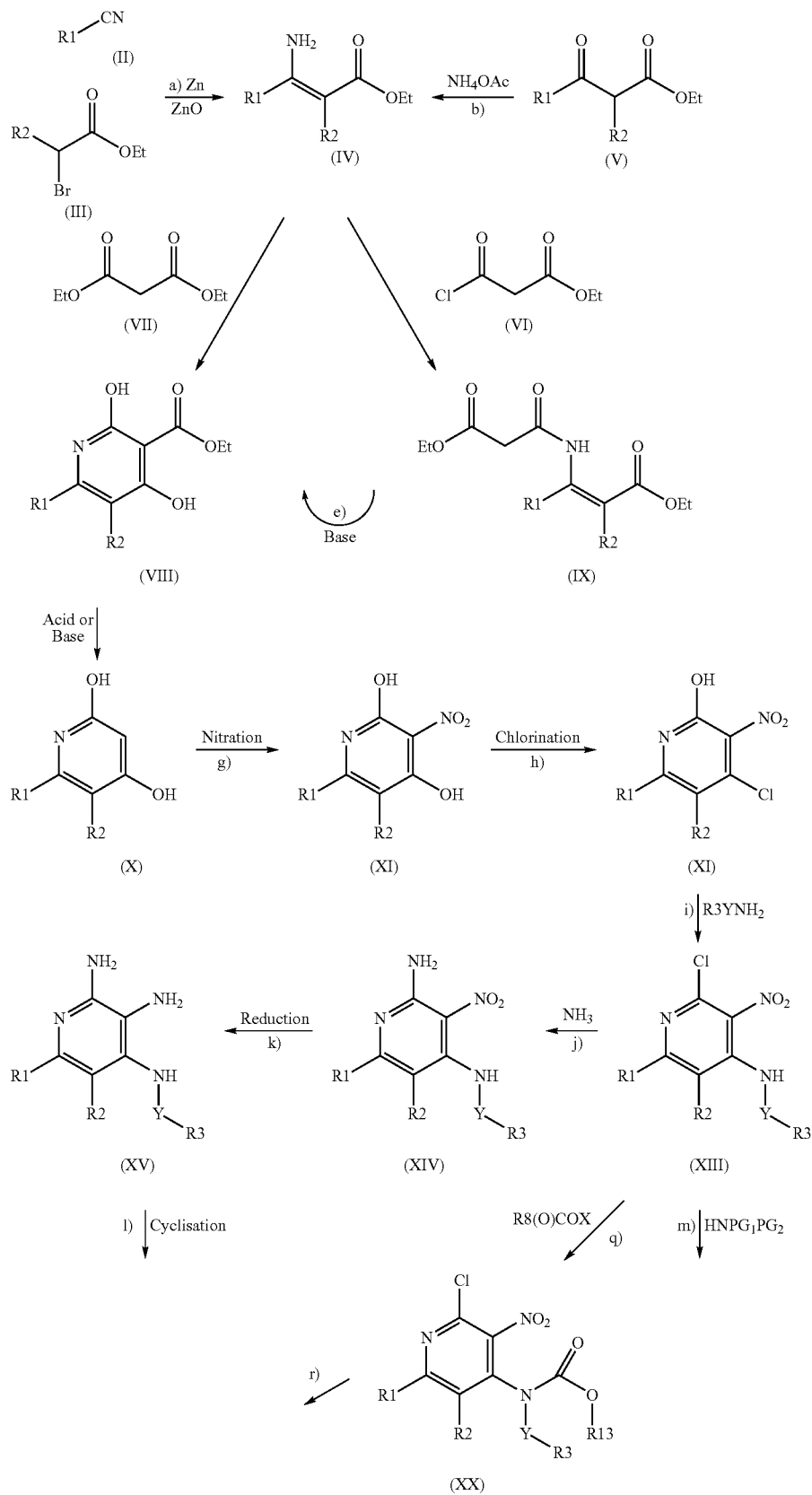
Scheme 1

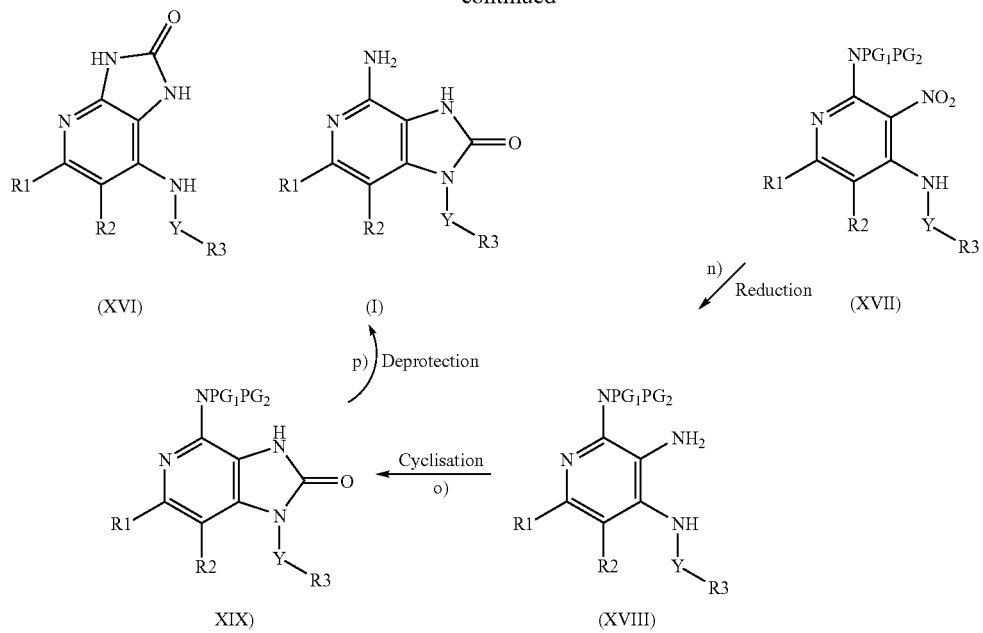

Scheme 1 depicts a variety of means of accessing compounds of formula (I).

a) A commercially available nitrile (II), or nitrile (II) prepared by any of the standard methods described in the chemical literature, is reacted with a halo acetate (III), such as ethylbromoacetate for example, in the presence of a source of Zn. Tet. Letts, 1997, 38, 443-446 describes this conversion to afford an enamine of general structure (IV) provided basic conditions are applied to isolate the product.

b) If acidic conditions are applied to Step a) above, the ketoester (V) is produced, which may then be reconverted to enamine (IV) in a separate step using a source of ammonia, for example ammonium acetate. In this way, a variety of ketoesters of general structure (V) can intercept the above synthetic route at intermediate (IV).

c) The enamine (IV) may then be reacted with a dialkyl malonate (VII) under basic conditions such as sodium ethoxide, sodium hydride or potassium tert-butoxide to give (VIII). J. Org. Chem., 1981, 46 (15), 3040-3048 describes examples of this transformation.

d) Alternatively, the enamine (IV) may be reacted with malonyl dichloride (VI) to give the amidated form (IX) in the presence of a suitable base such as potassium carbonate or triethylamine.

e) (IX) may then be reacted with a suitable base in a separate step to ring close to the pyridine (VIII). Suitable bases include sodium ethoxide, sodium hydride or potassium tert-butoxide.

f) (VIII) is then saponified under either acidic or basic conditions to provide the corresponding acid, for example HCl, HBr, sulfuric acid, sodium hydroxide or lithium hydroxide which under the influence of heat, spontaneously decarboxylates to give the pyridine (X). An example of this transformation is described in WO01101949.

g) (X) may be nitrated using any literature conditions known to those skilled in the art, for example using mixtures of nitric and sulfuric acid or mixtures of acetic and nitric acid to provide the nitro pyridine (XI). For example, Bioorg. Med. Chem. Lett., 1996, 6 (2),173-178, describes such a transformation.

h) (XI) may be chlorinated using a variety of conditions which convert hydroxyl groups to chlorines, such as thionyl chloride or phosphorus oxychloride to give (XII). It will be appreciated by those skilled in the art that the two hydroxyl groups may be chlorinated separately, or converted to an alternative leaving group such as another halogen atom, or an activated ester such as a methane sulfonate ester or a trifluoromethyl sulfonate ester. Examples of all of these processes are included in the sections below.

i) (XII) is reacted with an amine of general formula R3YNH2 which preferentially reacts at the 4-chloro group to give (XIII). Dependent on the nature of the R3Y grouping, some displacement of both chlorine groups or a minor amount of displacement at the 2-chloro group can occur, but does not detract from the ability to secure predominantly (XIII).

j) (XIII) is then reacted with ammonia or an ammonia equivalent such as ammonium acetate to give (XIV).

k) (XIV) may then be reduced under any of the conditions known in the literature to reduce a nitro aromatic compound to an amine using for example iron or tin in HCl, hydrogenation in the presence of a transition metal catalyst such as palladium, platinum or nickel or a chemical reductant such as lithium aluminium hydride to give (XV).

l) (XV) may then be reacted with a source of C=O such as 1,1-carbonyldiimidazole or phosgene to give mixtures of the imidazolones (XVI) and (I), from which (I) may be obtained by careful chromatographic purification.

m) Alternatively, (XIII) may be reacted with a protected form of ammonia, in which two of the hydrogen atoms are replaced with two groups which can later removed under mild conditions, such as dibenzylamine or diallylamine. See, for example, those groups described in 'Protective Groups in Organic Synthesis' by Theodora W Green and Peter G M Wuts, third edition, (John Wiley and Sons, 1999), in particular chapter 7, pages 494-653 ("Protection for the Amino Group"), for alternatives to these examples.

n)-o) See steps k)-l).

p) (XIX) is then deprotected under a variety of conditions suitable for removal of the protecting groups PG1 and PG2 to give (I). See, for example, those groups described in 'Protective Groups in Organic Synthesis' by Theodora W Green and Peter G M Wuts, third edition, (John Wiley and Sons, 1999), in particular chapter 7, pages 494-653 ("Protection for the Amino Group"), and the conditions for their removal.

q) Alternatively, (XIII) can be protected as an alkyl carbamate, $R^{13}CO_2X$ where $R^{13}$ is a $C_{1-6}$ alkyl X is halo, preferably using a strong base such as sodium hydride, potassium tert-butoxide or lithium diisopropylamide in combination with an appropriate acylating agent such as ethylchloroformate or any other alkyl or aryl chloroformate, cyanoformate or anhydride, to form (XX).

r) Steps j) and k) may be applied to (XX) as above, and the products from this sequence can then be regioselectively cyclised to (I) by simple treatment with a protic acid such as acetic or formic acid.

An alternative version of the intermediate (XVII) in which a halogen atom is present at the C2 position, and forms a suitable intermediate (XXVII in scheme 2) for further manipulation can also be used according to scheme 2 below to prepare compounds of general formula (I).

Scheme 2

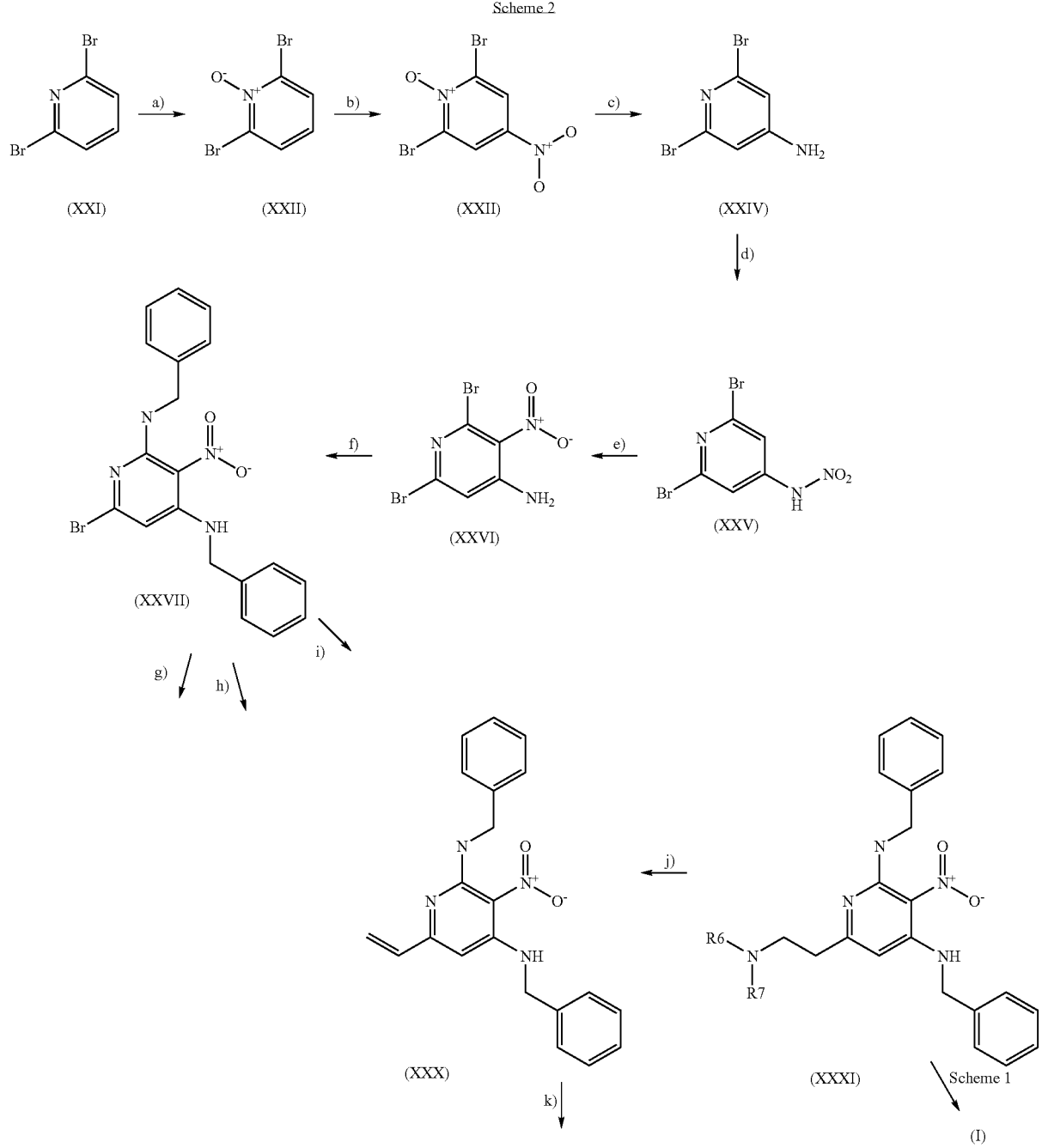

-continued

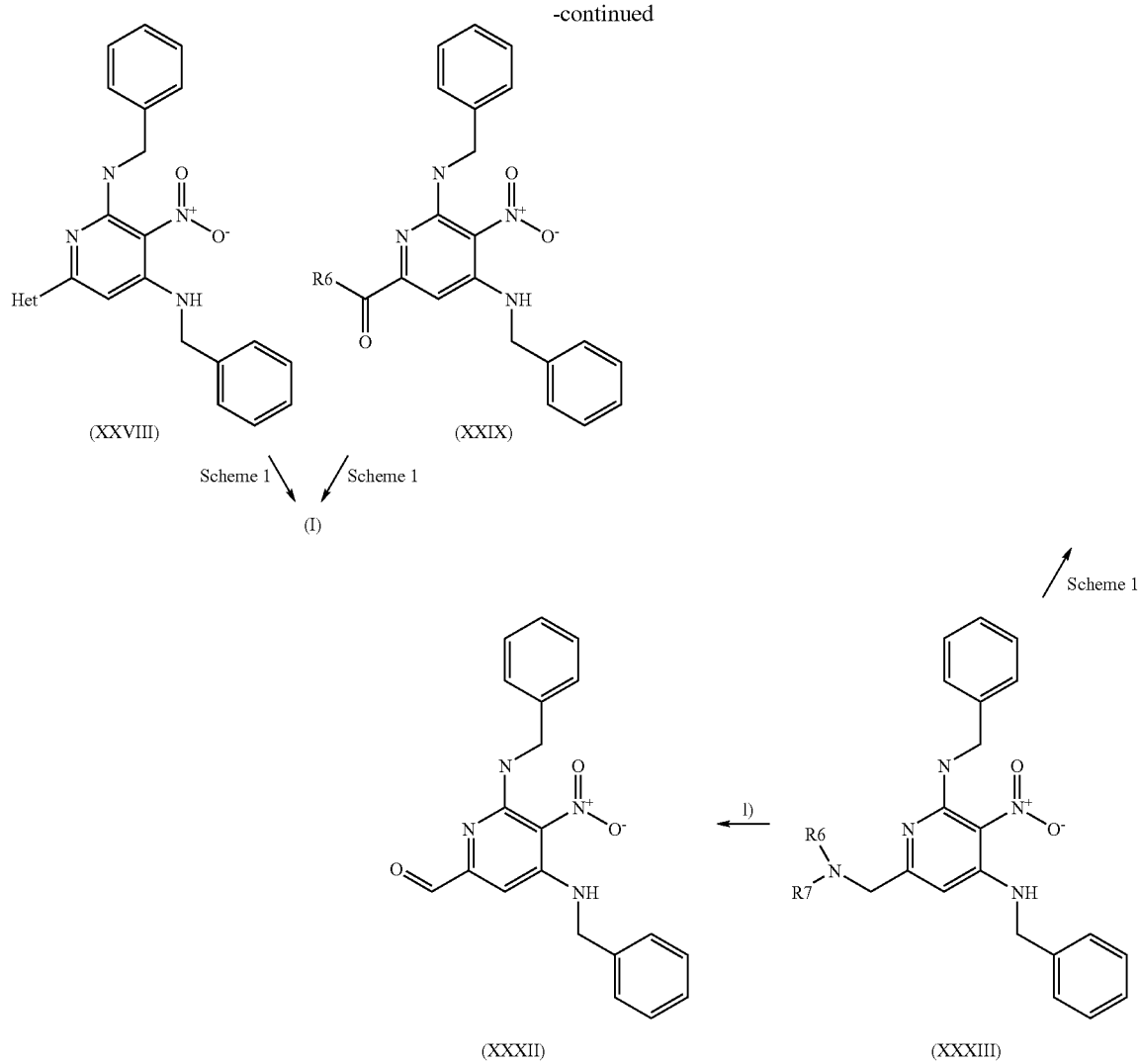

Thus, a commercially available dihalopyridine (e.g. dibromo, XXI), can be taken through a number of steps to provide a range of analogues of general formula (I).

a)-e) Commercially available dibromopyridine (XXI) can be manipulated according to a modified literature procedure (described in WO2005026164) to give the intermediate (XXVI). Many of the steps between (XXI) and (XXVI) rely on either thermally hazardous reagents or generate potentially thermally hazardous products and should therefore be handled with caution.

f) (XXVI) is reacted using a variety of conditions which are known to generate a diazonium species from an amino group, for example nitrous acid, generated in situ from HCl and sodium nitrite, conditions which replace the diazonium species with a Cl atom. The transformation of (XXVI) to the pivotal intermediate (XXVII) may then be completed by addition of an excess of an amine to the crude chloride, for example benzylamine. This step replaces both the C2 and the C4 halogen atoms with the amine group. Any primary or secondary amine groups are suitable for this transformation.

g)-i) The C2 halogen atom in (XXVII) can then be reacted under a variety of conditions to replace the C2 halogen group with a variety of functional groups, to allow access to a range of substituted products (I). For example, a heterocyclic coupling to (XXVII) using a range of organometallic reagents such as boronic acids, zincates, magnesium reagents, cuprates, stannanes etc. gives (XXVIII), a vinyl organometallic reagent such as vinyl tributyl stannane and a palladium catalyst such as Pd(PPh$_3$)$_4$ gives the vinyl species (XXX) and a carbonylation reaction, in which (XXVII) is treated with CO gas under pressure in the presence of a base such as triethylamine and a palladium catalyst to give acyl products of general structure (XXIX). Compounds of structure (XXVIII) and (XXIX) can then be coverted to compounds of formula (I) in accordance with steps n, o, and p of scheme 1.

j)-l) (XXX) can then be manipulated by oxidation to give the aldehyde (XXXII) and then either (XXXII) or (XXXI) can be treated with an amine in the presence of a base such as triethylamine or a reducing agent such as sodium triacetoxyborohydride respectively to give the products (I) (following steps n, o and p of schmeme 1).

An alternative version of intermediate (XIII) can be prepared according to Scheme 3 and then taken through to compounds of formula (I) as follows.

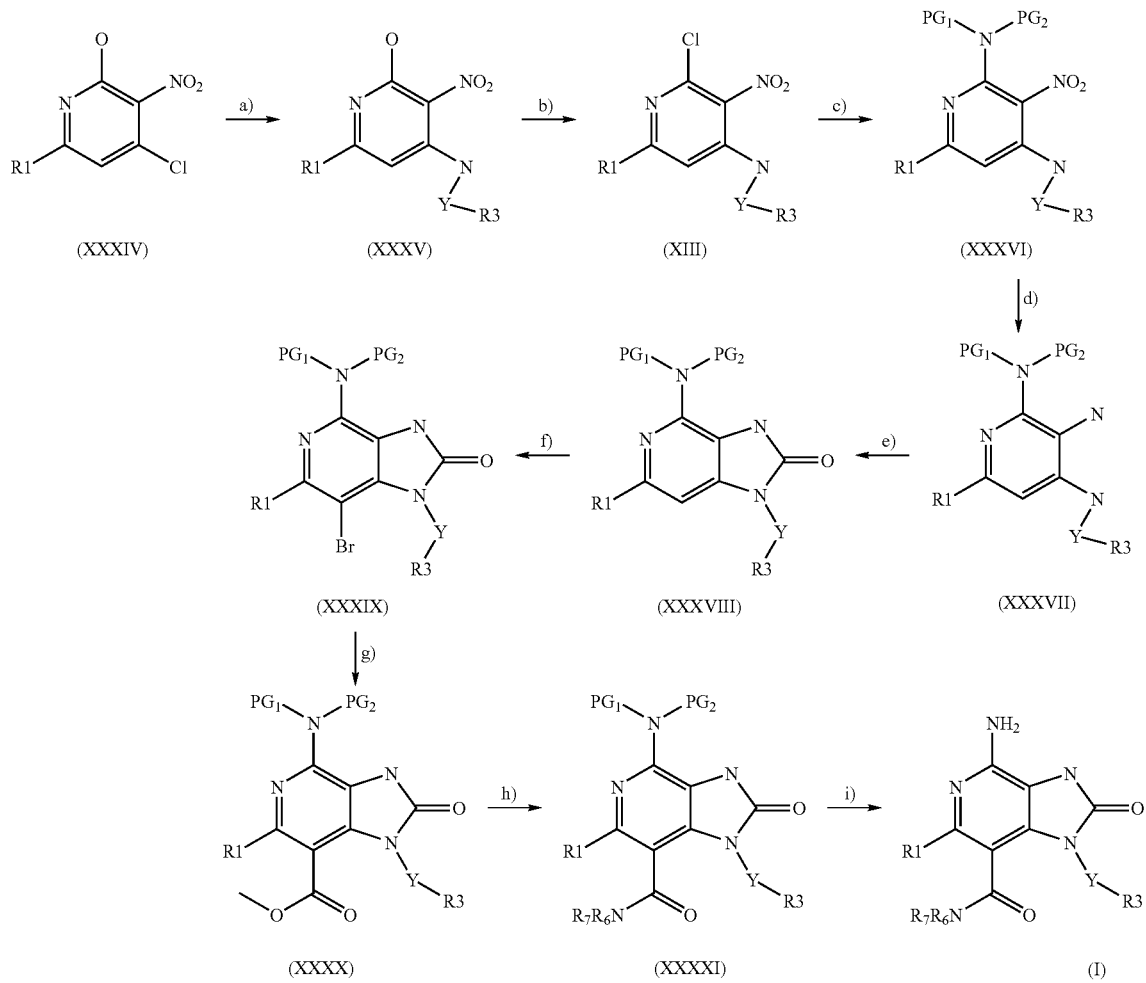

a)-e) Steps a)-e) are similar in nature to those described for Scheme 1, except that the monohalide (XXXIV) is prepared to ensure regiochemical integrity of the C6 and the C4 substituents in (XXXVI).

f) (XXXVIII) may be brominated under a variety of conditions known to those skilled in the art, such as bromine water in a non-polar solvent such as DCM or MeCN to give the C3-bromide (XXXIX).

g) (XXXIX) may then be carbonylated using CO gas under pressure in the presence of a base such as triethylamine, an alcohol such as methanol and a palladium catalyst such as Pd(PPh$_3$)$_4$ to give the ester (XXXX).

h)-i) (XXXX) may then be reacted with an amine NR$^6$R$^7$ to give the amides (XXXXI), which may be deprotected as above to give the products (I).

An alternative synthesis of the intermediate (XI) is shown in Scheme 4 below.

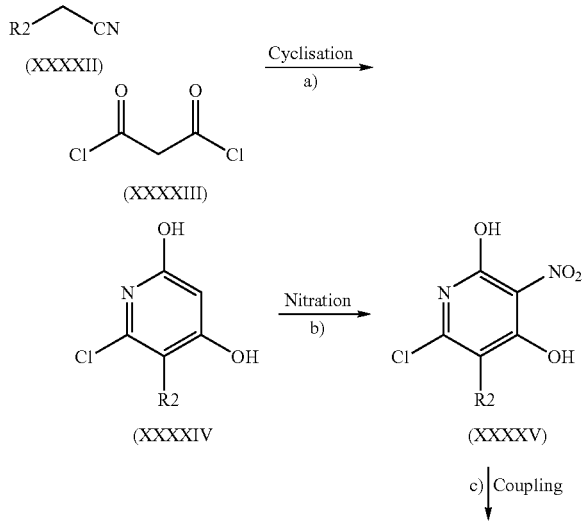

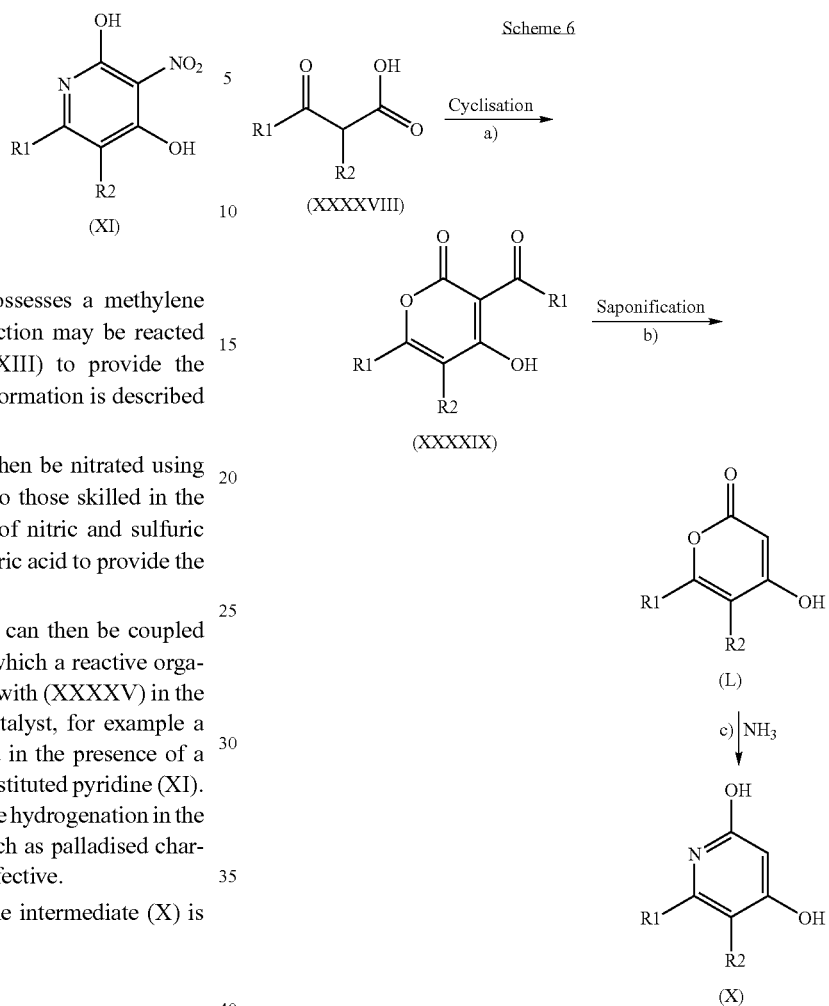

a) Any nitrile (XXXXII) which possesses a methylene group adjacent to the nitrile function may be reacted with malonyl dichloride (XXXXIII) to provide the pyridines (XXXXIV). This transformation is described in Synthesis, 1984, 765-766.

b) The pyridines (XXXXIV) may then be nitrated using any literature conditions known to those skilled in the art, for example using mixtures of nitric and sulfuric acids or mixtures of acetic and nitric acid to provide the nitro pyridine (XXXXV).

c) The chlorine atom in (XXXXV) can then be coupled under a variety of conditions in which a reactive organometallic reagent can be treated with (XXXXV) in the presence of a transition metal catalyst, for example a stannane, zincate or boronic acid in the presence of a palladium catalyst, to give the substituted pyridine (XI). In the cases where R1=H, a simple hydrogenation in the presence of a suitable catalyst such as palladised charcoal or palladium hydroxide is effective.

A further alternative synthesis of the intermediate (X) is shown in Scheme 5 below.

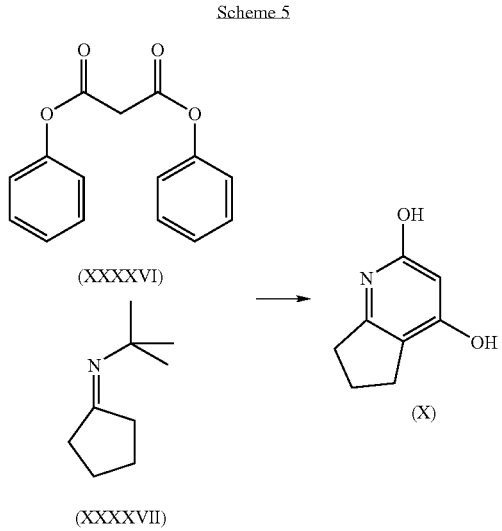

In this method, a malonyl ester, preferably a diphenyl ester (XXXXVI) is reacted with a Schiff's base (XXXXVII) and heated to produce the pyridine of general formula (X).

A further alternative means of accessing compounds of general formula (X) is shown in Scheme 6.

a) Ketoacids of general formula (XXXXVIII), which are either available commercially or can be made directly by saponification of ketoesters of formula (V) are reacted with a source of C=O, such as 1,1-carbonyldiimidazole in a suitable solvent at elevated temperature to produce the cyclised pyranones (XXXXIX).

b) (XXXXIX) is treated with a strong mineral acid such as sulfuric acid or hydrochloric acid to eliminate the C3-acyl substituent and give the pyranones (L).

c) (L) may be reacted with a source of ammonia such as concentrated aqueous ammonium hydroxide under heating to convert the pyranone ring into the pyridines (X), to intercept the same intermediate described in Scheme 1. Alternatively, several pyranones of general formula (L) are available from commercial sources, which can be applied directly to Step c. Conversion of compounds of general formula (L) to those of general formula (X) is described in several sources, for example WO9504730.

An alternative means of accessing compounds of general formula (XIX) is shown in Scheme 7.

Scheme 7

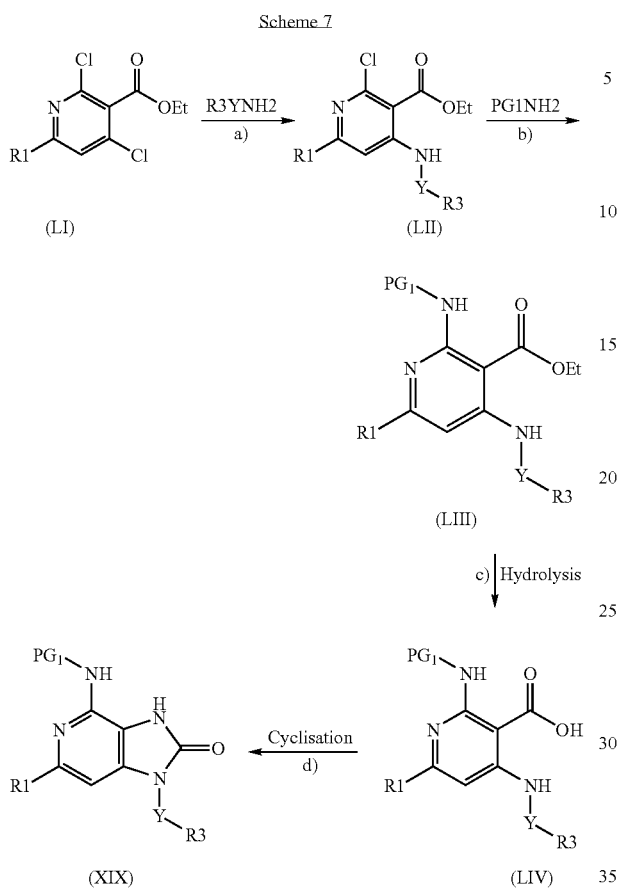

d) (LIV) may then be reacted with a reagent which is known to convert an acid into an acyl azide, for example diphenylphosphoryl azide. Under the influence of heat, the intermediate acyl azide undergoes a rearrangement in which an isocyanate is produced and is trapped internally by 4-amino substituent to give the imidazolones (XIX), thereby intercepting the same intermediate described in Scheme 1.

An alternative means of accessing compounds of general formula (I) is shown in Scheme 8.

Scheme 8

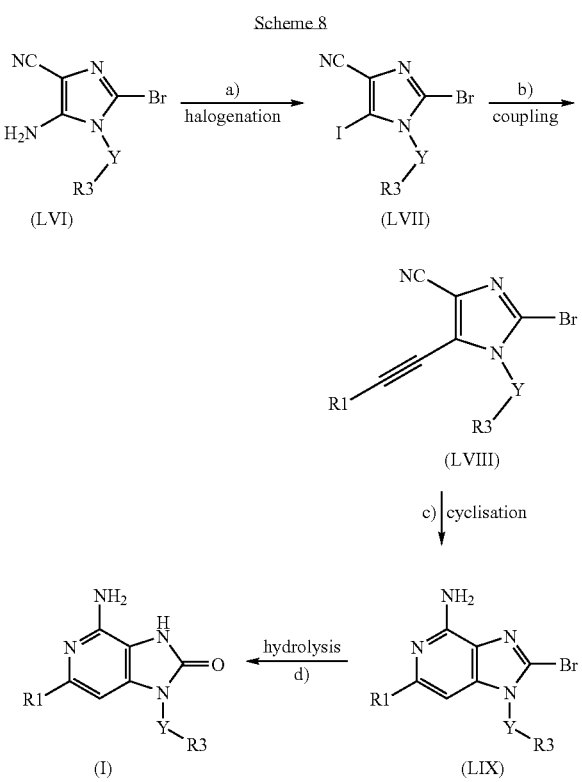

a) Commercially available dichloropyridines of general formula (LI) can be reacted with an amine of formula R3YNH2 to selectively displace the 4-chloro group to give the pyridines (LII).

b) (LII) can then be reacted with a protected form of ammonia PG1 NH2 or PG1 PG2NH to displace the 2-chloro group, in which two of the hydrogen atoms are replaced with two groups which can later removed under mild conditions, such as benzylamine, allylamine, dibenzylamine or diallylamine. See, for example, those groups described in 'Protective Groups in Organic Synthesis' by Theodora W Greene and Peter G M Wuts, third edition, (John Wiley and Sons, 1999), in particular chapter 7, pages 494-653 ("Protection for the Amino Group"), for alternatives to these examples. If an excess of the amine group from Step a, R3YNH2 is used, this group can displace both the 2 and the 4-chloro groups.

c) The ester of (LII) may be hydrolysed under a variety of conditions which are known to deprotect esters, for example sodium hydroxide or lithium hydroxide to give the acid (LIV). See, for example, those conditions described in 'Protective Groups in Organic Synthesis' by Theodora W Greene and Peter G M Wuts, third edition, (John Wiley and Sons, 1999), in particular chapter 5, pages 373-441 ("Protection for the Carboxyl Group"), for alternatives to these reagents.

a) (LVI), prepared according to Org. BioMol. Chem., 2003, 1, 1354-1365, may be halogenated by reaction of the amino group in (LVI) with an activating reagent, for example isoamyl nitrite and a halogenating agent such as diiodo or dibromomethane to give the halogenated material (LVII).

b) (LVII) may then undergo a variety of transition metal-mediated coupling reactions in which the iodo group is selectively reacted with, for example, a terminal alkyne. For examples of this transformation on an imidazole template, see J. Med. Chem., 34(2), 1991, 778-786 c) (LVIII) may then be reacted with ammonia, to cyclise the alkynyl-nitrile to a pyridine ring. For examples of this transformation on an imidazole template, see for example Tetrahedron, 49(3), 1993, 557-570.

d) The bromine atom in (LIX) may then be hydrolysed under either strongly acidic conditions, for example hydrochloric acid or sulfuric acid, or reacted with a nucleophilic source of OH, such as sodium hydroxide or sodium methoxide, followed by a milder acidic hydrolysis to give (I).

The intermediate (LVIII) can also be used according to Scheme 9 below to prepare compounds of general formula (I).

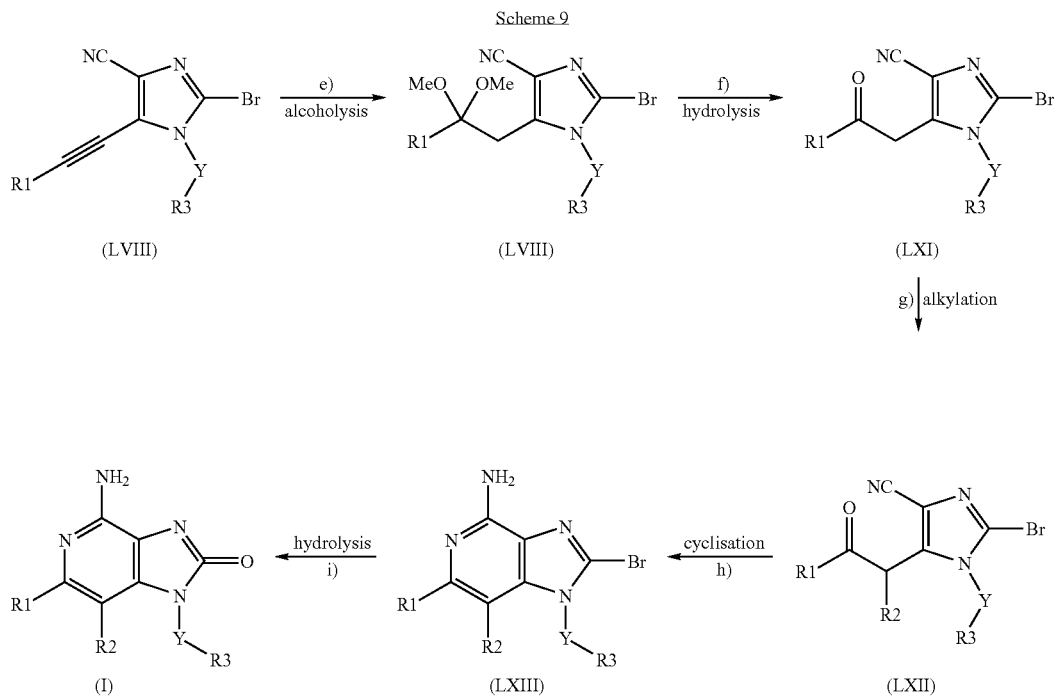

e) (LVIII) may be reacted with an alcohol, for example methanol, ethanol, propanol, or any other alcohol, to form the acetal (LX) under mild heating.

f) The acetal (LX) may then undergo hydrolysis under any conditions which are known to hydrolyse acetals or ketals to ketones, for example aqueous hydrochloric acid. See, for example, those conditions described in 'Protective Groups in Organic Synthesis' by Theodora W Green and Peter G M Wuts, third edition, (John Wiley and Sons, 1999), in particular chapter 4, pages 297-347 ("Protection for the Carbonyl Group"), for alternatives to these conditions.

g) The ketone (LXI) may then be alkylated in the presence of a suitable base such as sodium hydride, potassium tert-butoxide or potassium carbonate and an alkylating agent such as an alkyl halide, alkyl sulfonate or alkyl trifluoromethane sulfonate to give (LXII).

h) (LXII) may then be reacted with ammonia, to cyclise the keto-nitrile to a pyridine ring.

i) The bromine atom in (LXIII) may then be hydrolysed under either strongly acidic conditions, for example hydrochloric acid or sulfuric acid, or reacted with a nucleophilic source of OH, such as sodium hydroxide or sodium methoxide, followed by a milder acidic hydrolysis to give (I). During the alcoholysis Step e, elevated temperature can lead to the bromine atom being displaced with an alcohol, which will then introduce an alternative means of introducing the oxo group in (I).

Schemes 8 and 9 are illustrated using bromo (which is preferred), but it will be appreciated that other halo atoms can also be used.

An alternative synthesis of the intermediate (XVII) is shown in Scheme 10 below.

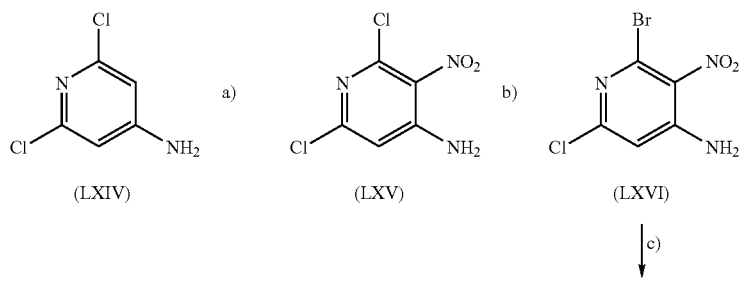

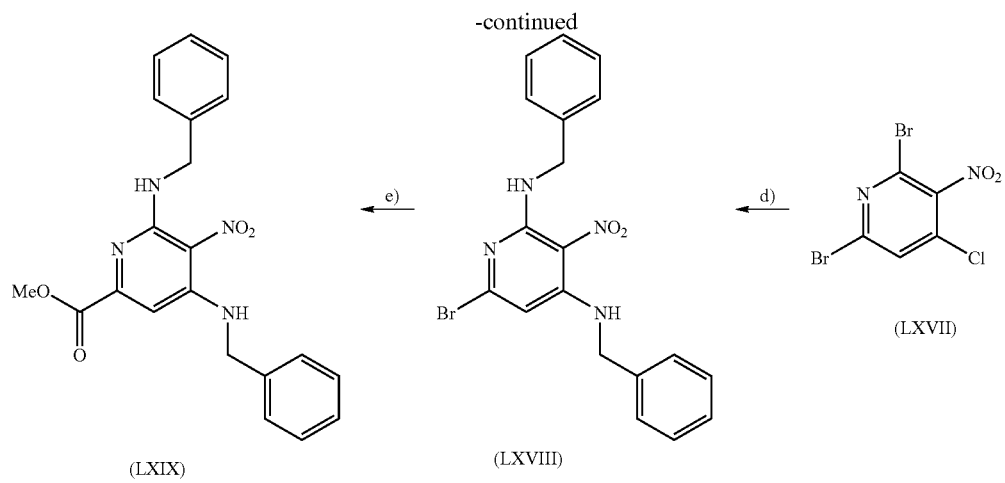

a) (LXIV) may be treated under any nitration conditions known to those skilled in the art. It is known that transformations of this type proceed through an intermediate N-nitro analogue. For example, see the analogous chemistry described in WO2005026164.
b) (LXV) is treated with HBr to convert the chlorine atoms to bromines (LXVI).
c) (LXVI) is then treated with any conditions known to those skilled in the art which convert an amino group to an N-nitroso or diazonium group, which is then treated with HCl to produce the chloride (LXVII).
d) (LXVII) is treated with an amine PG1NH, for example benzylamine to displace both the 4-chloro and the 2-bromo groups to give (LXVIII).
e) The remaining 6-bromo group can then be used to introduce a variety of substituents using transition metal-mediated methods, for example Pd-catalysed carbonylation, organometallic cross-coupling reactions via Sn, Zn, or B reagents or with Li or Mg reagents using Fe or Ni as catalysts. In the example shown, a carbonylation produces the particular analogue (LXIX) shown. This can then be converted to a compound of formula (I) in accordance with steps n, o and p of scheme 1.

An alternative means of accessing compounds of general formula (XIX) is shown in Scheme 11.

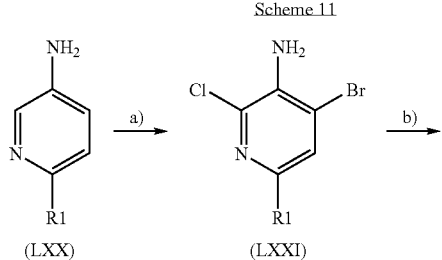

Scheme 11

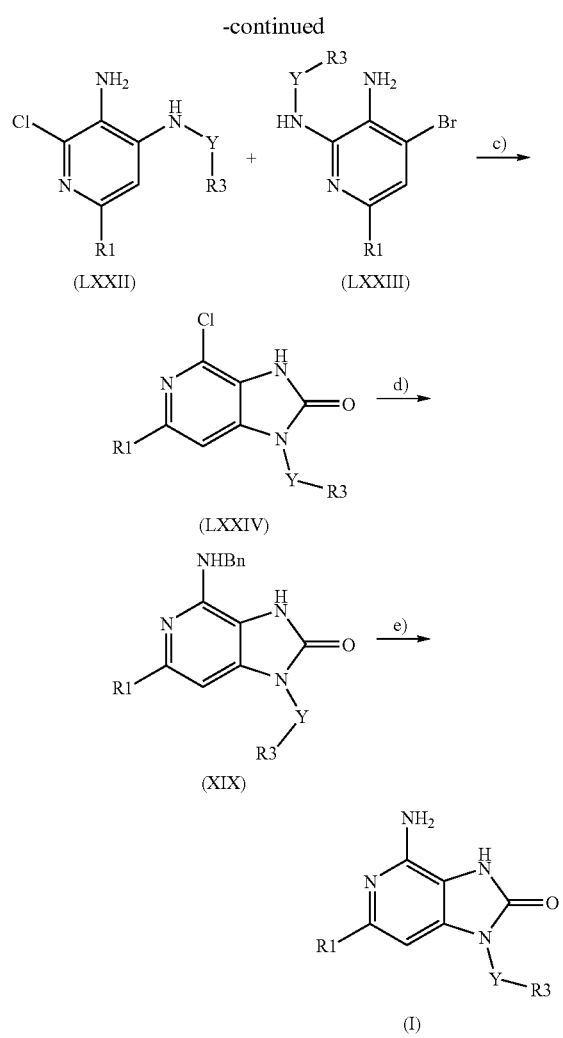

a) (LXX) is sequentially halogenated to give the dihalopyridine (LXXI) under a variety of conditions which can introduce a halogen atom, for example NCS, NBS, NIS, bromine water etc.

b) (LXXI) is then treated with an amine of general structure R3YNH2 to give a mixture of the two compounds (LXXII) and (LXXIII).

c)-e) The desired compound, (LXXII) may then be cyclised, the remaining halogen displaced and then final deprotection may give (I).

A further method of preparing compounds of general formulae (X), (XI) and (I) is shown in Scheme 12.

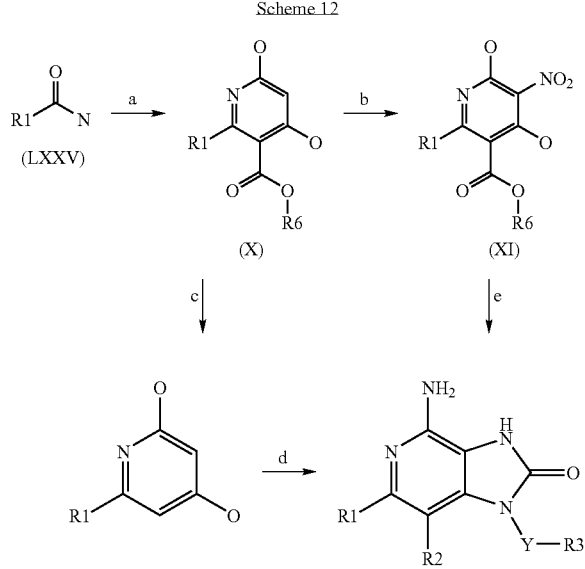

a) Thus, a commercially available amide of formula (LXXV) may be reacted with a malonyl diester, for example a dialkyl-1,3-acetonedicarboxylate in the presence of a strong base, under conditions which lead to the in situ formation of a nitrile, via dehydration of the starting amide, for example using a common dehydrating agent such as $POCl_3$, $SOCl_2$, PPA or triflic anhydride. These conditions lead directly to the formation of the dihydroxypyridine (X).

b) (X) may be nitrated according to the methods described in Scheme 1 to give (XI).

c) (X) may be saponified and decarboxylated according to the methods described in Scheme 1.

d and e) (X) or (XI) can then be converted to compounds of formula (I) using any of the methods described in Scheme 1.

Methods to prepare prodrug derivatives of (I) are shown in Scheme 13 below.

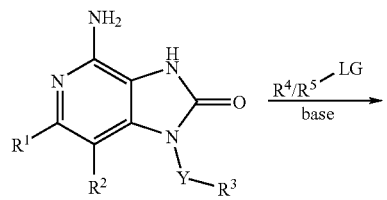

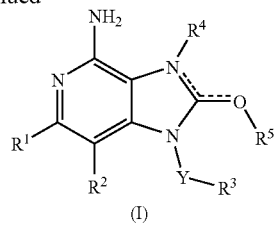

Reaction of active parent compounds with a reagent which features the group $R^4$ or $R^5$ attached to a suitable leaving group in the presence of a suitable base provides prodrug derivatives of (I). Suitable reagents include but are not limited to alkyl halides, acid chlorides, chloroformates and carbamoyl chlorides shown below.

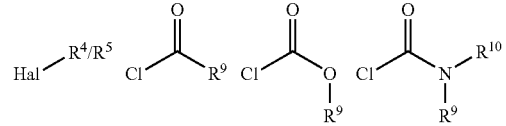

Suitable bases include triethylamine, diisopropylethylamine, potassium carbonate, cesium carbonate, sodium hydride and n-butyllithium. A range of solvents can also be used to effect this transformation, including but not limited to THF, acetonitrile, dimethylformamide, dichloromethane and diethyl ether. The specific choice of both solvent and base can influence the regioselectivity of the alkylation/acylation reaction i.e. whether the reacting group is appended to the O atom ($R^5$) or the N atom ($R^4$). For example, the reaction of a parent molecule with ethyl chloroformate in the presence of triethylamine in DCM will give predominantly O acylation.

All of the above reactions and the preparations of novel starting materials disclosed in the preceding methods are conventional and appropriate reagents and reaction conditions for their performance or preparation as well as procedures for isolating the desired products will be well known to those skilled in the art with reference to literature precedents and the examples and preparations hereto.

The compounds of the invention are useful because they have pharmacological activity in mammals, including humans. More particularly, they are useful in the treatment of a disorder in which the modulation, especially agonism, of TLR7 is implicated.

In a further aspect, the invention further provides a compound of formula (I) or a pharmaceutically acceptable salt or solvate thereof for the treatment of a disorder or condition where modulation of TLR7 receptor is implicated.

Thus the invention provides a compound of formula (I) or a pharmaceutically acceptable salt or solvate thereof for the treatment of a disorder or condition where modulation of TLR7 receptor is known, or can be shown, to produce a beneficial effect.

In a yet further aspect, the compounds of the invention are useful in the treatment of viral infections, scuh as infections caused by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, or respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a retrovirus (e.g., a lentivirus such as HIV) or a filovirus (e.g., ebola virus or marburg virus).

In a further aspect, the compounds of the invention are useful in the treatment of Hepatitis C viral infection.

In a yet further aspect, the compounds of the invention are useful to treat tumors or cancers including but not limited to carcinomas, sarcomas, and leukemias, e.g. squamous cell carcinoma, renal cell carcinoma, Kaposi's sarcoma, melanoma, renal cell carcinoma, myelogeous leukemia, chronic lymphocytic leukemia, multiple myeloma, non-Hodgkin's lymphoma.

In a yet further aspect, the compounds of the invention are useful to treat bacterial, fungal, and protozoal infections including but not limited to infections caused by bacteria of the genus *Escherichia, Enterobacter, Salmonella, Staphylococcus, Klebsiella, Proteus, Pseudomonas, Streptococcus, Chlamydia*; or fungal infections such as candidiasis, aspergillosis, histoplasmosis, cryptococcal meningitis.

In a yet further aspect, the compounds of the invention are useful to treat T- helper cells (Th2) mediated diseases (see e.g. Dabbagh et al., Curr Opin Infect Dis 2003, 16: 199-204, incorporated herein by reference), including but not limited to atopic diseases, such as atopic dermatitis or eczema, eosinophilia, asthma, allergy, allergic rhinitis.

In a yet further aspect, the compounds of the invention are useful for the treatment of damaged or ageing skin such as scarring and wrinkles.

In a yet further aspect, the compounds of the invention are useful in the treatment of autoimmune diseases, such as Crohns disease and inflammatory bowel disease.

The compounds of formula (I) and the pharmaceutically acceptable salts or solvates hereof, may be administered alone or as part of a combination therapy. Thus included within the scope of the present invention are embodiments comprising co-administration of, and compositions which contain, in addition to a compound of the invention, one or more additional therapeutic agents.

In one embodiment, combinations of the present invention include treatment with a compound of formula (I) or a pharmaceutically acceptable salt or solvate thereof, and one or more additional agents having anti-HCV activity, i.e. agents which can inhibit a target such as, but not limited to, HCV NS3 protein, HCV NS5A protein, HCV NS4B protein, HCV polymerase, HCV metalloprotease, HCV serine protease, HCV helicase, p7 protein. Examples of such agents include, but are not limited to, interferons, pegylated interferons (e.g. peginterferon alfa-2a and peginterferon alfa-2b), long-acting interferons (e.g. albumin-interferon alfa), lamivudine, ribavarin, emtricitabine, viramidine, celgosivir, valopicitabine, HCV-086, HCV-796, EMZ702, BILN2061, IDN6566, NM283, SCH 6 and VX-950.

In a further embodiment, combinations of the present invention include treatment with a compound of formula (I) or a pharmaceutically acceptable salt or solvate thereof, and one or more TLR agonists e.g. agonists of TLR3, TLR7, TLR8 or TLR9 receptors.

In a further embodiment, combinations of the present invention include treatment of HCV-HIV co-infection with a compound of formula (I) or a pharmaceutically acceptable salt or solvate thereof, and one or more additional antiviral agents selected from HIV protease inhibitors (PIs), non-nucleoside reverse transcriptase inhibitors (NNRTIs), nucleoside/nucleotide reverse transcriptase inhibitors (NR-TIs), CCR5 antagonists, agents which inhibit the interaction of gp120 with CD4, agents which inhibit the entry of HIV into a target cell (such as fusion inhibitors), integrase inhibitors, prenylation inhibitors, RNaseH inhibitors and maturation inhibitors.

Examples of NNRTIs include, but are not limited to, efavirenz, HBY-097, nevirapine, TMC-120 (dapivirine), TMC-125, etravirine, delavirdine, DPC-083, DPC-961, capravirine, rilpivirine, 5-{[3,5-Diethyl-1-(2-hydroxyethyl)-1H-pyrazol-4-yl]oxy}isophthalonitrile or pharmaceutically acceptable salts, solvates or derivatives thereof; GW-678248, GW-695634, MIV-150, calanolide, and tricyclic pyrimidinone derivatives as disclosed in WO 03/062238.

Examples of CCR5 antagonists include, but are not limited to, TAK-779, SC-351125, ancriviroc (formerly known as SCH—C), vicriviroc (formerly known as SCH-D), maraviroc, PRO-140, aplaviroc (also known as GW-873140, Ono-4128, AK-602), AMD-887 CMPD-167, methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate or pharmaceutically acceptable salts, solvates or derivatives thereof, methyl 3-endo-{8-[(3S)-3-(acetamido)-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate or pharmaceutically acceptable salts, solvates or derivatives thereof, ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate or pharmaceutically acceptable salts, solvates or derivatives thereof, and N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide) or pharmaceutically acceptable salts, solvates or derivatives thereof.

Examples of entry and fusion inhibitors include, but are not limited to, BMS-806, BMS-488043, 5-{(1S)-2-[(2R)-4-Benzoyl-2-methyl-piperazin-1-yl]-1-methyl-2-oxo-ethoxy}-4-methoxy-pyridine-2-carboxylic acid methylamide and 4-{(1S)-2-[(2R)-4-Benzoyl-2-methyl-piperazin-1-yl]-1-methyl-2-oxo-ethoxy}-3-methoxy-N-methyl-benzamide, enfuvirtide (T-20), sifuvirtide SP-01A, T1249, PRO 542, AMD-3100, soluble CD4, compounds disclosed in JP 2003171381, and compounds disclosed in JP 2003119137.

Examples of inhibitors of HIV integrase include, but are not limited to, L000870810, GW-810781, 1,5-naphthyridine-3-carboxamide derivatives disclosed in WO 03/062204, compounds disclosed in WO 03/047564, compounds disclosed in WO 03/049690, and 5-hydroxypyrimidine-4-carboxamide derivatives disclosed in WO 03/035076, MK-0518 (5-(1,1-dioxo-1,2-thiazinan-2-yl)-N-(4-fluorobenzyl)-8-hydroxy-1, 6-naphthyridine-7-carboxamide- disclosed in WO 03016315), GS-9137 (JTK-303).

Examples of prenylation inhibitors include, but are not limited to, HMG CoA reductase inhibitors, such as statins (e.g. atorvastatin).

Examples of maturation inhibitors include 3-O-(3'3'-dimethylsuccinyl) betulic acid (otherwise known as PA-457) and alphaHGA.

In yet a further embodiment, combinations of the present invention include treatment with a compound of formula (I), or a pharmaceutically acceptable salt, solvate or polymorph thereof, and one or more additional agents such as, but not limited to, antifungals, e.g. fluconazole, fosfluconazole, itraconazole or voriconazole; antibacterials e.g. azithromycin or clarithromycin; interferons, daunorubicin, doxorubicin, and paclitaxel for the treatment of AIDS related Kaposi's sarcoma; and cidofovir, fomivirsen, foscarnet, ganciclovir and valcyte for the treatment of cytomegalovirus (CMV) retinitis.

In yet a further embodiment, combinations of the present invention include treatment with a compound of formula (I), or a pharmaceutically acceptable salt or solvate thereof, and one or more additional therapeutic agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (IS-COM), which comprises a vaccine formulation that combines a multimeric 5 presentation of antigen and an adjuvant.

Further combinations for use according to the invention include combination of a compound of formula (I), or a pharmaceutically acceptable salt or solvate thereof with a CCR1 antagonist, such as BX-471; a beta adrenoceptor agonist, such as salmeterol; a corticosteroid agonist, such as fluticasone propionate; a LTD4 antagonist, such as montelukast; a muscarinic antagonist, such as tiotropium bromide; a PDE4 inhibitor, such as cilomilast or roflumilast; a COX-2 inhibitor, such as celecoxib, valdecoxib or rofecoxib; an alpha-2-delta ligand, such as gabapentin or pregabalin; a TNF receptor modulator, such as a TNF-alpha inhibitor (e.g. adalimumab); or an immunosuppressant, such as cyclosporin or a macrolide such as tacrolimus.

There is also included within the scope the present invention, combinations of a compound of formula (I), or a pharmaceutically acceptable salt or solvate thereof, together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include, but are not limited to, ritonavir, saquinavir or ketoconazole.

In the above-described combinations, the compound of formula (I) or a pharmaceutically acceptable salt or solvate thereof and other therapeutic agent(s) may be administered, in terms of dosage forms, either separately or in conjunction with each other; and in terms of their time of administration, either simultaneously or sequentially. Thus, the administration of one component agent may be prior to, concurrent with, or subsequent to the administration of the other component agent(s).

It is to be appreciated that all references herein to treatment include curative, palliative and prophylactic treatment.

It will be appreciated that the invention includes the following aspects.

(i) A compound of formula (I) or a tautomer thereof or a pharmaceutically acceptable salt or solvate of said compound or tautomer;

(ii) A pharmaceutical composition comprising a compound of formula (I) as defined in any one of the preceding claims, or a tautomer thereof or a pharmaceutically acceptable salt or solvate of said compound or tautomer, together with one or more pharmaceutically acceptable excipients;

(iii) A compound of formula (I) or a tautomer thereof or a pharmaceutically acceptable salt or solvate of said compound or tautomer for use as a medicament;

(iv) A compound of formula (I) or a tautomer thereof or a pharmaceutically acceptable salt or solvate of said compound or tautomer for the treatment of a disorder or condition in which modulation of the TLR7 receptor is implicated;

(v) Use of a compound of formula (I) or a tautomer thereof or a pharmaceutically acceptable salt or solvate of said compound or tautomer in the preparation of a medicament for the treatment of a disorder or condition in which modulation of the TLR7 receptor is implicated;

(vi) A pharmaceutical composition including one or more additional therapeutic agents;

(vii) A pharmaceutical product (such as in the form of a kit) comprising a compound of formula (I) or a tautomer thereof or a pharmaceutically acceptable salt or solvate of said compound or tautomer, together with an additional therapeutically active agent as a combined preparation for simultaneous, separate or sequential use in the treatment of a disorder in which modulation of the TLR7 receptor is implicated.

(viii) use of a compound of formula (I) or a tautomer thereof or a pharmaceutically acceptable salt or solvate of said compound or tautomer in the preparation of a medicament for use in combination with an additional therapeutically active agent for simultaneous, separate or sequential use in the treatment of a disorder in which modulation of the TLR7 receptor is implicated.

(ix) A method of treatment of a disorder or condition where modulation of TLR7 receptor is implicated in a mammal, comprising administering to said mammal a therapeutically effective amount of a compound of formula (I) a tautomer thereof or a pharmaceutically acceptable salt or solvate of said compound or tautomer.

(x) a process for the preparation of a compound of formula (I) or a tautomer thereof or a pharmaceutically acceptable salt or solvate of said compound or tautomer.

(xi) certain novel intermediates disclosed herein.

The invention is illustrated by the following non-limiting examples in which the following abbreviations and definitions are used:

| | |
|---|---|
| Arbocel ® | Filtration agent, from J. Rettenmaier & Sohne, Germany |
| APCI$^+$ | Atmospheric Pressure Chemical Ionisation (positive scan) |
| Bn | Benzyl |
| br | Broad |
| d | Doublet |
| dd | Doublet of doublets |
| DMSO | Dimethylsulfoxide |
| ELSD | Evaporative Light Scattering Detection |
| ES$^+$ | Electrospray ionisation positive scan. |
| ESI | Electrospray ionisation (positive or negative scan) |
| eq | Equivalent |
| HRMS | High Resolution Mass Spectroscopy |
| $^1$H NMR | Proton Nuclear Magnetic Resonance Spectroscopy |
| LC-MS | Liquid Chromatography - Mass Spectrometry |
| LRMS | Low Resolution Mass Spectroscopy |
| m | Multiplet |
| m/z | Mass spectrum peak |
| Reacti-Vial ™ | Reaction Vial available from Fisher Scientific, US |
| q | Quartet |
| s | Singlet |
| t | Triplet |
| □ | Chemical shift |
| * | denotes the point of attachment |

EXAMPLE 1

4-Amino-1-benzyl-6-cyclopropyl-1,3-dihydro-imidazo[4,5-c]pyridin-2-one

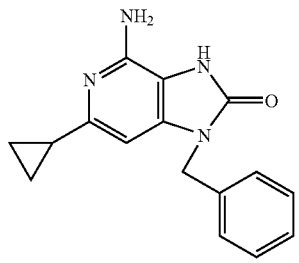

4-Allylamino-1-Benzyl-6-cyclopropyl-1,3-dihydro-imidazo[4,5-c]pyridin-2-one (70 mg, 0.2 mmol) was dissolved in ethanol (2 mL) and 10% Pd—C (70 mg, w/w) was added followed by dropwise addition of $BF_3.OEt_2$ (27 □l, 0.2 mmol). The mixture was heated at reflux under $N_2$ overnight. The mixture was allowed to cool to room temperature and filtered through arbocel, rinsing with fresh EtOH and the filtrate was concentrated in vacuo to give the crude (150 mg). Column chromatography through silica eluting with 98:2→95:5 DCM:MeOH gave the title compound (17 mg) as an off white solid.

$^1$H NMR ($CD_3OD$) □ 7.35-7.27 (m, 5H), 6.26 (s, 1H), 5.00 (s, 2H), 1.89-1.82 (m, 1H), 0.85-0.80 (m, 2H), 0.77-0.73 (m, 2H); HRMS for $C_{16}H_{16}N_4O$ calculated 281.1397, found 281.1395.

EXAMPLE 2

4-Amino-1-benzyl-6-methyl-1,3-dihydro-imidazo[4,5-c]pyridin-2-one

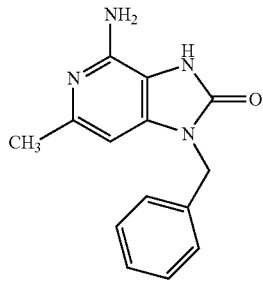

1-Benzyl-4-dibenzylamino-6-methyl-1,3-dihydro-imidazo[4,5-c]pyridin-2-one (34 mg, 0.08 mmol) was suspended in ethanol (5 mL) and hydrogenated over 10% $Pd(OH)_2$ (7 mg) at room temperature, 60 psi for 6 hours. The reaction mixture was filtered through a short plug of Arbocel and the filtrate was then evaporated in vacuo to an opaque gum. The gum was dissolved in methanol and preabsorbed onto silica gel and was then purified by column chromatography, eluting with 5% methanol in EtOAc. Appropriate fractions were combined and evaporated in vacuo to give the title compound as a white solid, 7 mg.

$^1$H NMR ($CD_3OD$) □ 2.31 (s, 3H), 5.01 (s, 2H), 6.40 (s, 1H), 7.31 (m, 5H).

LRMS ($ES^+$) m/z 255 ($MH^+$).

EXAMPLE 3

1-Benzyl-4-amino-6,7-dimethyl-1,3-dihydro-imidazo[4,5-c]Pyridin-2-one

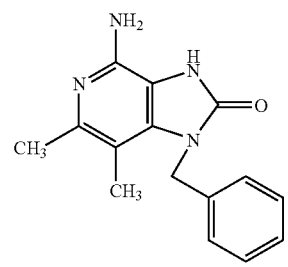

1-Benzyl-4-diallylamino-6,7-dimethyl-1,3-dihydro-imidazo[4,5-c]pyridin-2-one (358 mg, 1 mmol) was taken up in water (10 mL) and acetonitrile (25 mL) and $RhCl(PPh_3)_3$ (286 mg, 0.3 mmol) was added in one portion and the mixture then heated at reflux for 16 h. The mixture was allowed to cool to room temperature, and then concentrated in vacuo, and the residue purified by column chromatography on silica gel using a gradient of 95:5→85:15 DCM:MeOH to afford the title compound as a pale brown solid (77 mg, 29%).

$^1$H NMR (DMSO) □ 1.98 (s, 3H), 2.14 (s, 3H), 5.13 (s, 2H), 5.34 (s, 2H), 7.03-7.31 (m, 5H), 10.38 (s, 1H).

LRMS ($ES^+$) m/z 269 $[MH]^+$

EXAMPLE 4

4-Amino-1-benzyl-2-oxo-2,3-dihydro-1H-imidazo[4,5-c]pyridine-6-carboxylic acid methyl ester

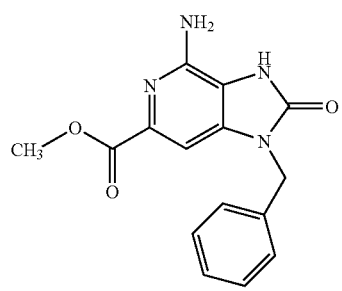

1-Benzyl-4-benzylamino-2-oxo-2,3-dihydro-1H-imidazo[4,5-c]pyridine-6-carboxylic acid methyl ester (0.02 g) was taken up in sulfuric acid (2 mL), and stirred rapidly for 15 mins. The reaction mixture was cooled to 0C, and water was added, which resulted in a precipitate which was filtered and dried in vacuo to give the title compound (10 mg) as a white solid.

¹H NMR (d6-DMSO, 400 MHz) ☐ 3.75 (s, 3H), 4.95 (s, 2H), 7.20-7.50 (m, 6H), 10.20 (s, 1H). LRMS (ES+) m/z 299 [MH]⁺

EXAMPLE 5

4-Amino-1-benzyl-6-pyrazin-2-yl-1,3-dihydro-imidazo[4,5-c]pyridine-2-one

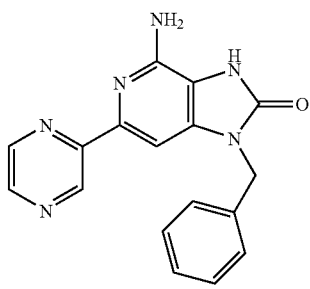

N-2,N-4-Dibenzyl-6-pyrazin-2-yl-pyridine-2,3,4-triamine (100 mgs/0.261 mmols) was dissolved in DMF (5 mls) and CDI (95.3 mgs/0.523 mmols) added, heated at 60° C. for 5 hours then concentrated in vacuo. The reaction mixure was then dissolved in conc. sulfuric acid (3 mls) and stirred at room temperature for 30 mins. Ice was then added ice to reaction and quenched by pouring onto $K_2CO_3$ (8 g) in water (5 mls). It was then extracted with EtOAc, dried over sodium sulphate and concentrated in vacuo. The residue was purified by column chromatography. More particularly, EtOAc then 95:5 EtOAc:MeOH was used to separate the two regioisomers to give the title compound (15 mgs) as a pale orange solid.

¹H NMR (CD3OD, 400 MHz) ☐ 5.10(s, 2H), 7.20-7.40 (m, 5H), 7.55 (s, 1H), 8.45 (s, 1H), 8.55 (d, 1H), 9.4 (s, 1H).

EXAMPLE 6

4-amino-1-benzyl-6-morpholin-4-ylmethyl-1,3-dihydro-imidazolo[4,5,c]pyridine-2-one

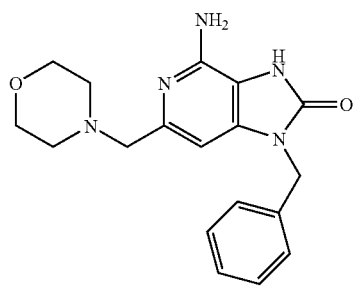

N-2,N-4-dibenzyl-6-morpholin-4-yl-methyl-pyridine-2,3,4-triamine (240 mg, 0.59 mmol) was dissolved in 20 mL of dichlororomethane then 1,1'-carbonyldiimidazole was added (91 mg, 1.77 mmol) and the reaction was stirred at room temperature for 48 hours. 20 mL of water was added and the organic layer was isolated, dried over magnesium sulfate and the solvent was removed in vacuo. The crude residue was purified by column chromatography on silica gel using 4% methanol in dichloromethane to give 140 mg of a mixture of 2 isomers. 60 mg of this mixture of the 2 isomers was dissolved in 2 mL of concentrated sulfuric acid and stirred at room temperature for 30 minutes. Water (5 mL) was carefully added followed by potassium carbonate (5.2 g until pH~7). The mixture was extracted with ethyl acetate, the organic layer was isolated, dried over magnesium sulfate and the solvent was removed in vacuo. The crude residue was purified by column chromatography on silica gel using 1% ammonia and 10% methanol in dichloromethane to give 10 mg of the title compound and 6 mg of the other isomer.

¹H NMR (CD₃OD): 7.38-7.2 (m, 5H), 6.58 (s, 1H), 5.05 (d, 2H), 3.65 (m, 4H), 3.4 (s, 2H), 2.4 (m, 4H). LRMS (ES⁺) m/z 340 [MH]⁺

EXAMPLE 7

4-amino-1-benzyl-2-oxo-2,3-dihydro-1H-imidazo[4,5,c]pyridine-7-carboxylic acid cyclopropylmethyl-amide

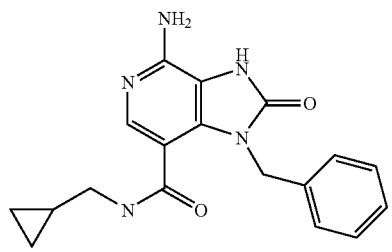

1-benzyl-4-dibenzylamino-2-oxo-2,3-dihydro-1H-imidazo[4,5,c]pyridine-7-carboxylic acid cyclopropylmethyl-amide (10 mg, 0.02 mmol) was dissolved in 1 mL of concentrated sulphuric acid and the mixture was stirred at room temperature for 30 minutes. Once completed, the mixture was diluted in 5 mL of water and potassium carbonate was added portion wise until pH~12. The mixture was then extracted with ethyl acetate (2×50 mL). The organic layers were combined, dried over MgSO4 and the solvent removed in vacuo. The residue was purified by column chromatography on silica gel using 20% of methanol in ethyl acetate to give 1 mg of the title compound.

LRMS (ES⁺) m/z 338 [MH]⁺

EXAMPLE 8

4-amino-1-benzyl-7-bromo-6-methyl-1,3-dihydro-imidazo[4,5,c]pyridine-2-one

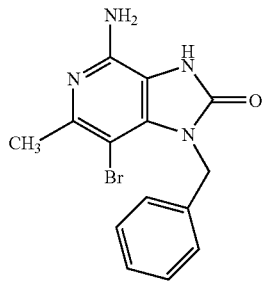

4-Amino-1-benzyl-6-methyl-1,3-dihydro-imidazo[4,5-c]pyridin-2-one (20 mg, 0.08 mmol) was suspended in 5 mL of acetic acid then sodium acetate (5 mg, 0.08 mmol) was added followed by bromine (4 □L, 0.08 mmol) dropwise. The mixture was stirred at room temperature for 30 minutes. The mixture was diluted in water (50 mL) and extracted with ethyl acetate (50 mL), the organic layer was separated, dried over magnesium sulfate and the solvent was removed in vacuo. The residue was purified by column chromatography on silica gel using 10% of methanol in ethyl acetate to give 15 mg of the title compound as a brown solid.

$^1$H NMR (d6 DMSO) □: 7.40-7.10 (m, 5H), 6.85 (s, 2H), 5.30 (s, 2H), 2.35 (s, 3H). LRMS (ES$^+$) m/z 333, 335 [MH]$^+$

EXAMPLE 9

4-amino-1-benzyl-6-methyl-5-oxy-1,3-dihydro-imidazo[4,5,c]pyridine-2-one

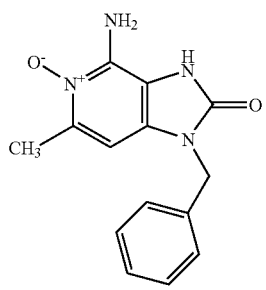

4-Amino-1-benzyl-6-methyl-1,3-dihydro-imidazo[4,5-c]pyridin-2-one (20 mg, 0.08 mmol) was dissolved in 10 mL of dichloromethane then 3-chloroperoxybenzoic acid (15 mg, 0.09 mmol) was added and the mixture stirred at room temperature for 2 hours. The mixture was washed with water, dried over magnesium sulfate and the solvent was removed in vacuo to give 5 mg of the title compound.

$^1$H NMR (CD3OD) □: 7.40-7.20 (m, 5H), 6.59 (s, 1H), 5.05 (s, 2H), 2.45 (s, 3H). LRMS (ES$^+$) m/z 271 [MH]$^+$

EXAMPLE 10

4-Amino-1-benzyl-6-(2-methoxy-ethyl)-1,3-dihydro-imidazo[4,5-c]pyridine-2-one

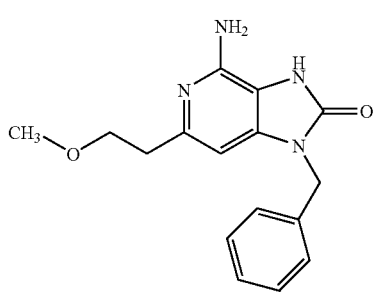

1-Benzyl-4-benzylamino-6-(2-methoxy-ethyl)-1,3-dihydro-imidazo[4,5-c]pyridine-2-one (32 mg, 0.082 mmol) was stirred in concentrated sulphuric acid (2 ml) for 30 minutes. Water (5 ml) was added and the mixture added drop-wise to a stirred solution of saturated NaHCO$_3$ to achieve a basic pH. The aqueous was extracted with 2×EtOAc and the combined organics dried and concentrated to afford a yellow solid. The mixture of isomers was separated by column chromatography on silica, eluting with DCM:MeOH, 97:3 with increasing gradient to DCM:MeOH:NH$_3$ 95:5:0.5 to afford the title compound as a pale yellow solid, (3.1 mg, 13%)

$^1$H NMR (MeOD) □ 2.82-2.85(t, 2H), 3.66-3.69(t, 2H), 5.08(s, 2H), 6.36(s, 1H), 7.19-7.34(m, 5H); LRMS (ES) m/z 299 [MH]$^+$

EXAMPLE 11

4-Amino-1-benzyl-6-[2-(2-methoxy-ethylamino)-ethyl]-1,3-dihydro-imidazo[4,5-c]pyridine-2-one

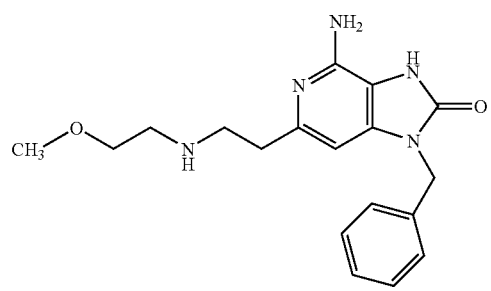

[2-(1-Benzyl-4-benzylamino-2-oxo-2,3-dihydro-1H-imidazo[4,5-c]pyridine-6-yl)-ethyl]-(2-methoxy-ethyl)-carbamic acid tert-butyl ester (64 mg, 0.12 mmol) was stirred in concentrated sulphuric acid (2 ml) for 30 minutes. Water (5 ml) was added and the mixture added drop-wise to a stirred solution of saturated NaHCO$_3$ to achieve a basic pH. The aqueous was extracted with 2×EtOAc and the combined organics dried and concentrated to afford a yellow solid. The mixture of isomers was separated by column chromatography on silica, eluting with DCM:MeOH, 98:2 with increasing gradient to DCM:MeOH:NH$_3$ 90:10:1 to afford the title compound as a yellow solid, (4.2 mg, 11%).

1H NMR (MeOD) ☐ 2.84-2.86 (t, 2H), 3.02-3.05(t, 2H), 3.27 (s, 3H), 3.45-3.48(t, 2H), 5.09(s, 2H), 6.34(s, 1H), 7.20-7.34(m, 5H); LRMS (ES) m/z 342 [MH]$^+$

EXAMPLE 12

4-Amino-1-benzyl-6-oxazol-2-yl-1,3-dihydro-imidazo[4,5-c]pyridin-2-one

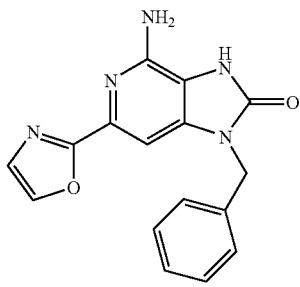

CDI (821 mg, 5.06 mmol) was added to a solution of N*2*, N*4*-Dibenzyl-6-oxazol-2-yl-pyridine-2,3,4-triamine (940 mg, 2.53 mmol) in THF (15 ml). The solution was heated at 60° C. for 18 hrs under nitrogen. The reaction mixture was allowed to cool then concentrated in vacuo. The crude mixture was then dissolved in concentrated H$_2$SO$_4$ (15 ml) and left for 30 minutes at room temperature. The dark brown solution was added drop-wise onto crushed ice. The pH was adjusted to ~9 by addition of a saturated aqueous solution of K$_2$CO$_3$ then the mixture was filtered. The solid was washed with EtOAc (200 ml) then the organic and aqueous filtrates were transferred to a separating funnel. The layers were separated and the aqueous was re-extracted with EtOAc (200 ml). The organics were combined, dried (MgSO$_4$) and evaporated to an orange gummy solid. The crude material was triturated with EtOAc and toluene. The solid obtained was filtered and washed with EtOAc to give an off-white solid. This material was purified by HPLC on a Phenomenex Gemini 5 µm column (150×21.2 mmid), eluted with 0.05% formic acid (aq) and 0.05% formic acid in MeCN at a flow rate of 15 ml/min. The gradient was isocratic at 5% organic for 0.6 minutes, then increased linearly from 5% to 80% organic over 12 minutes.

The filtrate from the trituration was evaporated then columned on Isco Companion on a silica column (12 g, Redisep). The resultant material was then eluted with EtOAc:MeOH, increasing the gradient linearly from 95:5 to 98:2 over 8 column volumes. The desired fractions were combined and evaporated to an orange gummy solid. This material was purified by HPLC as above. The desired fractions from both HPLC columns were combined and evaporated to yield the title compound as a white solid (26 mg, 3%).

$^1$H NMR (CD3OD) ☐ 5.07 (s, 2H) 7.17- 7.36 (m, 7H) 7.92 (s, 1H) LCMS R$_t$=2.15 m/z 308 [MH]$^+$

An alternative means of accessing Example 12 is described below.

4-Amino-1-benzyl-6-ozazol-2-yl-1,3-dihydro-imidazo[4,5-c]pyridin-2-one

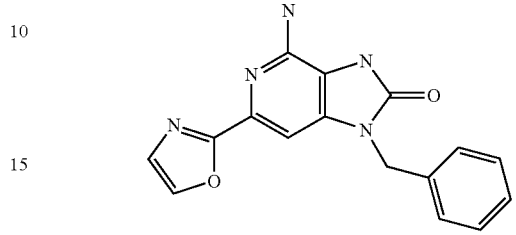

Butyl lithium solution in hexane (1.6M, 183 ul, 0.29 mmol) was added drop wise to a solution of oxazole (16 ul, 0.24 mmol) in THF (1 ml) at −78° C. under N$_2$. The solution was stirred at −78° C. for 10 minutes than a solution of zinc chloride (100 mg, 0.73 mmol) in THF (1 ml) was added drop wise. The solution was stirred at −78° C. for 15 minutes then allowed to warm to room temperature. The solution was then added via a syringe to a pre-sealed, nitrogen purged microwave vial (Biotage, 0.5-2.0 ml) containing 4-Amino-1-benzyl-6-bromo-1,3-dihydro-imidazo[4,5-c]pyridin-2-one (13 mg, 0.04 mmol) and palladium bis(triphenylphosphine) dichloride (12 mg, 0.02 mmol). The vial was heated under microwave irradiation (Biotage, Initiator 8) for 15 minutes at 110° C. The reaction mixture was partitioned between ethyl acetate (20 ml) and saturated NH$_4$Cl$_{(aq)}$ (10 ml). The mixture was filtered through celite, washing through with ethyl acetate (20 ml). The layers were separated and the organics were washed with water (10 ml) and brine (10 ml), dried over MgSO$_4$ and concentrated in vacuo to give the crude. The sample was dissolved in a mixture of acetonitrile:water: DMSO (2:1:1) and purified by preparative HPLC (Fraction-Lynx) to give the title compound (2 mg) as a white solid.

$^1$H NMR (d6-DMSO) ☐ 10.60 (brs, 1H), 8.10 (s, 1H), 7.36-7.27 (m, 6H), 7.19 (s, 1H), 6.01 (br s, 2H), 5.04 (s, 2H); LRMS (APCI and ES) m/z 308 [MH]$^+$.

EXAMPLE 13

4-Amino-1-benzyl-6-(1-methyl-1H-imidazol-2-yl)-1,3-dihydro-imidazo[4,5-c]pyridine-2-one

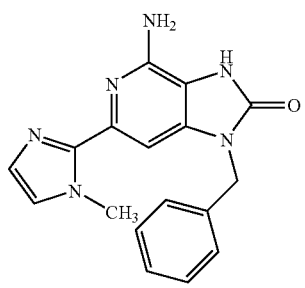

CDI (184 mg, 1.13 mmol) was added to a solution of the N*2*,N*4*-Dibenzyl-6-(1-methyl-1H-imidazol-2-yl)-pyridine-2,3,4-triamine (218 mg, 0.567 mmol) in DMF (3 ml) in a ReactiVial. The vial was flushed with nitrogen then sealed and heated in an aluminium block at 60° C. (block temperature). The dark brown solution was left to stir at this temperature for 16 hrs. The solution was concentrated under high-vacuum then dissolved in concentrated sulphuric acid (5 ml). The brown solution was left to stir at room temperature for 30 minutes then poured onto crushed ice (~20 ml). A saturated aqueous solution of potassium carbonate was added drop-wise until pH~8. The aqueous solution was decanted from the solid that had precipitated out during neutralisation, then extracted with EtOAc (2×50 ml). The combined organics were dried ($MgSO_4$) and evaporated to a yellow solid (106 mg).

A sample (58 mg) by HPLC on a Phenomenex Gemini 5 μm column (150×21.2 mmid). Eluted with 0.05% DEA (aq) and 0.05% DEA in MeCN at a flow rate of 18 ml/min. The gradient was isocratic at 5% organic for 0.6 minutes, then increased linearly from 5% to 100% organic over 15 minutes.

The desired fractions were combined and evaporated to yield the title compound as a white solid (10 mg, 6%). $^1$H NMR (CD3OD) ☐ 3.94 (s, 3H) 5.08 (s, 2H) 6.91-6.95 (m, 1H) 7.00 (s, 1H), 7.07-7.10 (m, 1H) 7.16-7.38 (m, 5H). LRMS ($ES^+$) m/z 321 $[MH]^+$

EXAMPLE 14

4-Amino-1-benzyl-6-(3-methyl-[1,2,4]oxadiazol-5-yl)-1,3-dihydro-imidazo[4,5-c]pyridin-2-one

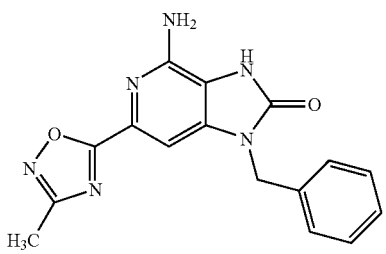

1-Benzyl-4-benzylamino-2-oxo-2,3-dihydro-1H-imidazo[4,5-c]pyridine-6-carboxylic acid (1-hydroxyimino-ethyl)-amide was suspended in toluene and sealed in a microwave vial (Biotage, 0.5-2.0 ml). The vial was sealed and heated under microwave irradiation (Biotage Initiator 8) for 15 minutes at 150° C. Sample heated in microwave for a further 30 minutes at 150° C., and again for a further 30 minutes at 150° C. The mixture was evaporated then partitioned between EtOAc (10 ml) and water (5 ml). The aqueous was extracted twice more with EtOAc (2×10 ml) then the combined organics were dried ($MgSO_4$) and evaporated. The residue was suspended in acetonitrile (2 ml) and this mixture was sealed in a microwave vial then heated under microwave irradiation for 30 minutes at 170° C., then at 190° C. for a further 30 minutes.

The reaction mixture was concentrated in vacuo then dissolved in concentrated $H_2SO_4$ (2 ml). The solution was left to stir for 30 minutes then poured onto crushed ice. A saturated aqueous $K_2CO_3$ solution was added drop-wise until pH was ~8. The aqueous was decanted from the solid into a separating funnel then extracted with EtOAc (3×15 ml). The combined organics were dried (MgSO4) and evaporated. The mixture of isomers was purified by HPLC on a Luna 10 micron C18(2) column (150×21.2 mmid). Eluted with 0.1% formic acid (aq) and 0.1% formic acid in MeCN at a flow rate of 25 ml/min. The gradient was isocratic at 5% organic for 0.6 minutes, then increased linearly from 5% to 90% organic over 8.50 minutes. The desired fractions were evaporated to give the title compound as a white solid (0.5 mg, 1%). LCMS $R_t$=2.46 m/z 323 $[MH]^+$

EXAMPLE 15

4-Amino-1-benzyl-6-trifluoromethyl-1,3-dihydro-imidazo[4,5-c]pyridine-2-one

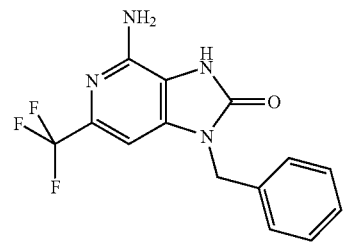

1-Benzyl-4-benzylamino-6-trifluoromethyl-1,3-dihydro-imidazo[4,5-c]pyridine-2-one (2.63 g, 6.60 mmol) was dissolved in c.$H_2SO_4$ (50 ml) and the reaction mixture was stirred at room temperature for 30 minutes. The reaction mixture was cooled to 0° C. and ice was added. $K_2CO_3$ (150 g) was dissolved in water (700 ml) and the reaction mixture was added dropwise. The aqueous was extracted with EtOAc (6×500 ml). The combined organics were washed with brine (200 ml), dried over $MgSO_4$ and concentrated in vacuo to give the title compound (1.20 g) as a white solid.

$^1$H NMR ($CDCl_3$) δ 10.77 (br s, 1H), 7.36-7.25 (m, 5H), 7.01 (s, 1H), 6.20 (br s, 2H), 5.04 (s, 2H); LRMS (APCI and ES) m/z 309 $[MH]^+$, 307 $[MH]^-$. Found C, 54.55; H, 3.60; N, 18.17%. $C_{14}H_{11}F_3N_4O$ requires % C, 54.36; H, 3.61; N, 17.86.

An alternative synthesis of Example 15 is described below;

Ethyl-[2,3-diamino-6-(trifluoromethyl)-pyridin-4-yl]-benzylcarbamate (35 gm, 99 mmol) was dissolved in glacial acetic acid (300 mL) at room temperature. Filtered to remove any insoluble material and then the clear yellow filtrate was heated with stirring to 80° C. Within 10 minutes a white precipitate began to form. Heating was continued for a total of 40 minutes. The reaction mixture was allowed to cool to ambient temperature and the precipitate was collected by filtration, washed with acetic acid and dried in vacuo at 50° C. for 3 hours to give the title compound (26.4 gm, 86% yield) as a white solid.

EXAMPLE 16

4-Amino-1-(6-methyl-pyridin-3-ylmethyl)-6-oxazol-2-yl-1,3-dihydro-imidazo[4,5-c]pyridine-2-one

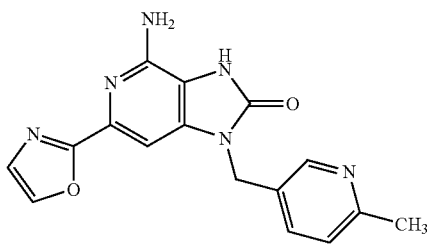

CDI (272 mg) was added to a solution of N2,N2-dibenzyl-N4-(6-methyl-pyridin-3-ylmethyl)-6-oxazol-2-yl-pyridine-2,3,4-triamine (400 mg) in THF (10 ml). The solution was left to stir under $N_2$ at 60° C. for 5 h. A further 3 equivalents of CDI (408 mg) were added and the reaction heated at reflux for 16 h. The reaction mixture was allowed to cool then concentrated in vacuo. The crude mixture was then dissolved in concentrated $H_2SO_4$ (5 ml) and left for 30 minutes at RT. The dark brown solution was added drop-wise onto crushed ice. The pH was adjusted to ~8 by addition of a saturated solution of $K_2CO_3$ then the mixture was filtered. The solid obtained was washed with EtOAc (50 ml) then the organic and aqueous filtrates were transferred to a separating funnel. The layers were separated and the aqueous was re-extracted with EtOAc (50 ml). The organics were combined, dried ($MgSO_4$) and evaporated to provide a gummy solid. This was triturated with $Et_2O$ and the solid collected by filtration and washed with $Et_2O$, giving the title compound as an off-white solid (30 mg). $^1$H NMR (CDCl$_3$, 400 MHz) □ 2.45 (s, 3H), 5.09 (s, 2H), 7.21-7.28 (m, 2H), 7.30 (s, 1H), 7.70 (dd, 1H), 7.95 (s, 1H), 8.42 (d, 1H). LCMS r$_t$=2.29 m/z 323 [MH]$^+$

EXAMPLE 17

4-Amino-1-benzyl-6-(2-methoxy-ethoxy)-1,3-dihydro-imidazo[4,5-c]pyridin-2-one

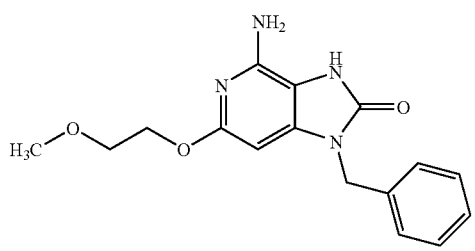

[2-Amino-6-(2-methoxy-ethoxy)-3-nitro-pyridin-4-yl]-benzyl-carbamic acid ethyl ester (118 mg) was dissolved in ethanol (5 ml) and 10% Pd on carbon (15 mg) added. The reaction was stirred under a hydrogen atmosphere (50 psi) for 1 h at RT. The reaction mixture was then filtered through a Celite pad and evaporated. The crude was dissolved in glacial acetic acid (2 ml) and transferred to a microwave vial (Biotage, 0.5-2.0 ml). The vial was sealed and heated under microwave irradiation at 100° C. for 5 minutes. The resultant brown mixture was evaporated then solid loaded on silica and columned on Isco Companion on a silica column (4 g, Redisep), eluting with EtOAc:heptane, increasing the gradient linearly from 60:40 to 100% EtOAc over 8 column volumes (CVs) then isocratic at 100% EtOAc for 8 CVs. The desired fractions were combined and evaporated to provide the title compound as a white solid (50 mg).

$^1$H NMR (CDCl$_3$, 400 MHz) □ 3.35 (s, 3H), 3.62 (t, 2H), 4.20 (t, 2H), 4.95 (s, 2H), 5.80 (s, 1H), 7.20-7.38 (m, 5H). LCMS R$_t$=2.13 m/z 315 [MH]$^+$

EXAMPLE 18

4-Amino-1-(6-methyl-pyridin-3-ylmethyl)-6-trifluoromethyl-1,3-dihydro-imidazo[4,5-c]pyridine-2-one

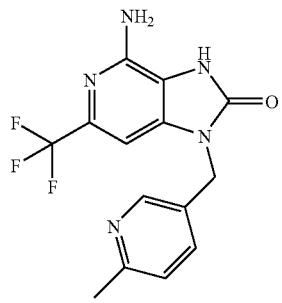

(2-Amino-3-nitro-6-trifluoromethyl-pyridin-4-yl)-(6-methyl-pyridin-3-ylmethyl)-carbamic acid ethyl ester (27 mg, 0.07 mmol) was stirred in glacial acetic acid (5 ml) and the solution stirred at ambient temperature, 40 psi H$_2$, in the presence of 10% Pd/C (5.4 mg, 20% wt) for 4 h. The suspension was filtered through an Arbocel pad, washed with 2×3 ml AcOH and the filtrate concentrated in vacuo. Acetonitrile (5 ml) was added to the residue and the material triturated, the resulting solid removed by filtration and dried in vacuo to afford 10.6 mg of the title compound as a white solid. $^1$H NMR (d6-DMSO): δ 8.45(s, 1H), 7.57-7.55(d, 1H), 7.20-7.18(d, 1H), 7.10(s, 1H), 6.20(bs, 2H), 5.01(s, 2H), 2.40(s, 3H); LRMS (APCI) m/z 324 [MH]$^+$ An alternative means of accessing Example 18 is described below.

4-amino-1-(6-methyl-pyridyin-3-ylmethyl)-6-trifluoromethyl-1,3-dihydro-imidazo(4,5-c)pyridine-2-one

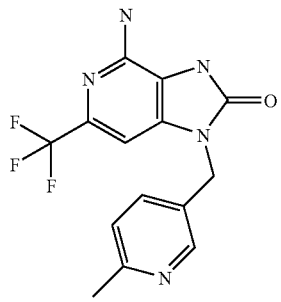

4-benzylamino-1-(6-methyl-pyridyin-3-ylmethyl)-6-trifluoromethyl-1,3-dihydro-imidazo(4,5-c)pyridine-2-one (30 mg, 0.07 mmol) was dissolved in 1 mL of concentrated sulfuric acid and the reaction mixture was stirred at room temperature for 1 h. The mixture was poured into water (100 mL) and potassium carbonate was added portionwise until pH~basic. It was then extracted with ethyl acetate (100 mL). The organic layer was separated, dried over magnesium sulfate and the solvent was removed in vacuo to give 16 mg of the title compound as a white solid. 1H NMR (d6-DMSO): δ 8.45(s, 1H), 7.57-7.55(d, 1H), 7.20-7.18(d, 1H), 7.10(s, 1H), 6.20 (bs, 2H), 5.01 (s, 2H), 2.40(s, 3H); LRMS (APCI) m/z 324 [MH]⁺

EXAMPLE 19

4-Amino-6-(4-methyl-oxazol-2-yl)-1-(6-methyl-pyridin-3-ylmethyl)-1,3-dihydro-imidazo[4,5c]pyridine-2-one

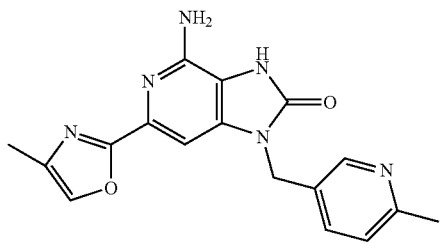

A mixture of Raney nickel (5 mg) and [2-amino-6-(4-methyl-oxazol-2-yl)-3-nitro-pyridin-4-yl]-(6-methyl-pyridin-3-ylmethyl)-carbamic acid ethyl ester (69 mg) in acetic acid (3 ml) was stirred under a hydrogen atmosphere (80 psi) for 1 hour. Arobcel was added onto the top of a sulphonic acid cation-exchange cartridge (Bakerbond, 1 g), and the reaction mixture loaded onto the top and allowed to filter through. The catalyst and Arbocel were removed with a spatula then the cartridge was washed with methanol (5 ml) to remove impurities. The product was released from the cartridge by eluting with methanolic ammonia (2M, 2×5 ml). The crude solution was evaporated, and then IPA (3 ml) was added, causing precipitation of solids that were collected by filtration and washed with IPA. The off-white solid obtained was dried under high-vacuum to provide the title compound (16 mg). 1H NMR (400 MHz, DMSO-d₆) δ ppm 2.13 (s, 3 H) 2.42 (s, 3 H) 5.05 (s, 2 H) 5.98 (s, 2 H) 7.21 (d, J=7.90 Hz, 1 H) 7.25 (s, 1 H) 7.56 (dd, J=7.90, 2.44 Hz, 1 H) 7.80 (s, 1 H) 8.47 (d, J=2.44 Hz, 1 H) 10.68 (br. s., 1 H), LRMS (ESI) m/z 337 [MH]⁺, 335 [MH]⁻

EXAMPLE 20

4-Amino-6-(4-ethyl-oxazol-2-yl)-1-(6-methyl-pyridin-3-ylmethyl)-1,3-dihydro-imidazo[4,5-c]pyridin-2-one

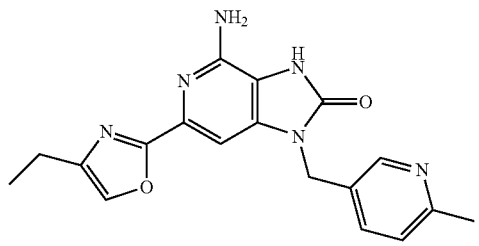

[2-amino-6-(4-ethyl-oxazol-2-yl)-3-nitro-pyridin-4-yl]-(6-methyl-pyridin-3-ylmethyl)-carbamic acid ethyl ester (74 mg) was dissolved in acetic acid (2 ml) and zinc powder (113 mg, Aldrich, 99%) was added to the reaction. The mixture was left to stir at room temperature under nitrogen for 16 hours. The reaction mixture was filtered directly onto a cation exchange cartridge (Bakerbond SCX, sulphonic acid bonded-phase, 1 g). The SCX cartridge was washed with methanol (2×4 ml) to remove impurities, then the product released with ammonia in methanol (2 M, 4 ml). The desired fractions were combined and evaporated to an off-white solid that was triturated with isopropanol, filtered, and then washed with isopropanol, providing the title compound (32 mg) as a white solid. 1H NMR (400 MHz, DMSO-d₆) δ ppm 1.16 (t, J=7.42 Hz, 3 H) 2.40 (s, 3 H) 2.44-2.56 (m, 2 H) 5.04 (s, 2 H) 5.98 (s, 2 H) 7.19 (d, J=8.02 Hz, 1 H) 7.23 (s, 1 H) 7.54 (dd, J=8.02, 2.34 Hz, 1 H) 7.79 (s, 1 H) 8.45 (d, J=2.34 Hz, 1 H) 10.65 (s, 1 H), LCMS R₁=1.73 m/z 351 [MH]⁺

EXAMPLE 21

4-Amino-1-benzyl-6-(1H-imidazol-2-yl)-1,3-dihydro-imidazo[4,5-c]pyridin-2-one

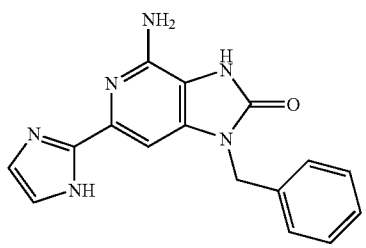

The title compound was prepared following the method of Example 20 using {2-amino-3-nitro-6-[1-(2-trimethylsilanyl-ethoxymethyl)-1H-imidazol-2-yl]-pyridin-4-yl}-benzyl-carbamic acid ethyl ester (174 mg) and Raney nickel (5 mg) in acetic acid (3 ml). This gave initially the SEM protected imidazole compound. Hydrogen chloride in dioxane (4 M, 1 ml) was then added drop-wise and the solution left to stir at room temperature for 24 hours. The reaction mixture was then transferred to a microwave vial (Biotage, 2-5 ml) and heated under microwave irradiation for 10 minutes at 110° C. (Biotage, Initiator 8). The reaction mixture was evaporated then re-dissolved in methanol and the solution loaded onto a cation-exchange cartridge (Bakerbond, sulphonic acid bonded-phase, 1 g). The cartridge was washed with methanol (2×5 ml) to remove impurities and then the product released by eluting with ammonia in methanol (2 M, 5 ml). The desired fractions were combined and evaporated to a brown solid. This was triturated with isopropanol and the solid collected by filtration then washed with more isopropanol, providing the title compound (28 mg) as a pale brown solid. 1H NMR (400 MHz, DMSO-$d_6$) δ ppm 5.02 (s, 2 H) 5.58 (s, 2 H) 6.91 (s, 1 H) 7.06 (s, 1 H) 7.11 (s, 1 H) 7.25-7.36 (m, 5 H) 10.53 (s, 1 H) 11.99 (s, 1 H). LCMS $R_t$=1.52 m/z 307 [MH]$^+$hm

EXAMPLE 22

4-Amino-1-benzyl-6-(2-fluoro-phenyl)-1,3-dihydro-imidazo[4,5-c]pyridin-2-one

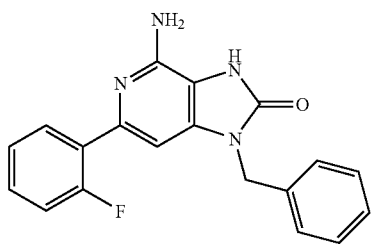

[2-Amino-6-(2-fluoro-phenyl)-3-nitro-pyridin-4-yl]-benzyl-carbamic acid ethyl ester (31 mg) was dissolved in acetic acid (1 ml). Zinc powder (Aldrich, 99%, 20 mg) was added and the mixture left to stir at room temperature under nitrogen for 2 hours. Additional zinc powder (30 mg) was added and mixture left to stir for a further 1 hour. The reaction mixture was diluted with methanol (2 ml) then filtered directly onto a cation exchange cartridge (Bakerbond SCX, sulphonic acid bonded-phase, 1 g). The SCX cartridge was washed with methanol (2×5 ml) to remove impurities and then the product was released with ammonia in methanol (2 M, 5 ml). The desired fraction was evaporated to a pale brown solid. This was triturated with ethyl acetate then filtered and washed with more ethyl acetate to yield the title compound (8 mg) as a pale purple solid. 1H NMR (400 MHz, DMSO-$d_6$) δ ppm 4.99 (s, 2 H) 5.82 (s, 2 H) 6.87 (d, J=1.95 Hz, 1 H) 7.15-7.29 (m, 3 H) 7.29-7.39 (m, 5 H) 7.81 (td, J=8.01, 1.95 Hz, 1 H) 10.51 (s, 1 H), LCMS $R_t$=2.21 m/z 335 [MH]$^+$ The following examples 23 to 119 can be or were prepared in an analogous manner to Examples 1-22 from analogous intermediates described within the Preparation section using analogous chemistry.

Examples 23-28 were prepared following the method of Example 1, Examples 54-60, 65-72 and 107-110 were all prepared following the method described for Examples 15 and 18, Examples 31 and 61 were prepared following the method described for Example 3, Examples 42-49, 83-95 and 101-102 were all prepared following the method described for Example 17, Examples 73-78, 96-99, 103-106 and 111-112 were all prepared following the method described for Example 19, Examples 79-81 were prepared following the method described for Example 22, Examples 34-35 and 40 were prepared following the method described for Example 6, Examples 29-30, 36-39, 41 and 50-53 were prepared following the method described for Example 4, Examples 32-33 were prepared following the method described for Example 5 was prepared following the method described for Example 14.

Examples 62-64 can be prepared following the method described for Examples 15 and 18, example 82 can be prepared following the method described for Example 14 and example 100 can be prepared following the method described for Example 17.

In the following table of examples, the asterisk indicates the point of attachment.

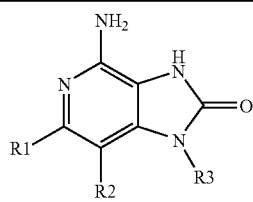

| Example No. | R1 | R2 | R3 | Data |
|---|---|---|---|---|
| 23 | n-propyl | H | Bn | $^1$HNMR(CD$_3$OD) δ 0.88(t, 3H), 1.61(m, 2H), 2.51(t, 2H), 5.01(s, 2H), 6.34(s, 1H), 7.30(m, 5H). |
| 24 | iso-propyl | H | Bn | $^1$HNMR(CD$_3$OD) δ 1.16-1.18(d, 6H), 2.77-2.83(m, 1H), 5.02(s, 2H), 6.34(s, 1H), 7.28-7.33(m, 5H). |

-continued

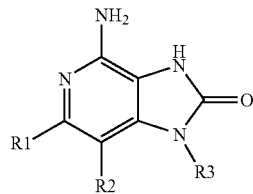

| Example No. | R1 | R2 | R3 | Data |
|---|---|---|---|---|
| 25 | Me | H | *-CH2-C6H4-CF3 (meta) | $^1$HNMR(d6-DMSO) δ 10.29(s, 1H), 7.64(m, 4H), 6.39(s, 1H), 5.59(s, 2H), 5.02(s, 2H), 2.21(s, 3H). |
| 26 | Me | H | *-CH2-C6H4-F (para) | $^1$HNMR(d6-DMSO) δ 10.24(br s, 1H), 7.34(m, 2H), 7.15(m, 2H), 6.35(s, 1H), 6.55(s, 2H), 4.89(s, 2H), 2.21(s, 3H). LRMS (ES) m/z 272 [MH]+. |
| 27 | Me | H | *-CH2-C6H4-F (meta) | $^1$HNMR(CD3OD) δ 7.32(m, 1H), 7.08(d, 1H), 6.98(m, 2H), 6.34(s, 1H) 4.98(s, 2H), 2.28(s, 3H). |
| 28 | Me | H | *-CH2-C6H4-F (ortho) | $^1$HNMR(d6-DMSO) δ 10.28(s, 1H), 7.37 to 7.14(m, 4H), 6.27(s, 1H) 6.58(s, 2H) 4.96(s, 2H) 2.21(s, 3H). |
| 29 | HO-C(O)-* | H | Bn | $^1$H NMR(d6-DMSO, 400 MHz) δ 5.00(s, 2H), 7.20-7.45(m, 6H), 10.22(s, 1H). |
| 30 | cyclopropyl-CH2-NH-C(O)-* | H | Bn | $^1$H NMR(CDCl3, 400 MHz) δ 0.82(q, 2H), 0.92(q, 2H), 1.90(m, 1H), 4.25(t, 1H), 4.98(s, 2H), 5.40(t, 1H), 7.10-7.50(m, 6H). |
| 31 | —CH2CH2CH2— (R$^1$ + R$^2$) | | Bn | $^1$H NMR(CD3OD, 400 MHz) δ 2.00(m, 2H), 2.75(m, 4H), 5.13(s, 2H), 7.17(d, 2H), 7.32(m, 3H). |
| 32 | 2-pyridyl-* | H | Bn | $^1$HNMR(CD3OD) δ 5.10(s, 2H), 7.20-7.40(mult, 6H), 7.45(s, 1H), 7.80-7.85(dd, 1H), 8.20(d, 1H), 8.30(s, 1H), 8.55(d, 1H). |
| 33 | 2-pyrimidinyl-* | H | Bn | $^1$HNMR(d6-DMSO) δ 5.05(s, 2H), 5.90(s, 2H), 7.20-7.40(mult, 6H), 7.50(s, 1H), 8.80(d, 2H). |
| 34 | CH3-O-CH2CH2-NH-CH2-* | H | Bn | $^1$HNMR(CD3OD) δ 2.82(t, 2H), 3.35(s, 3H), 3.50(t, 2H), 3.75(s, 2H), 5.02(s, 2H), 6.55(s, 1H), 7.40-7.20(m, 5H). |

-continued

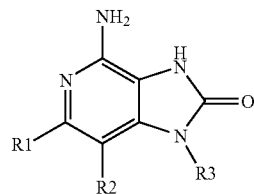

| Example No. | R1 | R2 | R3 | Data |
|---|---|---|---|---|
| 35 | *-CH2-N(piperazine)-N-CH3 | H | Bn | $^1$HNMR(CD$_3$OD) δ 2.30(s, 3H), 2.35-2.65(m, 8H), 5.10(s, 2H), 6.50(s, 1H), 7.05(s, 2H), 7.18-7.38(m, 5H), 7.65(s, 1H). |
| 36 | CH$_3$-C(=O)-* | H | Bn | $^1$HNMR(d6-DMSO) δ 10.75(s broad, 1H), 7.40-7.20(m, 5H), 5.90(s, 2H), 5.01(s, 2H), 3.25(s, 3H). |
| 37 | Et | H | Bn | $^1$HNMR(d6-DMSO) δ 10.25(s, 1H), 7.35-7.20(m, 5H), 6.30(s, 1H), 5.55(s, 2H), 4.90(s, 2H), 2.45(q, 2H), 1.10(t, 3H). |
| 38 | CF2H | H | Bn | $^1$HNMR(d6-DMSO) δ 10.65 (s broad, 1H), 7.40-7.20(m, 5H), 6.79(s, 1H), 6.75-6.40(t, 1H), 5.75(s, 2H), 4.98(s, 2H). |
| 39 | NC | H | Bn | $^1$HNMR(d6-DMSO) δ 7.40-7.20(m, 5H), 6.30(s, 1H), 4.95(s, 2H). |
| 40 | MeOCH$_2$— | H | Bn | $^1$HNMR(CD$_3$OD) δ 7.4-7.2(m, 5H), 6.55(s, 1H), 5.05(s, 2H), 4.30(s, 2H), 3.35(s, 3H). |
| 41 | H$_2$N-C(=O)-* | H | Bn | $^1$HNMR(d6 DMSO) δ 10.7(s, 1H), 7.5(s broad, 1H), 7.4-7.2(m, 5H), 7.10(s, 1H), 5.80(s, 2H), 5.0(s, 2H). |
| 42 | MeO | H | Bn | 1H NMR(400 MHz, DMSO-d$_6$) δ ppm 3.67(s, 3H) 4.88(s, 2H) 5.60(s, 2H) 5.81(s, 1H) 7.21-7.37(m, 5H) 10.09(s, 1H), LCMS R$_t$= 2.06 m/z 271 [MH]$^+$ |
| 43 | EtO | H | Bn | 1H NMR(400 MHz, DMSO-d$_6$) δ ppm 1.21(t, J=7.03 Hz, 3H) 4.10(q, J=7.03 Hz, 2H) 4.86(s, 2H) 5.56(s, 2H) 5.78(s, 1H) 7.16-7.38(m, 5H) 10.07(s, 1H), LCMS R$_t$=2.18 m/z 285 [MH]$^+$ |
| 44 | PrO | H | Bn | 1H NMR(400 MHz, DMSO-d$_6$) δ ppm 0.90(t, J=7.42 Hz, 3H) 1.56-1.71(m, 2H) 4.00(t, J=6.84 Hz, 2H) 4.87(s, 2H) 5.56(s, 2H) 5.80(s, 1H) 7.20-7.37(m, 5H) 10.07(s, 1H), LCMS R$_t$=2.35 m/z 299 [MH]$^+$ |
| 45 | MeHN | H | Bn | 1H NMR(400 MHz, DMSO-d$_6$) δ ppm 2.60(d, J=4.63 Hz, 3H) 4.83(s, 2H) 5.26(s, 2H) 5.41(s, 1H) 5.47(q, J=4.63 Hz, 1H) 7.21-7.28(m, 3H) 7.29-7.35(m, 2H) 9.81(s, 1H), LCMS R$_t$=1.59 m/z 270 [MH]$^+$ |

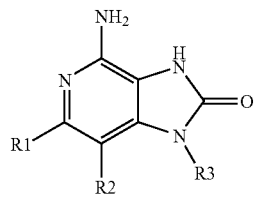

| Example No. | R1 | R2 | R3 | Data |
|---|---|---|---|---|
| 46 | EtHN | H | Bn | 1H NMR(400 MHz, DMSO-d$_6$) δ ppm 1.03(t, J=7.03 Hz, 3H) 2.99-3.11(m, 2H) 4.82(s, 2H) 5.23(s, 2H) 5.35-5.45(m, 2H) 7.21-7.28(m, 3H) 7.29-7.35(m, 2H) 9.80(s, 1H), LCMS R$_t$=1.69 m/z 284 [MH]$^+$ |
| 47 | PrHN | H | Bn | 1H NMR(400 MHz, DMSO-d$_6$) δ ppm 0.85(t, J=7.23 Hz, 3H) 1.35-1.50(m, 2H) 2.92-3.06(m, 2H) 4.81(s, 2H) 5.30(s, 2H) 5.39-5.46(m, 2H) 7.21-7.28(m, 3H) 7.29-7.35(m, 2H) 9.94(s, 1H), LCMS R$_t$ = 1.79 m/z 298 [MH]$^+$ |
| 48 | BuHN | H | Bn | 1H NMR(400 MHz, DMSO-d$_6$) δ ppm 0.86(t, J=7.42 Hz, 3H) 1.22-1.35(m, 2H) 1.36-1.47(m, 2H) 2.96-3.07(m, 2H) 4.82(s, 2H) 5.21(s, 2H) 5.35-5.47(m, 2H) 7.21-7.28(m, 3H) 7.29-7.38(m, 2H) 9.79(s, 1H), LCMS R$_t$=1.89 m/z 312 [MH]$^+$ |
| 49 | MeOCH$_2$CH$_2$HN | H | Bn | 1H NMR(400 MHz, DMSO-d$_6$) δ ppm 3.2-3.4(m, 5H), 3.5(m, 2H), 4.95(s, 2H), 5.60(s, 1H), 7.20-7.35(m, 5H). |
| 50 | H | H | Bn | $^1$HNMR(d6-DMSO) δ 10.4 (s broad, 1H), 7.55(d, 1H), 7.4-7.2(m, 5H), 6.45(d, 1H), 5.61(s, 2H), 4.9(s, 2H). |
| 51 | Me | H | isobutyl* | $^1$H NMR(d6-DMSO) δ 0.80-0.82(d, 6H), 1.96-2.04(m, 1H), 2.20(s, 3H), 3.43-3.45(d, 2H), 5.47(s, 2H), 6.34(s, 1H), 10.05(s, 1H). |
| 52 | Me | H | Phenyl | $^1$H NMR(CD3OD) δ 0.45-0.55(d, 6H), 1.40-1.55(m, 1H), 2.05-2.10(s, 3H), 3.15-3.20(d, 2H), 7.30(m, 2H), 7.40-7.50(m, 3H) |
| 53 | H | CH$_2$C(O)OCH$_3$* | Bn | $^1$HNMR(CD$_3$OD) δ 8.15(s, 1H), 7.25-7.15(m, 3H), 7.05(m, 2H), 5.55(s, 2H), 3.7(s, 2H), 3.3(s, 3H). |
| 54 | CF$_3$ | H | 4-fluorobenzyl* | $^1$HNMR(d6-DMSO) δ 5.00(s, 2H), 6.18(bs, 2H), 7.05(s, 1H), 7.13-7.17(m, 2H), 7.33-7.37(m, 2H). |

-continued

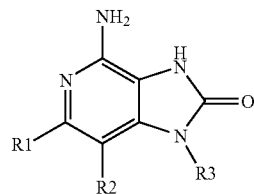

| Example No. | R1 | R2 | R3 | Data |
|---|---|---|---|---|
| 55 | CF$_3$ | H | *–CH$_2$CH$_2$–O–CH$_3$ | $^1$HNMR(d6-DMSO) δ 3.27(s, 3H), 3.53-3.56(t, 2H), 3.94-3.96(t, 2H), 6.13(bs, 2H), 7.07(s, 1H), 10.63(bs, 1H). |
| 56 | CF$_3$ | H | *–CH$_2$–(tetrahydropyran-3-yl) | $^1$HNMR(d6-DMSO) δ 1.20-1.98(m, 5H), 3.14-3.35(m, 2H), 3.62-3.68(m, 4H), 6.15(bs, 2H), 7.11(s, 1H), 10.62(bs, 1H). |
| 57 | CF$_3$ | H | *–CH$_2$–(6-hydroxypyridin-3-yl) | $^1$H NMR(d6-DMSO) □ 11.49(br s, 1H), 10.74(br s, 1H), 7.53(s, 1H), 7.40(dd, 1H), 7.22(s, 1H), 6.29(d, 1H), 6.18(br s, 2H), 4.76(s, 2H). |
| 58 | CF$_3$ | H | *–CH$_2$–(6-trifluoromethylpyridin-3-yl) | $^1$H NMR(DMSO): δ 8.77(s, 1H), 7.94-7.91(d, 1H), 7.87-7.85(d, 1H), 7.20(s, 1H), 6.22(s, 2H), 5.19(s, 2H). |
| 59 | CF$_3$ | H | *–CH$_2$–(2-methylthiazol-4-yl) | 1H NMR(d-Acetone): δ 7.24(s, 1H), 7.05(s, 1H), 5.62(bs, 1H), 5.10(s, 2H), 2.59(s, 3H). |
| 60 | CF$_3$ | H | *–CH$_2$–(6-chloropyridin-3-yl) | $^1$H NMR(d6-DMSO) δ 10.79(br s, 1H), 8.45(d, 1H), 7.76(dd, 1H), 7.49(d, 1H), 7.18(s, 1H), 6.21(br s, 2H), 5.08(s, 2H). |
| 61 | Me | Me | *–CH$_2$–(4-fluorophenyl) | $^1$HNMR(DMSO) δ 1.99(s, 3H), 2.17(s, 3H), 5.14(s, 2H), 5.48(bs, 2H), 7.10-7.17(m, 4H), 10.49(bs, 1H). |
| 62 | CF$_3$ | H | *–CH$_2$–(2-methylpyrimidin-5-yl) | |
| 63 | CF$_3$ | H | *–CH$_2$–(6-methylpyridazin-3-yl) | |
| 64 | CF$_3$ | H | *–CH$_2$–(5-methylpyrazin-2-yl) | |
| 65 | CF$_3$ | H | *–CH$_2$–(pyridin-2-yl) | $^1$H NMR(d-Acetone): δ 8.48(s, 1H), 7.75-7.72(m, 1H), 7.32-7.25(m, 2H), 6.95(s, 1H), 5.64(bs, 1H), 5.16(s, 2H). |

-continued

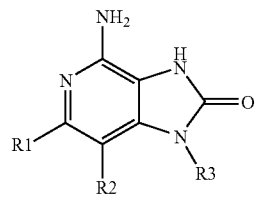

| Example No. | R1 | R2 | R3 | Data |
|---|---|---|---|---|
| 66 | CF₃ | H | *-CH₂-(3-pyridyl) | ¹H NMR(DMSO): δ 8.57(s, 1H), 8.47-8.46(d, 1H), 7.66-7.60(d, 1H), 7.36-7.33(qt, 1H), 7.13(s, 1H), 6.20(bs, 2H), 5.07(s, 2H). |
| 67 | CF₃ | H | *-CH₂-(4-pyridyl) | ¹H NMR(DMSO): δ 8.69-8.67(d, 2H), 7.67-7.65(d, 2H), 7.04(s, 1H), 5.32(s, 2H). |
| 68 | CF₃ | H | *-CH₂-(6-methoxy-3-pyridyl) | ¹H NMR(d6-DMSO) □ 10.78(br s, 1H), 8.23(d, 1H), 7.65(dd, 1H), 7.17(s, 1H), 7.78(d, 1H), 6.21(br s, 2H), 4.98(s, 2H), 3.81(s, 3H). |
| 69 | CF₃ | H | *-CH₂-(3-bromophenyl) | ¹H NMR(d6-DMSO) δ 10.79(br s, 1H), 7.55(s, 1H), 7.49-7.47(m, 1H), 7.31-7.29(m, 2H), 7.11(s, 1H), 6.22(br s, 2H), 5.04(s, 2H). |
| 70 | CF₃ | H | *-CH₂-(4-bromophenyl) | ¹H NMR(d6-DMSO) δ 10.79(br s, 1H), 7.54(d, 2H), 7.26(d, 2H), 7.06(s, 1H), 6.22(br s, 2H), 5.02(s, 2H). |
| 71 | CF₃ | H | *-CH₂-(3-cyanophenyl) | RMS (ES⁺) m/z 332 (MH⁻). LCMS (acid-combo): t = 2.94, ES⁺ 334 (MH⁺), ES⁻ 332 (MH⁻) |
| 72 | CF₃ | H | *-CH₂-(tetrahydrofuran-2-yl) | 1H NMR(d4-methanol): δ 7.11(s, 1H), 4.25-4.19(m, 1H), 3.99-3.89(m, 2H), 3.82-3.77(m, 1H), 3.73-3.67(m, 1H), 2.09-2.00(m, 1H), 1.91-1.84(m, 2H), 1.76-1.67(m, 1H). |
| 73 | CF₃ | H | *-CH₂-(4-cyanophenyl) | ¹H NMR(d6-DMSO) δ 10.82(br s, 1H), 7.81(d, 2H), 7.46(d, 2H), 7.08(s, 1H), 6.23(br s, 2H), 5.15(s, 2H). |
| 74 | 4,5-dimethyloxazol-2-yl | H | *-CH₂-(6-methyl-3-pyridyl) | ¹H NMR(400 MHz, DMSO-d₆) δ ppm 2.05(s, 3H) 2.27(s, 3H) 2.42(s, 3H) 5.04(s, 2H), 5.98(s, 2H) 7.18-7.23(m, 2H) 7.55(dd, J=7.80, 2.15 Hz, 1H) 8.46(d, J=2.15 Hz, 1H) 10.64(br. s., 1H), LCMS Rf= 1.62 m/z 351 [MH]⁺ |

-continued

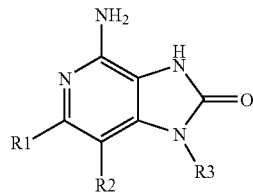

| Example No. | R1 | R2 | R3 | Data |
|---|---|---|---|---|
| 75 | 5-ethyl-oxazol-2-yl (*) | H | (5-methylpyridin-2-yl)methyl* | ¹H NMR(400 MHz, DMSO-d₆) δ ppm 1.21(t, J=7.58 Hz, 3H) 2.42(s, 3H) 2.71(q, J=7.58 Hz, 2H) 5.04(s, 2H) 6.00(s, 2H) 6.92(s, 1H) 7.20-7.22(m, 2H) 7.56(dd, J=7.80, 2.34 Hz, 1H) 8.46(d, J=2.34 Hz, 1H) 10.65(br. s., 1H), LCMS R$_t$= 1.68 m/z 351 [MH]⁺ |
| 76 | 4-isopropyl-oxazol-2-yl (*) | H | (5-methylpyridin-2-yl)methyl* | 1H NMR(400 MHz, DMSO-d₆) δ ppm 1.21(d, J=7.03 Hz, 6H) 2.42(s, 3H) 2.75-2.87(m, 1H) 5.06(s, 2H) 6.01(s, 2H) 7.21(d, J=7.92 Hz, 1H) 7.23(s, 1H) 7.55(dd, J=7.92, 2.25 Hz, 1H) 7.79(d, J=1.17 Hz, 1H) 8.46(d, J=2.25 Hz, 1H) 10.68(s, 1H), LCMS R$_t$=1.89 m/z 365 [MH]⁺ |
| 77 | 5-isopropyl-oxazol-2-yl (*) | H | (5-methylpyridin-2-yl)methyl* | 1H NMR(400 MHz, DMSO-d₆) δ ppm 1.24(d, J=7.03 Hz, 6H) 2.41(s, 3H) 2.97-3.07(m, 1H) 5.03(s, 2H) 6.00(s, 2H) 6.90(s, 1H) 7.19-7.22(m, 2H) 7.56(dd, J=7.81, 2.34 Hz, 1H) 8.46(d, J=2.34 Hz, 1H) 10.65(br. s., 1H), LCMS R$_t$= 1.84 m/z 365 [MH]⁺ |
| 78 | oxazol-5-yl (*) | H | (5-methylpyridin-2-yl)methyl* | ¹H NMR(D6-DMSO, 400 MHz) δ 2.40(s, 3H), 5.00(s, 2H), 5.85-5.95(br s, 2H), 6.95-7.00(s, 1H), 7.20(d, 1H), 7.40(s, 1H); 7.55-7.60(d, 1H), 8.35(s/1H), 8.45(s/1H), 10.55(s/1H). |
| 79 | thiazol-2-yl (*) | H | (5-methylpyridin-2-yl)methyl* | 1H NMR(400 MHz, DMSO-d₆) δ ppm 2.42(s, 3H) 5.05(s, 2H) 5.96(s, 2H) 7.21(d, J=8.20 Hz, 1H) 7.31(s, 1H) 7.58(dd, J=8.20, 2.15 Hz, 1H) 7.66(d, J=3.12 Hz, 1H) 7.82(d, J=3.12 Hz, 1H) 8.47(d, J=2.15 Hz, 1H) 10.66(s, 1H). |
| 80 | 3-fluorophenyl (*) | H | Bn | 1H NMR(400 MHz, DMSO-d₆) δ ppm 5.03(s, 2H) 5.82(s, 2H) 7.09-7.15(m, 1H) 7.19-7.28(m, 2H) 7.31-7.38(m, 4H) 7.40-7.46(m, 1H) 7.74-7.80(m, 2H) 10.46(s, 1H), LCMS R$_t$= 2.19 m/z 335 [MH]⁺ |

-continued

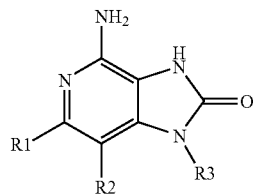

| Example No. | R1 | R2 | R3 | Data |
|---|---|---|---|---|
| 81 | 4-fluorophenyl* | H | Bn | 1H NMR(400 MHz, DMSO-d₆) δ ppm 3.30(s, 3H) 5.02(s, 2H) 5.68-5.80(m, 2H) 7.12(s, 1H) 7.17-7.29(m, 2H) 7.30-7.40(m, 3H) 7.87-7.99(m, 1H) 10.44(s, 1H), LCMS R$_t$=2.07 m/z 335 [MH]⁺ |
| 82 | 1,3,4-oxadiazol-2-yl* | H | (6-methylpyridin-3-yl)methyl* | |
| 83 | 1H-pyrazol-1-yl* | H | Bn | ¹H NMR((CD₃)₂SO) δ 5.00(s, 2H), 5.95(s, 2H), 6.40(s, 2H), 6.95(s, 1H), 7.20-7.30(m, 5H), 7.60(s, 1H), 8.30(s, 1H). LRMS (ES⁺) m/z 307 (MH⁺). |
| 84 | 4-fluoro-1H-pyrazol-1-yl* | H | Bn | ¹H NMR(CD₃OD, 400 MHz) δ 5.05(s, 2H), 6.94(s, 1H), 7.34(m, 5H), 7.54(d, 1H) 8.33(d, 1H). |
| 85 | 3,5-dimethyl-1H-pyrazol-1-yl* | H | Bn | ¹H NMR(CDCl₃, 400 MHz) δ 2.27(s, 3H), 2.43(s, 3H), 4.91(s, 2H), 5.04(s, 2H), 5.92(s, 1H), 6.76(s, 1H), 7.30(m, 6H). |
| 86 | 4-methyl-1H-pyrazol-1-yl* | H | Bn | ¹H NMR(CDCl₃, 400 MHz) δ 2.07(s, 3H), 4.97(s, 2H), 5.00(s, 2H), 6.96(s, 1H), 6.76(s, 1H), 7.25(m, 5H), 7.39(s, 1H), 8.10(s, 1H). |
| 87 | 3-(trifluoromethyl)-1H-pyrazol-1-yl* | H | Bn | ¹H NMR(CDCl₃, 400 MHz) δ 4.91(s, 2H), 5.12(s, 2H), 6.63(d, 1H), 7.15(s, 1H), 7.33(m, 5H), 8.44(s, 1H), 10.56(s, 1H). |
| 88 | 5-methyl-3-(trifluoromethyl)-1H-pyrazol-1-yl* | H | Bn | ¹H NMR(CDCl₃, 400 MHz) δ 2.52(s, 3H) 5.02(s, 2H), 5.09(s, 2H), 6.39(s, 1H), 6.86(s, 1H), 7.31(m, 6H). |

-continued

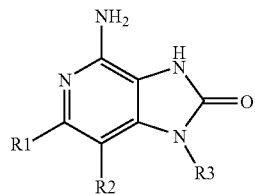

| Example No. | R1 | R2 | R3 | Data |
|---|---|---|---|---|
| 99 | ![pyrazole-CH2CH2OH] | H | Bn | $^1$H NMR(CD$_3$OD, 400 MHz) δ 2.72(t, 2H) 3.73(t, 2H) 5.06(s, 2H), 6.91(s, 1H), 7.34(m, 5H), 7.52(s, 1H) 8.27(s, 1H). |
| 90 | ![pyrazole] | H | ![CH2-pyridine-CH3] | $^1$H NMR((CD$_3$)$_2$SO) δ 2.40(s, 3H), 5.01(s, 2H), 5.94(s, 2H), 6.43(s, 1H), 6.98(s, 1H), 7.19(d, 1H), 7.55(dd, 1H), 7.64(s, 1H), 8.33(s, 1H), 8.45(s, 1H). |
| 91 | ![(R)-tetrahydrofuran-O] | H | ![CH2-pyridine-CH3] | $^1$H NMR(CD$_3$OD) δ 2.00-2.07(m, 1H), 2.13-2.23(m, 1H), 2.50(s, 3H), 3.79-3.97(m, 4H), 4.98(s, 2H), 5.37(m, 1H), 5.87(s, 1H), 7.26(d, 1H), 7.66(dd, 1H), 8.41(s, 1H). |
| 92 | ![(S)-tetrahydrofuran-O] | H | ![CH2-pyridine-CH3] | $^1$H NMR(CD$_3$OD) δ 2.00-2.06(m, 1H), 2.13-2.22(m, 1H), 2.50(s, 3H), 3.79-3.97(m, 4H), 4.98(s, 2H), 5.35(m, 1H), 5.87(s, 1H), 7.27(dd, 1H), 7.66(dd, 1H), 8.41(s, 1H). |
| 93 | ![1,2,3-triazole] | H | Bn | $^1$H NMR((CD$_3$)$_2$SO) δ 5.01(s, 2H), 6.07(s br, 2H), 6.97(s, 1H), 7.25-7.35(m, 5H), 7.94(s, 2H), 10.57(s br, 1H). LRMS (ES$^+$) m/z 308 (MH$^+$). |
| 94 | ![1,2,3-triazole isomer] | H | Bn | m/z 308 (MH$^+$). LCMS (acid-combo): t= 2.37, ES$^+$ 308 (MH$^+$), ES$^-$ 306 (MH$^-$). |
| 95 | ![1,2,4-triazole] | H | Bn | $^1$H NMR((CD$_3$)$_2$SO) δ 5.03(s, 2H), 6.07(s br, 2H), 6.89(s, 1H), 7.22-7.35(m, 5H), 8.12(s, 1H), 8.95(s, 1H). |
| 96 | ![1,2,4-triazole] | H | ![CH2-pyridine-CH3] | |

-continued

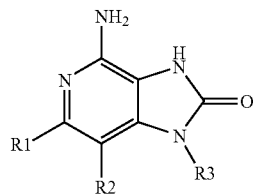

| Example No. | R1 | R2 | R3 | Data |
|---|---|---|---|---|
| 97 | ![oxazole with H3COCH2-] (2-(methoxymethyl)oxazol-4-yl) | H | *-CH2-(6-methylpyridin-3-yl) | 1H NMR(400 MHz, DMSO-d$_6$) δ ppm 2.42(s, 3H) 4.33(d, J=0.78 Hz, 2H) 5.06(s, 2H) 6.01(s, 2H) 7.21(d, J=7.80 Hz, 1H) 7.29(s, 1H) 7.57(dd, J=7.80, 2.34 Hz, 1H) 8.06(s, 1H) 8.47(d, J=1.95 Hz, 1H) 10.69(s, 1H), LCMS R$_t$=1.48 m/z 367 [MH]$^+$ |
| 98 | (2-(methoxymethyl)oxazol-4-yl) | H | Bn | 1H NMR(400 MHz, DMSO-d$_6$) δ ppm 3.28(s, 3H) 4.32(s, 2H) 5.05(s, 1H) 6.00(s, 2H) 7.20(s, 1H) 7.24-7.36(m, 5H) 8.04(s, 1H) 10.68(s, 1H). |
| 99 | (2-((dimethylamino)methyl)oxazol-4-yl) | H | Bn | 1H NMR(400 MHz, DMSO-d$_6$) δ ppm 2.17(s, 6H) 3.33(s, 2H) 5.06(s, 2H) 6.00(s, 2H) 7.18(s, 1H) 7.25-7.36(m, 5H) 7.93(s, 1H) 10.67(s, 1H). |
| 100 | (5-methyloxazol-2-yl) | H | *-CH2-(6-methylpyridin-3-yl) | |
| 101 | n-BuO- | H | Bn | $^1$H NMR(d6-DMSO) δ 10.04(br s, 1H), 7.35-7.22(m, 5H), 5.77(s, 1H), 5.55(br s, 2H), 4.85(s, 2H), 4.04(t, 2H), 1.62-1.53(m, 2H), 1.39-1.30(m, 2H), 0.88(t, 3H). |
| 102 | HOCH2CH2O- | H | Bn | $^1$H NMR(d6-DMSO) δ 10.06(br s, 1H), 7.38-7.22(m, 5H), 5.79(s, 1H), 5.58(br s, 2H), 4.85(s, 2H), 4.65(t, 1H), 4.05(t, 2H), 3.60(t, 2H). |
| 103 | cyclopropyl-CH2-O- | H | Bn | $^1$H NMR(d6-DMSO) δ 10.05(br s, 1H), 7.36-7.24(m, 5H), 5.79(s, 1H), 5.53(br s, 2H), 4.84(s, 2H), 3.88(d, 2H), 1.16-1.08(m, 1H), 0.52-0.44(m, 2H), 0.48-0.40(m, 2H). |
| 104 | (oxazol-2-yl) | H | *-CH2-(6-(trifluoromethyl)pyridin-3-yl) | 1H NMR(400 MHz, DMSO-d$_6$) δ ppm 5.24(s, 2H) 6.05(s, 2H) 7.30(s, 1H) 7.36(s, 1H) 7.88(d, J=8.21 Hz, 1H) 7.94(dd, J=8.21, 1.56 Hz, 1H) 8.12(s, 1H) 8.80(d, J=1.95 Hz, 1H) 10.75(s, 1H). |

-continued

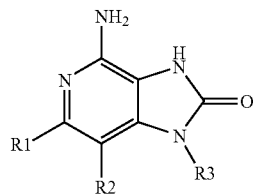

| Example No. | R1 | R2 | R3 | Data |
|---|---|---|---|---|
| 105 | 4-methyl-oxazol-2-yl (H₃C on oxazole) | H | CH₂-(6-trifluoromethyl-pyridin-3-yl) | 1H NMR(400 MHz, DMSO-d₆) δ ppm 2.12(s, 3H) 5.24(s, 2H) 6.02(s, 2H) 7.34(s, 1H) 7.81(d, J=1.17 Hz, 1H) 7.85-7.98(m, 2H) 8.80(d, J=1.56 Hz, 1H) 10.73(s, 1H), LCMS R$_t$= 2.34 m/z 391 [MH]⁺ |
| 106 | oxazol-2-yl | H | CH₂-(3-cyanophenyl) | 1H NMR(400 MHz, DMSO-d₆) δ ppm 5.12(s, 2H) 6.03(s, 2H) 7.26(s, 1H) 7.29(s, 1H) 7.56(t, J=7.62 Hz, 1H) 7.60-7.66(m, 1H) 7.73-7.78(m, 1H) 7.80-7.82(m, 1H) 8.12(s, 1H) 10.68(br. s., 1H), LCMS R$_t$= 2.08 m/z 333 [MH]⁺ |
| 107 | 4-methyl-oxazol-2-yl | H | CH₂-(3-cyanophenyl) | 1H NMR(400 MHz, DMSO-d₆) δ ppm 2.12(s, 3H) 5.12(s, 2H) 6.01(s, 1H) 7.25(s, 1H) 7.56(t, J=7.62 Hz, 1H) 7.59-7.64(m, 1H) 7.73-7.78(m, 1H) 7.79-7.83(m, 2H) 10.67(s, 1H), LCMS R$_t$=2.20 m/z 347 [MH]⁺ |
| 108 | CF₃ | H | CH₂-(4-chlorophenyl) | ¹H NMR((CD₃)₂SO) δ 5.02(s, 2H), 6.19(s, 2H), 7.04(s, 1H), 7.30(d, 2H), 7.39(d, 2H). |
| 109 | CF₃ | H | CH₂-(tetrahydropyran-4-yl) | LRMS (ES⁺) m/z 317 (MH⁺). ESCI MS: t=1.46, ES⁺ 334 (MNH₃⁺). |
| 110 | CF₃ | H | CH₂-(tetrahydrofuran-2-yl) | |
| 111 | 4-(morpholinomethyl)-oxazol-2-yl | H | Bn | |
| 112 | 4-((4-methylpiperazin-1-yl)methyl)-oxazol-2-yl | H | Bn | |
| 113 | CF₃ | H | CH₂-CH(OCH₃)CH₃ (S) | |

-continued

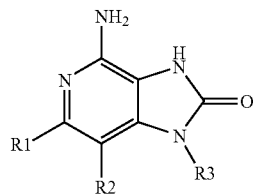

| Example No. | R1 | R2 | R3 | Data |
|---|---|---|---|---|
| 114 | CF₃ | H | 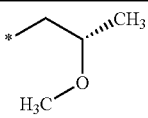 | |
| 115 | CF₃ | H | 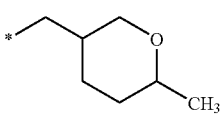 | |
| 116 | CF₃ | H | 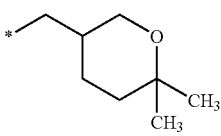 | |
| 117 | 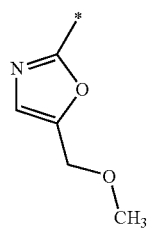 | H | Bn | |
| 118 | 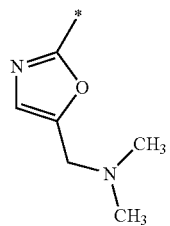 | H | Bn | |
| 119 | 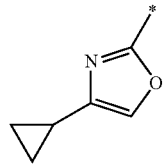 | H | 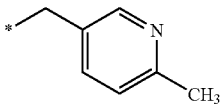 | |

Preparation 1

3-Amino-3-cyclopropyl-acrylic acid ethyl ester

Cyclopropanecarbonitrile (2.7 g, 40.5 mmol) was dissolved in dry THF (100 mL) and firstly zinc (13.2 g, 202.3 mmol) and then zinc oxide (1.6 g, 20.2 mmol) were added followed by dropwise addition of ethylbromoacetate (6.7 g, 40.5 mmol). The mixture was sonicated in a 35 kHz ultrasonic bath under N₂ for 2 hours. After 30 minutes a green colour was observed. The mixture was filtered through celite to remove the zinc and zinc oxide. The filtrate was added to 20 ml of 50% $K_2CO_3$ (aq) solution. A thick precipitate formed which was filtered to remove the solid and the aqueous was extracted with 100 ml EtOAc. The extract was washed with 20 ml brine, dried over $MgSO_4$ and concentrated in vacuo to give the crude product (3.8 g). The crude material was purified by column chromatography on silica gel eluting with 90:10 pentane: EtOAc to give the title compound (1.32 g) as a yellow oil.

$^1$H NMR (CDCl3) □ 4.47 (s, 1H), 4.11 (quart, 2H), 1.45-1.39 (m, 1H), 1.26 (t, 3H), 0.88-0.83 (m, 2H), 0.76-0.72 (m, 2H); LRMS (APCI+) m/z 156 [MH]$^+$.

Preparation 2

6-Cyclopropyl-2,4-dihydroxy-nicotinic acid ethyl ester

Sodium metal (8.1 g, 119 mmol) was cut into small pieces and added portionwise to stirred ethanol (120 mL) at room temperature under a nitrogen atmosphere. The mixture was then stirred at 60° C. under $N_2$ overnight to ensure complete dissolution of the metal. Diethyl malonate (18.1 ml, 119 mmol) was added to the sodium ethoxide solution at 60° C. and the mixture was stirred at 60° C. under $N_2$ for 1 h. A solution 3-Amino-3-cyclopropyl-acrylic acid ethyl ester (10.3 g, 40 mmol) in ethanol (10 mL) was added dropwise at 60° C. and the mixture was heated at reflux under $N_2$ for 5 days to give an orange suspension. The mixture was allowed to cool to room temperature and the resulting solid collected by filtration. The filtrate was concentrated in vacuo to give more solid. The combined solids were dissolved in water (150 mL) and the solution washed with EtOAc (150 mL). The aqueous was acidified to pH2 using concentrated HCl causing a white solid to precipitate. The solid was collected by filtration, washed with cold water and then $Et_2O$, and then dried in vacuo at 40° C. overnight to give the title product (5.32 g) as a fine white solid. The filtrate was concentrated in vacuo to half its volume causing more product to precipitate. This second crop of solid was collected by filtration, washed with water and $Et_2O$ and dried in vacuo at 40° C. to give a further 0.35 g of the title compound as a pale beige solid.

$^1$H NMR (d6-DMSO) ☐ 12.71 (br s, 1H), 11.43 (br s, 1H), 5.51 (s, 1H), 4.26 (quart, 2H), 1.86-1.79 (m, 1H), 1.26 (t, 3H), 1.06-1.01 (m, 2H), 0.90-0.86 (m, 2H); LRMS (APCI) m/z 224 [MH]$^+$.

Preparation 3

6-Cyclopropyl-2,4-dihydroxy-pyridine

6-Cyclopropyl-2,4-dihydroxy-nicotinic acid ethyl ester (5.3 g, 20.5 mmol) was dissolved in concentrated HCl (25 mL) and the mixture was refluxed overnight. The mixture was cooled to room temperature and then neutralised with concentrated ammonia. The resulting precipitate was collected by filtration, washed with cold water and acetonitrile and dried in vacuo at 40° C. over 2 days to give the title compound (3.39 g) as a beige powder.

$^1$H NMR (d6-DMSO) ☐ 10.96 (br s, 1H), 10.25 (br s, 1H), 5.38, (d, 1H), 5.32 (d, 1H), 1.79-1.72 (m, 1H), 0.93-0.89 (m, 2H), 0.75-0.71 (m, 2H); LRMS (ES) m/z 152 [MH]$^+$.

Preparation 4

6-Cyclopropyl-2,4-dihydroxy-3-nitro-pyridine

6-Cyclopropyl-2,4-dihydroxy-pyridine (1 g, 6.6 mmol) was suspended in AcOH:EtOAc (4:1, 10 mL) at room temperature. The mixture was warmed to 30° C. and a small portion of fuming nitric acid (0.05 ml, 1.2 mmol) was added dropwise, keeping the temperature between 30 and 35° C. Upon addition the mixture became a clear solution. The remainder of the fuming nitric acid (0.25 ml, 6.3 mmol) was added dropwise. The clear solution was allowed to cool to room temperature upon which a precipitate started to form. The mixture was stirred at room temperature overnight. The solid was collected by filtration, washed with cold water and $Et_2O$ and dried in vacuo at room temperature over the weekend to give the title compound (1.21 g) as a yellow powder.

$^1$H NMR (d6-DMSO) ☐ 12.17 (br s, 1H), 11.88 (br s, 1H), 5.57 (s, 1H), 1.88-1.81 (m, 1H), 1.08-1.03 (m, 2H), 0.87-0.83 (m, 2H); LRMS (APCI) m/z 197 [MH]$^+$

Preparation 5

6-Cyclopropyl-2,4-dichloro-3-nitro-pyridine

6-Cyclopropyl-2,4-dihydroxy-3-nitro-pyridine (1.2 g, 6.1 mmol) was suspended in $POCl_3$ (5 mL). The mixture was heated at 85° C. under a caustic scrubber overnight. Excess $POCl_3$ was removed in vacuo, the reaction residue was dissolved in EtOAc (50 mL) and added dropwise to stirred warm water (50 mL) using ice to control the temperature. The layers were separated and the aqueous was extracted with 90:10 EtOAc:MeOH (100 mL). The organics were washed with brine (50 mL), dried over $MgSO_4$ and concentrated to give the crude product (2 g). Column chromatography through silica gel eluting with 90:10 pentane:EtOAc gave the title compound (893 mg) as a pale yellow crystalline solid.

$^1$H NMR (d6-DMSO) ☐ 7.94 (s, 1H), 2.31-2.24 (m, 1H), 1.18-1.14 (m, 2H), 1.06-1.02 (m, 2H); LRMS (APCI) m/z 233 [MH]$^+$.

Preparation 6

Benzyl-(2-chloro-6-cyclopropyl-3-nitro-pyridin-4-yl)-amine

6-Cyclopropyl-2,4-dichloro-3-nitro-pyridine (160 mg, 0.8 mmol) was dissolved in THF (2 mL) and triethylamine (104☐l, 0.8 mmol) and benzylamine (81☐l, 0.8 mmol) were added. The mixture was stirred at room temperature under a nitrogen atmosphere for 48 hours by which time a yellow precipitate had formed. The volatiles were removed in vacuo and the residue was stored in a stoppered flask at room temperature for 10 days. The residue was purified by column chromatography on silica gel eluting with 99:1 DCM:MeOH then 98:2 DCM:MeOH to give the title compound (185 mg) as a yellow crystalline solid.

$^1$H NMR (CDCl3) ☐ 7.42-7.31 (m, 5H), 7.05 (brs, 1H), 6.47 (s, 1H), 4.49 (d, 2H), 1.88-1.81 (m, 1H), 1.09-1.04 (m, 2H), 1.01-0.96 (m, 2H); LRMS (APCI) m/z 304 [MH]$^+$.

Preparation 7

Benzyl-(3-amino-2-chloro-6-cyclopropyl-pyridin-4-yl)-amine

Benzyl-(2-chloro-6-cyclopropyl-3-nitro-pyridin-4-yl)-amine (245 mg, 0.8 mmol) was dissolved in AcOH:$H_2O$ (9.0:0.9 mL). Iron powder (270 mg, 4.8 mmol) was added and the mixture was vigorously stirred at room temperature under a nitrogen atmosphere over the weekend, during which an off-white precipitate had precipitated out. The reaction mixture was diluted with EtOAc (20 mL) and water (20 mL), the mixture filtered through celite, and the filter cake washed with EtOAc (20 mL). The phases were separated and the organic layer was washed with saturated aqueous $NaHCO_3$ (10 mL) and brine (10 mL), dried over $MgSO_4$ and concentrated in vacuo. The residue was dried in vacuo at 40° C. overnight to give the title compound (215 mg) as an off-white crystalline solid.

$^1$H NMR (CDCl$_3$) ☐ 7.40-7.31 (m, 5H), 6.29 (s, 1H), 4.59 (br s 1H), 4.37 (d, 2H), 3.30 (br s 2H), 1.89-1.82 (m, 1H), 0.87-0.86 (m, 4H); LRMS (APCI) m/z 274 [MH]$^+$.

Preparation 8

1-Benzyl-4-chloro-6-cyclopropyl-1,3-dihydro-imidazo[4,5-c]pyridin-2-one

Benzyl-(3-amino-2-chloro-6-cyclopropyl-pyridin-4-yl)-amine (210 mg, 0.8 mmol) was dissolved in acetonitrile (10 mL). 1,1-Carbonyldiimidazole (370 mg, 2.3 mmol) was added and the mixture was heated at 80° C. under a nitrogen atmosphere for 2 hours. A further 250 mg (1.5 mmol) of 1,1-carbonyldiimidazole was added and the mixture was heated at 80° C. overnight. The mixture was allowed to cool to room temperature and the solvent was removed in vacuo. The residue was dissolved in DCM (20 mL) and washed with 1N HCl (10 mL), then water (10 mL) and brine (10 mL), dried over $MgSO_4$ and concentrated in vacuo. The residue was dried in vacuo at 40° C. overnight to give the title compound (217 mg) as a white fluffy solid.

$^1$H NMR (CDCl$_3$) □ 8.20 (br s, 1H), 7.38-7.31 (m, 5H), 6.59 (s, 1H), 5.03 (s, 2H), 1.96-1.91 (m, 1H), 0.94-0.92 (m, 4H); LRMS (APCI) m/z 300 [MH]$^+$.

Preparation 9

4-Allylamino-1-Benzyl-6-cyclopropyl-1,3-dihydro-imidazo[4,5-c]pyridin-2-one

1-Benzyl-4-chloro-6-cyclopropyl-1,3-dihydro-imidazo[4,5-c]pyridin-2-one (100 mg, 0.3 mmol) was dissolved in allylamine (2 mL) in a Reactivial™. Copper (II) sulphate (83 mg, 0.3 mmol) was added and the vial was sealed. The mixture was heated at 85° C. overnight. Further portions of copper (II) sulphate (83 mg, 0.3 mmol) and allylamine (1 mL) were added and the vial was sealed once again. The mixture was heated at 85° C. over the weekend. The mixture was allowed to cool to room temperature. The excess allylamine was removed in vacuo and the residue was dissolved in EtOAc (50 mL) and treated with saturated aqueous NaHCO$_3$ (20 mL). The layers were separated and the organics washed with more saturated aqueous NaHCO$_3$ (10 mL), then brine (10 mL), dried over MgSO$_4$ and concentrated in vacuo to give the crude product (120 mg). Column chromatography through silica gel eluting with 98:2 DCM:MeOH gave the title compound (73 mg) as an off white solid.

$^1$H NMR (CDCl$_3$) □ 10.40 (br s, 1H), 7.34-7.25 (m, 5H), 6.17-6.15 (m, 1H), 5.96-5.87 (m, 1H), 5.17 (d, 1H), 5.02-5.00 (m, 1H), 4.89 (s, 2H), 4.05-4.00 (m, 2H), 1.85-1.80 (m, 1H), 0.97-0.93 (m, 2H), 0.84-0.76 (m, 2H); LRMS (APCI) m/z 321 [MH]$^+$.

Preparation 10

Benzyl-(2-chloro-6-methyl-3-nitro-pyridin-4-yl)-amine 2,4-Dichloro-6-methyl-3-nitro-pyridine (2 g, 9.7 mmol) and triethylamine (1.35 mL, 9.7 mmol) were dissolved in 40 mL THF and cooled (ice/water) to ~5° C. A solution of benzylamine (1.04 g, 9.7 mmol) in 10 mL THF was added dropwise and the mixture was then allowed to warm gradually to room temperature overnight. The mixture was evaporated in vacuo, partitioned between EtOAc (50 mL) and water (20 mL). The organic layer was washed with saturated aqueous NaHCO$_3$ (10 mL), dried (MgSO$_4$) and evaporated in vacuo to an orange gum. This gum was preabsorbed onto silica gel and then purified by column chromatography, eluting with DCM:pentane 3:1. Appropriate fractions combined and evaporated in vacuo to yield the title compound as a yellow solid (716 mg).

$^1$H NMR (CDCl$_3$) □ 2.32 (s, 3H), 4.38 (d, 2H), 6.39 (s, 1H), 6.90 (broad s, 1H), 7.21 (m, 2H), 7.29 (m, 3H). LC-MS (ELSD, ES$^+$) m/z 278 (MH$^+$).

Preparation 11

N-2', N-2', N-4'-Tribenzyl-6-methyl-3-nitro-2,4-diamine

Benzyl-(2-chloro-6-methyl-3-nitro-pyridin-4-yl)-amine (99 mg, 0.4 mmol) and triethylamine (55□l, 0.4 mmol) were dissolved in THF (2 mL) and dibenzylamine (77 mg, 0.4 mmol) was added dropwise. The resulting reaction mixture was stirred at room temperature overnight, and then evaporated in vacuo. The residue was partitioned between EtOAc (5 mL) and saturated aqueous NaHCO$_3$ (3 mL). The organic layer was dried (MgSO$_4$) and evaporated in vacuo to a yellow gum which was preabsorbed onto silica gel and then purified by column chromatography, eluting with 1:1 DCM:pentane. Appropriate fractions were combined and evaporated in vacuo to a bright yellow gum which solidified on standing to give the title compound (75 mg).

$^1$H NMR (CDCl$_3$) □ 2.32 (s, 3H), 4.45 (d, 2H), 4.54 (s, 4H), 5.96 (s, 1H), 7.13-7.40 (m, 15H), 8.12 (broad s, 1H). LRMS (ES+) m/z 439 (MH$^+$).

Preparation 12

N-2', N-2', N-4'-Tribenzyl-6-methyl-2,3,4-triamine

N-2', N-2', N-4'-Tribenzyl-6-methyl-3-nitro-2,4-diamine (59 mg, 0.14 mmol) was dissolved in ethanol (5 mL) and hydrogenated at 30 psi over Raney nickel (6 mg) at room temperature for 1 hour. A further 12 mg Raney nickel was added and the mixture was hydrogenated at 30 psi and room temperature for a further 1.5 hours. The reaction mixture was filtered through a short plug of Arbocel and the filtrate was then evaporated in vacuo to an opaque gum of the title compound, 39 mg.

$^1$H NMR (DMSO) □ 2.08 (s, 3H), 4.07 (s, 4H), 4.21 (s, 2H), 4.30 (d, 2H), 5.83 (t, 1H exchangeable), 6.05 (s, 1H), 7.14-7.34 (m, 15H). LRMS (APCI$^+$) m/z 409 (MH$^+$).

Preparation 13

1-Benzyl-4-dibenzylamino-6-methyl-1,3-dihydro-imidazo[4,5-c]pyridin-2-one

N-2', N-2', N-4'-Tribenzyl-6-methyl-2,3,4-triamine (35 mg, 0.09 mmol) and 1,1-carbonyldiimidazole (139 mg, 0.86 mmol) was dissolved in acetonitrile (3 mL) and the mixture heated under reflux for 3 hours. The reaction mixture was evaporated in vacuo and the residue purified by column chromatography using DCM as the eluant. Appropriate fractions were combined and evaporated in vacuo to give the title compound as a white solid, 30 mg.

$^1$H NMR (CDCl3) □ 2.32 (broad s, 3H), 4.68 (s, 4H), 4.85 (s, 2H), 6.18 (s, 1H), 7.18-7.26 (m, 15H). LRMS (ES$^+$) m/z 435 (MH$^+$).

Preparation 14

N4-Benzyl-2-chloro-6-trifluoromethyl-pyridine-3,4-diamine

Benzyl-(2-chloro-3-nitro-6-trifluoromethyl-pyridine-4-yl)-amine (345 mg, 1.0 mmol) was dissolved in a mixture of AcOH (18 ml) and water (2 ml). Fe powder (349 mg, 6.2 mmol) was added and the mixture was vigorously stirred at room temperature for 24 h. The reaction mixture was concentrated in vacuo and the residue was diluted with EtOAc (10 ml) and water (10 ml). The mixture was filtered through celite, washing through with EtOAc (20 ml). The layers were separated and the organic layer was washed with sat. NaHCO$_3$ $_{(aq)}$ (2×10 ml) and brine (10 ml), dried over MgSO$_4$ and concentrated in vacuo to give the title compound (304 g) as a pale yellow solid.

$^1$H NMR (CDCl$_3$) ☐ 7.43-7.34 (m, 5H), 6.87 (s, 1H), 4.46 (br s, 1H), 4.42 (d, 2H), 3.72 (br s, 2H); LRMS (APCI and ES) m/z 302 [MH]$^+$.

Preparation 15

1-Benzyl-4-chloro-6-trifluoromethyl-pyridine-2-one

N4-Benzyl-2-chloro-6-trifluoromethyl-pyridine-3,4-diamine (300 mg, 1.0 mmol) was dissolved in MeCN (20 ml). CDI (806 mg, 4.9 mmol) was added and the mixture was heated at 80° C. for 48 h. The mixture was allowed to cool to room temperature and the solvent was removed in vacuo. The residue was dissolved in EtOAc (50 ml) and washed with 1N HCl$_{(aq)}$ (20 ml), then water (20 ml) and brine (20 ml), dried over MgSO$_4$ and concentrated in vacuo to give the title compound (325 g) as a pale yellow solid.

$^1$H NMR (CDCl$_3$) ☐ 7.41-7.33 (m, 5H), 7.14 (s, 1H), 5.11 (s, 2H); LRMS (APCI and ES) m/z 328 [MH]$^+$.

Preparation 16

1-Benzyl-4-benzylamino-6-trifluoromethyl-1,3-dihydro-imidazo[4,5-c]pyridine-2-one 1-Benzyl-4-chloro-6-trifluoromethyl-pyridine-2-one (100 mg, 0.3 mmol) was dissolved in BnNH$_2$ (2 ml) in a reactivial. CuSO$_4$ (152 mg, 0.6 mmol) was added and the vial was sealed. The reaction mixture was heated at 80° C. for 120 h. The reaction mixture was allowed to cool to room temperature and dissolved in EtOAc (20 ml). The mixture was washed with sat. NaHCO$_3$ $_{(aq)}$ (2×5 ml) and brine (5 ml), dried over MgSO$_4$ and concentrated in vacuo to give the crude (700 mg). Column chromatography through silica eluting with 99:1 DCM:MeOH gave the title compound (50 mg) as a yellow solid.

$^1$H NMR (CDCl$_3$) ☐ 10.66 (br s, 1H), 7.34-7.10 (m, 10H), 6.58 (s, 1H), 5.86-5.84 (m, 1H), 4.70 (d, 2H), 4.66 (s, 2H); LRMS (APCI and ES) m/z 399 [MH]$^+$.

An alternative preparation of the above title compound is described below;

N2,N4-Dibenzyl-6-trifluoromethyl-pyridine-2,3,4-triamine (9.02 g, 24.2 mmol) was dissolved in TBME (180 ml) and CDI (19.6 g, 121 mmol) was added. The reaction mixture was stirred at room temperature for 72 h. Water (100 ml) was added to the reaction mixture and the layers were separated. The aqueous was extracted with EtOAc (200 ml). The combined organics were washed with brine (50 ml), dried over MgSO$_4$ and concentrated in vacuo to give the crude (25 g). Column chromatography through silica eluting with 30:70→60:40 Heptane:EtOAc gave the title compound (2.64 g) as a white fluffy solid.

$^1$H NMR (CDCl$_3$) ☐ 10.52 (br s, 1H), 7.44-7.12 (m, 10H), 6.60 (s, 1H), 5.76-5.72 (m, 1H), 4.71-4.70 (m, 4H); LRMS (APCI and ES) m/z 399 [MH]$^+$.

Preparation 17

N2,N4-Dibenzyl-3-nitro-6-trifluoromethyl-pyridine-2,4-diamine

3-Nitro-6-trifluoromethyl-pyridine-2,4-diol (5.0 g, 22.3 mmol) was dissolved in DCM (50 mL) and Et$_3$N (6.22 ml, 44.6 mmol) was added. The mixture was cooled to 0° C. and Tf$_2$O (7.32 ml, 44.6 mmol) was added dropwise. The mixture was allowed to warm to room temperature and stirred for 1 hour. The reaction mixture was concentrated in vacuo and the residue was dissolved in THF (50 ml). BnNH$_2$ (7.3 ml, 66.9 mmol) was added and the mixture was stirred at 50° C. for 24 h. The reaction mixture was cooled to room temperature and concentrated in vacuo. The residue was treated with water (50 ml) and extracted with EtOAc (150 ml). The extract was washed with brine (50 ml), dried over MgSO$_4$ and concentrated in vacuo to give the crude (27 g).

A second batch of 3-Nitro-6-trifluoromethyl-pyridine-2,4-diol (11.06 g, 49.4 mmol) was dissolved in DCM (100 mL) and Et$_3$N (13.8 ml, 98.7 mmol) was added. The mixture was cooled to 0° C. and Tf$_2$O (16.2 ml, 98.7 mmol) was added dropwise. The mixture was allowed to warm to room temperature and stirred for 1 hour. The reaction mixture was concentrated in vacuo and the residue was dissolved in THF (100 ml). BnNH$_2$ (16.2 ml, 148 mmol) was added and the mixture was stirred at 50° C. for 24 h. The reaction mixture was cooled to room temperature and concentrated in vacuo. The residue was treated with water (100 ml) and extracted with EtOAc (200 ml). The extract was washed with brine (50 ml), dried over MgSO$_4$ and concentrated in vacuo to give the crude (53 g). The two crudes were combined. Column chromatography through silica eluting with 95:5→90:10 Pentane:EtOAc gave the title compound (15.93 g) as a yellow solid.

$^1$H NMR (CDCl$_3$) ☐ 9.68-9.64 (m, 1H), 9.36-9.32 (m, 1H), 7.43-7.29 (m, 10H), 6.38 (s, 1H), 4.81 (d, 2H), 4.55 (d, 2H); LRMS (APCI and ES) m/z 403 [MH]$^+$.

Preparation 18

N2,N4-Dibenzyl-6-trifluoromethyl-pyridine-2,3,4-triamine

N2,N4-Dibenzyl-3-nitro-6-trifluoromethyl-pyridine-2,4-diamine (15.9 g, 35.6 mmol) was dissolved in a mixture of THF (100 ml) and MeOH (200 ml). Raney Nickel (3.18 g, 20 wt %) was added and the mixture was stirred at room temperature under 80 psi H$_2$ for 1 hour. The mixture was filtered through celite to remove the catalyst and the filtrate was concentrated in vacuo to give an oil. Trituration in MeOH with a small amount of water gave a precipitate which was collected by filtration, washed with cold MeOH and dried in vacuo to give the title compound (9.02 g) as a white solid.

$^1$H NMR (CDCl$_3$) ☐ 7.43-7.28 (m, 10H), 6.57 (s, 1H), 4.66 (d, 2H), 4.62-4.59 (m, 1H), 4.57-4.54 (m, 1H), 4.39 (d, 2H), 2.49 (br s, 2H); LRMS (APCI and ES) m/z 373 [MH]$^+$.

Preparation 19

2,4-Dihydroxy-6-trifluoromethyl-nicotinic acid ethyl ester

Pyridine (53 mls/660 mmols) was added to dissolve 3-Amino-4,4,4-trifluorocrotonic acid ethyl ester (100 g/546 mmols) in DCM(6000 mls). The mixture was then placed under nitrogen and cooled to 5° C. by suspending in an ice-bath. Ethyl malonyl chloride was added dropwise over approx 1 hr such that temperature did not exceed 20° C. The resulting pale brown solution was stirred at 5° C. for 3 hrs then allowed to warm to room temperature overnight to give a dark green solution. The mixture was then washed with 1M HCl$_{(aq)}$ (200 mls) then sat.NaHCO$_{3(aq)}$ (250 mls). Aqueous washings were sequentially re-extracted with further DCM (2×250 mls). The Organic layers were combined, dried over Na$_2$SO$_4$, filtered and concentrated to a dark green oil of crude 3-(2-Ethoxycarbonyl-acetylamino)-4,4,4-trifluoro-but-2-enoic acid ethyl ester (175 g). A portion of the crude material (120 g) was dissolved in EtOH (300 mls) and placed under nitrogen. Potassium tert-butoxide (54 g/480 mmols) was then added in several portions such that temperature did not exceed 60° C. resulting in a purple solution. The mixture was then heated at 70° C. for 3 hrs. EtOH (100 mls) was then added to reduce viscosity and heated at 80° C. for a further hour. The mixture was then allowed to cool and then concentrated in vacuo to a red solid. The mixture was dissolved in water (500 mls) and citric acid (180 g) then added, causing precipitation. EtOAc (600 mls) was then added and the mixture poured into a separating funnel and the aqueous layer run off. The organic layer containing much undissolved solid was filtered to give the title compound (46.5 g) as a white solid. Concentration of the organic filtrate and trituration with MeOH afforded further title compound (15.3 g) as a white solid.

$^1$H NMR (d6-DMSO, 400 MHz) ☐ 1.20-1.25 (t, 3H), 4.20-4.25 (q, 2H), 6.8 (s, 1H)

Preparation 20

6-Trifluoromethyl-pyridine-2,4-diol 2,4-Dihydroxy-6-trifluoromethyl-nicotinic acid ethyl ester (62 g/247 mmols) was added in several portions over 30 mins to 6M HCl$_{(aq)}$ (620 mls) at reflux. The resulting mixture was then heated at 100° C. overnight with vigorous stirring to obtain complete solution. The solution was then allowed to cool and concentrated in vacuo to a white solid. This was slurried in water (250 mls) and adjusted to pH 7 with conc. ammonia to get heavy white suspension. The resulting solid was collected by filtration, rinsed through with fresh water, and dried to provide the title compound (44.0 g) as a white solid.

$^1$H NMR (d6-DMSO, 400 MHz) ☐ 6.05 (s, 1H), 6.6 (s, 1H)

Preparation 21

Ethyl-[2,3-diamino-6-(trifluoromethyl)-pyridin-4-yl]-benzylcarbamate

Crude ethyl-[2-Amino-3-nitro-6-(trifluoromethyl)-pyridin-4-yl]-benzylcarbamate (65 gm, 170 mmol) was dissolved in ethanol (1000 mL) and 10% Pd—C (6 gm) was added. Hydrogenation at 40° C. and 40 psi for 1 hour gave complete reduction of the nitro group. The catalyst was removed by filtration and the filtrate evaporated to dryness under reduced pressure to give a light brown semi-solid. Trituration with t-butyl methyl ether (150 mL) followed by filtration and washing with the same solvent (30 mL) gave the title compound (36 gm, 60% yield) as a white solid.

1H NMR (DMSOd$_6$) ☐7.30-7.21 (m, 5H), 6.32 (broad s, 1H), 6.15 (broad s, 2H), 5.39 (broad s, 2H), 5.00 (broad d, 1H), 4.25 (broad d), 4.09 (broad d, 2H), 1.12 (broad s, 3H); LRMS (ES$^+$) m/z 355 (MH$^+$)

Preparation 22

Ethyl-[2-amino-3-nitro-6-(trifluoromethyl)-pyridin-4-yl]-benzylcarbamate

Ethyl-[2-chloro-3-nitro-6-(trifluoromethyl)-pyridin-4-yl]-benzylcarbamate (63 gm 160 mmol) was dissolved in tetrahydrofuran (300 mL) and to this was added 0.880 ammonia solution (100 mL) to give two phases. This was transferred to a pressure vessel, sealed and heated to 80° C. with stirring for 2 hours. The tetrahydrofuran was evaporated and the residue was partitioned between saturated brine and diethyl ether. The organic extracts were dried over sodium sulphate, filtered and evaporated to give a thick yellow slurry (65 gm) of crude product.

LRMS (ES$^+$) m/z 385 (MH$^+$), (ES$^-$) m/z 383 (M$^-$H).

Preparation 23

Ethyl-[2-chloro-3-nitro-6-(trifluoromethyl)-pyridin-4-yl]-benzylcarbamate

Benzyl-(2-chloro-3-nitro-6-trifluoromethyl-pyridin-4-yl)-amine (57 gm 170 mmol) was dissolved in tetrahydrofuran (750 mL) and stirred under N$_2$. The resulting mixture was then cooled in an ice/salt bath to −5° C. A solution of potassium t-butoxide (21.2 gm, 189 mmol) in tetrahydrofuran (200 mL) was added drop wise over a period of ~30 minutes, maintaining the temperature between −5° and 0° C., to give a deep red reaction mixture. The resulting mixture was then stirred at this temperature for 15 minutes before the drop wise addition of a solution of ethyl chloroformate (21.4 gm, 198 mmol) in tetrahydrofuran (100 mL), keeping the temperature below 5° C.

The cooling bath was removed and the reaction mixture was allowed to reach ambient temperature over 1 hour to give a light brown hazy solution. Evaporation of the solvent was followed by partition of the residue between saturated brine (50 mL) and t-butyl methyl ether (300 mL). The organic phase was washed with water (50 mL) followed by saturated brine (50 mL), dried over sodium sulphate, filtered and evaporated to give a brown oil. The oil was dissolved in n-pentane (250 mL) and stored at ambient temperature overnight.

The n-pentane solution was decanted from a dark brown tar which had precipitated out. Evaporation of the solvent gave the title compound as a pale brown viscous oil (63 gm, 91% yield).

$^1$H NMR (CDCl$_3$) ☐ 7.28-7.10 (m, 5H), 4.80 (s, 2H) 4.15 (q, 2H) 1.18 (t, 3H); LRMS (ES$^+$) m/z 404/406 (MH$^+$).

Preparation 24

Benzyl-(2-chloro-3-nitro-6-trifluoromethyl-pyridin-4-yl)-amine

4-Benzylamino-3-nitro-6-trifluoromethyl-pyridin-2-ol (61.7 gm 197 mmol) was added to phenylphosphonic dichloride (180 mL) and heated to 100° C. in an oil bath, under N$_2$ overnight. The starting material dissolved on heating to give a light yellow solution. The mixture was then quenched on to ice water (600 gm of ice+100 mL water) to give a pale yellow solid. Filtered off and washed the solid well with water. The solid was dissolved in ethyl acetate (600 mL) and washed with aqueous sodium hydrogen carbonate solution (10% w/v) until there was no further effervescence and the pH of the aqueous washings were basic. The organic layer was dried over sodium sulphate, filtered and evaporated to give a dirty yellow solid. The solid was then dissolved in diethyl ether. To this was then added n-hexane until the solution was cloudy. Within a few minutes a thick flocculent solid had formed, which was then filtered off, washed with n-hexane and dried to give the title compound (60.59 gm 92% yield).

$^1$H NMR (CDCl$_3$) ☐ 7.44-7.30 (m, 5H), 7.04 (s, 1H), 6.95 (broad s, 1H) 4.53 (d, 2H); LRMS (ES$^+$) m/z 332 (MH$^+$).

Preparation 25

2-Chloro-3-nitro-6-trifluoromethyl-pyridin-4-ylamine

Benzyl-(2-chloro-3-nitro-6-trifluoromethyl-pyridin-4-yl)-amine (3.1 g, 9.3 mmol) was stirred in 5 ml concentrated sulphuric acid for 0.5 h before cautiously pouring the solution into a beaker of crushed ice. Solid $K_2CO_3$ was added portionwise until a basic pH was achieved and the aqueous extracted with 2×50 ml EtOAc. The combined organics were dried over $MgSO_4$ and concentrated in vacuo to afford 2.2 g of the title compound as a pale yellow solid.
$^1$H NMR (CDCl$_3$) δ 7.06(s, 1H), 5.87(bs, 2H; LRMS (ESCI) m/z 240 [M–H]+

Preparation 26

(2-Chloro-3-nitro-6-trifluoromethyl-pyridin-4-yl)-carbamic acid ethyl ester

2-Chloro-3-nitro-6-trifluoromethyl-pyridin-4-ylamine (2.2 g, 9.1 mmol) was stirred in 2-MeTHF (20 ml) and triethylamine added (1.52 ml, 10.9 mmol). The solution was cooled in an ice bath to ~5° C. before the dropwise addition of ethyl chloroformate (1.04 ml, 10.9 mmol), the solution warmed to ambient temperature and left to stir under a nitrogen atmosphere for 16 h. 20 ml EtOAc and 10 ml $H_2O$ were added and the phases separated, washed with a additional 2×10 ml sat'd brine solution. The organic extract was dried over $MgSO_4$, concentrated in vacuo and preabsorbed onto a silica column. Elution with Hept:EtOAc, 9:1 gave 2.1 g of the title compound as a white solid.
$^1$H NMR (CDCl$_3$) δ 8.79(s, 1H), 8.02(bs, 1H), 4.35-4.30(t, 2H), 1.38-1.35(qt, 3H); LRMS (ESCl) m/z 312 [M–H]+

Preparation 27

(2-benzylamino-3-nitro-6-trifluoromethyl-pyridin-4-yl)-carbamic acid ethyl ester (2-Chloro-3-nitro-6-trifluoromethyl-pyridin-4-yl)-carbamic acid ethyl ester (300 mg, 0.96 mmol) was dissolved in 10 mL of tetrahydrofuran and benzylamine (0.103 mL, 0.96 mmol) was added followed by triethylamine (0.194 mL, 1.91 mmol) and the reaction mixture was stirred at 60° C. overnight. The solvent was removed and the solid was partitioned in ethyl acetate/water (50 mL/30 mL), the organic layer was dried over MgSO4, concentrated and purified by column chromatography on silica eluting with a gradient of 0% to 10% of methanol in ethyl acetate in to give 323 mg of the title compound as a yellow solid.
1H NMR (CDCl$_3$): δ 10.75(s, 1H), 8.89(s, 1H), 8.22(s, 1H), 7.35(m, 5H), 4.82(d, 2H), 4.31 (q, 2H), 1.36(t, 3H); LRMS (APCI) m/z 385 [MH]$^+$

Preparation 28

(3-amino-2-benzylamino-6-trifluormethyl-pyridin-4-yl )-carbamic acid ethyl ester (2-benzylamino-3-nitro-6-trifluormethyl-pyridin-4-yl)-carbamic acid ethyl ester (95 mg, 0.25 mmol) was dissolved in 10 mL of ethanol and Raney Nickel (20 mg, 20% MW) was added then the reaction mixture was stirred at room temperature in a bomb under 50 PSI of hydrogen for 2 h. The mixture was filtered through arbocel and the filtrate was concentrated in vacuo to give 88 mg of the title compound as a pale green gum.
LRMS (APCI) m/z 355 [MH]+

Preparation 29

4-benzylamino-6-trifluoromethyl-1,3-dihydro-imidazo(4,5-c)pyridine-2-one (3-amino-2-benzylamino-6-trifluormethyl-pyridin-4-yl)-carbamic acid ethyl ester (88 mg, 0.25 mmol) was dissolved in 5 mL of acetic acid and the reaction mixture was stirred at 80° C. overnight. The solvent was removed and the gum was partitioned in water/ethyl acetate. The organic layer was isolated, dried over MgSO4, the solvent was removed in vacuo and purified by column chromatography on silica eluting with a gradient of 1% to 5% of methanol in ethyl acetate to give 37 mg of the title compound as a colourless gum.
1H NMR (CDCl3): δ 10.56(s, 1H), 7.51-7.47(m, 5H), 6.61-6.58(m, 2H), 5.87 (s, 1H), 4.61(d, 2H); LRMS (APCI) m/z 309 [MH]+

Preparation 30

4-benzylamino-1-(6-methyl-pyridyin-3-ylmethyl)-6-trifluoromethyl-1,3-dihydro-imidazo(4,5-c)pyridine-2-one 4-benzylamino-6-trifluoromethyl-1,3-dihydro-imidazo(4,5-c)pyridine-2-one (100 mg, 0.32 mmol) was dissolved in 5 mL of dimethylformamide and potassium carbonate (89 mg, 0.65 mmol) was added followed by 5-chloromethyl-2-methyl-pyridine (46 mg, 0.32 mmol) and the reaction mixture was stirred at 80° C. overnight. Mass spec showed product expected with some bibenzylated product. The solvent was removed in vacuo and the residue was partitioned in ethyl acetate/water. The organic layer was isolated, dried over MgSO4, the solvent was removed in vacuo and the residue was purified by column chromatography on silica eluting with a gradient of 1% to 10% of methanol in ethyl acetate to give 30 mg of the title compound as a white solid.
1H NMR (d6 DMSO): δ 8.46(s, 1H), 7.57-7.55(dd, 1H), 7.38-7.16(m, 7H), 6.63(t, 1H), 5.02 (s, 2H), 4.59(d, 2H), 2.40(s, 3H); LRMS (APCI) m/z414 [MH]+

Preparation 31

(2-Chloro-3-nitro-6-trifluoromethyl-pyridin-4-yl)-(6-methyl-pyridin-3-ylmethyl)-carbamic acid ethyl ester Potassium carbonate (88 mg, 0.64 mmol) was added to a stirred solution of (2-Chloro-3-nitro-6-trifluoromethyl-pyridin-4-yl)-carbamic acid ethyl (100 mg, 0.32 mmol) in acetone (10 ml). 5-(chloromethyl)-2-methylpyridine (54.2 mg, 0.38 mmol) was added followed by sodium iodide (57.4 mg, 0.38 mmol) and the suspension stirred under a nitrogen atmosphere for 16 h. 20 ml EtOAc was added and the organic phases washed with 2×$H_2O$, dried over $MgSO_4$ and concentrated in vacuo to afford a red oil. The crude material was purified by column chromatography on silica, eluting with Hept:EtOAc, 3:2 to give 54 mg of the title compound as an orange solid.
$^1$H NMR (CDCl$_3$) δ 8.35(d, 1H), 7.54-7.51(dd, 1H), 7.31 (s, 1H), 7.16-7.15(d, 1H), 4.84(s, 2H), 4.23-4.18(qt, 2H), 2.55(s, 3H), 1.26-1.22(t, 3H); LRMS (ESCI) m/z419 [MH]+

Preparation 32

(2-Amino-3-nitro-6-trifluoromethyl-pyridin-4-yl)-(6-methyl-pyridin-3-ylmethyl)-carbamic acid ethyl ester (2-Chloro-3-nitro-6-trifluoromethyl-pyridin-4-yl)-(6-methyl-pyridin-3-ylmethyl)-carbamic acid ethyl ester (54 mg, 0.13 mmol) was dissolved in THF (1 ml) and transferred to a 10 ml reactivial. 880 Ammonia (1 ml) was added, the vessel sealed and the mixture stirred vigorously at ambient temperature for 16 h. The solution was concentrated in vacuo to give a crude oil which was purified directly by column chromatography on silica, eluting with 100% EtOAc to give 27 mg of the title compound as a yellow residue.

$^1$H NMR (CDCl$_3$) δ 8.39(s, 1H), 7.61-7.59(d, 1H), 7.15-7.13(d, 1H), 6.76(s, 1H), 6.25(bs, 2H), 4.92(s, 2H), 4.23-4.14 (qt, 2H), 2.54(s, 3H), 1.22-1.19(t, 3H): LRMS (APCI) m/z 400 [MH]+

Preparation 33

4-Benzylamino-3-nitro-6-trifluoromethyl-pyridin-2-ol

4-Chloro-3-nitro-6-trifluoromethyl-pyridin-2-ol (65.1 gm 268 mmol) was dissolved in tetrahydrofuran (350 mL) and stirred at room temperature under N$_2$. Benzylamine (86.3 gm 805 mmol) in tetrahydrofuran (50 mL) was added drop wise over 30 minutes to give a bright yellow solution. The reaction was heated in an oil bath at 50° C. for 18 hours, (a solid formed during the reaction). The resulting mixture was then cooled to ambient temperature, diluted with diethyl ether (200 mL) and the resulting solid (benzylamine hydrochloride) was then filtered off. The filtrate was evaporated to low bulk under reduced pressure to give a thick yellow slurry. Added diethyl ether (300 mL) and filtered off the yellow solid, dried on the filter pad to give the benzylamine salt (96.5 gm). The desired product was liberated by partition of the solid between aqueous 2N HCl and dichloromethane and crystallization from ethyl acetate/n-pentane gave the title compound as a pale yellow solid (61.7 gm 73.4% yield).

$^1$H NMR (DMSO d$_6$) 9.04 (broad s, 1H), 7.38-7.25 (m, 5H), 6.54 (s,1H), 4.67 (d, 2H); LRMS (ES$^+$) m/z 314 (MH$^+$).

Preparation 34

4-Chloro-3-nitro-6-trifluoromethyl-pyridin-2-ol

3-Nitro-6-trifluoromethyl-pyridine-2,4-diol (5.8 gm, 26 mmol) was heated in phenylphosphonic dichloride (30 mL) at 100° C. for 19 hours. The resulting mixture was then cooled and poured on to ice (60 gm), and then extracted with ethyl acetate (3×50 mL). The combined organic extracts were washed with aqueous sodium hydrogen carbonate solution (10% w/v) until the washings remained basic (pH ~8). The deep yellow organic layer was then washed with saturated brine, dried over sodium sulphate, filtered and evaporated to give a yellow gum. Trituration of the gum with dichloromethane gave a yellow solid which was filtered off and dried (4.65 gm). The solid was dissolved in water (25 mL) and acidified with 2N hydrochloric acid (7.5 mL) to give a thick white precipitate which was filtered off and washed with water. The precipitate was dissolved in ethyl acetate, dried over sodium sulphate, filtered and evaporated to give the title compound as a white solid (3.75 gm).

$^1$H NMR (DMSOd6) 7.78 (s, 1H). $^{13}$C NMR (DMSOd6) 157.2 (s) 145.2 (q) 138.1 (s) 136.98 (s) 120.6 (q) 113.86 (s). LRMS (ES$^-$) m/z 241/243 [MH]$^-$

Preparation 35

3-Nitro-6-trifluoromethyl-pyridine-2,4-diol

6-Trifluoromethyl-pyridine-2,4-diol (56 gm, 310 mmol) was added in 3-5 gm portions to conc. sulphuric acid (140 mL) with stirring to give a pale brown solution. The temperature increased to ~50° C. during the addition. Nitric acid (21.1 mL 328 mmol, 70% HNO3 d=1.4 gm/ml) was added drop wise at such a rate as to maintain a reaction temperature of between 45° and 50° C. which took approximately 90 minutes. Once all the nitric acid had been added the reaction was allowed to cool to ambient temperature over 3 hours. The reaction mixture was then poured into ice/water (~1.3 kg) with stirring, and after a few minutes a pale yellow precipitate formed which was filtered off, dissolved in ethyl acetate and dried over sodium sulphate, filtered and evaporated. A second crop of material was obtained by extraction of the aqueous filtrate with ethyl acetate. Combined batches and purified by crystallization from ethyl acetate/ n-heptane gave the title compound as a white 'fluffy' solid (49.5 gm 71% yield).

$^1$H NMR (DMSOd$_6$) 6.82 (s, 1H). $^{13}$C NMR (DMSOd$_6$) 159.82 (s) 157.58 (s) 143.10 (broad s) 127.26 (s) 120.85 (q) 102.83 (s).

Preparation 36

2,6-dibromo pyridine 1-oxide 2,6-dibromo pyridine (79 g, 334 mmol) was dissolved in 800 ml of dry dichloromethane and cooled under nitrogen to 5° C. then urea hydrogen peroxide (104 g, 1.1 mol) was added in one portion. When the mixture had cooled again to 3° C., a solution of trifluoro acetic acid anhydride (140 mL, 1 mol) in 100 ml DCM was added via dropping funnel over 45 min, whilst keeping the temperature between 5-7° C. The mixture was allowed to warm to room temperature and stirred for 20 hours. The mixture was cooled in an ice bath to 10° C. and 10% aq. Na$_2$SO$_3$ (~50 g/500 ml) was added dropwise over 60 minutes until test with starch iodide paper was negative. The resulting mixture was filtered to remove a quantity of fluffy solid and the layers were separated. The aqueous layer was extracted with dichloromethane (2×200 ml) and the combined extracts were dried over MgSO$_4$ and concentrated under reduced pressure to give a light brown solid. Recrystallisation of crude product using 600ml of boiling acetone gave 48.47 g of the title compound.

$^1$H NMR (CDCl$_3$) 7.65 (d, 2H), 6.95 (m, 1H).

Preparation 37

2,6-dibromo-4-nitro pyridine 1-oxide 2,6-dibromo pyridine 1-oxide (10 g, 39.5 mmol) was added to 65 mL of concentrated sulfuric acid at room temperature without cooling. Concentrated sulfuric acid (15 ml) and nitric acid (13.3 ml) were mixed and placed in a pressure equalising dropping funnel. The reaction mixture was heated to 79° C. then the nitrating mixture was added in portions over 25 minutes. When the addition was complete the mixture was stirred at 83-85° C. for 3.5 hours. The mixture was cooled to room temperature and slowly poured onto ~250 g crushed ice. A very pale yellow solid formed which was filtered off and washed with water (100 ml), dried in vacuum oven at 50° C. overnight to give 10.9 g of the title compound.

$^1$H NMR (CDCl$_3$) 8.45 (s, 2H).

Preparation 38

2,6-dibromo pyridin-4-ylamine 2,6-dibromo-4-nitro pyridine 1-oxide (14.5 g, 48.6 mmol) was taken up in 130 mL of acetic acid and iron powder (11 g, 196.9 mmol) was added in portionwise and the mixture was stirred at room temperature for 45 minutes. 500 mL of water was added and the product was extracted with EtOAc (500 mL). The organic layer was washed with 300 mL of water then with 300 mL of a sat K2CO3 sol and then with 300 mL of brine. The organic layer was dried over magnesium sulfate and the solvent was removed in vacuo to give 11.1 g of the title compound as a white solid.

$^1$H NMR (CDCl$_3$) ☐ 6.65 (s, 2H), 4.4-4.1 (s broad, 2H). LRMS (ES$^+$) m/z 251,253 [MH]$^+$

Preparation 39

2,6-dibromo pyridin-4-yl-N-nitroamine 2,6-dibromo pyridin-4-ylamine (11 g, 43.6 mmol) was dissolved in 100 mL of sulfuric acid at room temperature and then cooled at −5° C. 6 mL of nitric acid was added dropwise keeping the temperature between −10° C. to −5° C. and the mixture was stirred at −5° C. for 30 minutes. The mixture was then poured onto 400 mL of crushed ice. The solid formed was filtered off then dissolved in EtOAc. The residual water was removed and the organic layer was washed with 300 mL of brine, dried over magnesium sulfate and the solvent was removed in vacuo to give 12.5 g of the title product as a yellow solid.

$^1$H NMR (CDCl$_3$) ☐ 6.85 (s 1H), 5.7-5.4(s broad, 2H).

Preparation 40

2,6-dibromo-3-nitro-pyridin-4-ylamine

Concentrated sulphuric acid (250 ml) was heated in an oil bath until the temperature of the acid reached 47° C. 2,6-dibromo pyridin-4-yl-N-nitroamine (34.0 g, 114.5 mmol) was added in portions over 35 mins. The temperature of the mixture gradually rose throughout the addition period until it was 56° C. at the end. The mixture was stirred at 53-55° C. for 1 hour. Once the reaction was completed, the reaction mixture was cooled to in an ice-bath and poured on ~2 L of crushed ice with stirring. The product precipitated and was filtered off. Combined with other batch 00110916-140-001 from an identical scale reaction. The crude, wet amino nitro pyridine was dissolved in 700 ml EtOAc and the water layer was separated. The organic layer was washed with water (2×150 ml), 1×150 ml aq. NaHCO$_3$, brine (2×150 ml), dried (MgSO$_4$) and concentrated under reduced pressure to give 28 g of the title compound.

$^1$H NMR (CDCl$_3$) ☐ 7.3-7.2 (s broad, 1H), 7.55 (s, 2H).

Preparation 41

N-2,N-4-dibenzyl-6-bromo-3-nitro-pyridine-2,4-diamine 2,6-dibromo-3-nitro-pyridin-4-ylamine (6.5 g, 21.9 mmol) was suspended in concentrated HCl (100 mL) and cooled to 0° C., then sodium nitrite (7.5 g, 109 mmol) was added. There mixture was stirred for 30 minutes then warmed to room temperature. 100 mL of cooled water were added and the mixture was extracted with 100 mL of ethyl acetate. The organic layer was washed with 100 mL of water, dried over magnesium sulphate and the solvent was removed in vacuo to give 5.8 g of 2,6-dibromo-3-nitro-4-chloro pyridine as an orange oil. The oil was dissolved in 80 mL of THF and cooled to 0° C. Benzylamine (94.9 mL, 44.9 mmol) was dissolved in 20 mL of THF and added dropwise to the reaction followed by potassium carbonate (6.6 g, 48.2 mmol). The mixture was warmed to room temperature then heated at 50° C. overnight. Once the reaction was complete, the mixture was partitioned in water (150 mL) and ethyl acetate (100 mL). The organic layer was washed with 200 mL of water and 200 mL of brine, dried over magnesium sulphate and the solvent was removed in vacuo. 100 mL of ethanol was added and the mixture was sonicated for five minutes and let in the fume hood overnight. The precipitate was filtered off and washed with 30 mL of ethanol to give 4.56 g of the title compound as a yellow solid.

$^1$H NMR (CDCl$_3$) ☐ 9.6-9.4 (m broad, 2H), 7.4-7.2 (m, 10H), 6.2 (s, 1H), 4.8 (d, 2H), 4.45 (d, 2H). LRMS (ES$^+$) m/z 413,415 [MH]$^+$

Preparation 42

N-2,N-4-dibenzyl-3-nitro-6-vinyl-pyridine-2,4-diamine

N-2,N-4-dibenzyl-3-nitro-6-vinyl-pyridine-2,4-diamine (2 g, 5 mmol) was dissolved in THF (60 mL) and vinyl tributyltin (3.4 g, 10.8 mmol), palladium acetate (350 mg, 10% weight) and triphenylphosphine (380 mg) were added. The mixture was degazed with argon then heated at 80 degrees overnight. The solvent was removed in vacuo and the crude residue was purified by column chromatography on silica gel using 10% ethyl acetate in pentane as the eluant to give 1.9 g of the title compound as an orange solid.

$^1$H NMR (CDCl$_3$) ☐ 9.65 (s broad, 1H), 9.4 (s broad, 1H), 7.45-7.2 (m, 10H), 6.5-6.4 (m, 1H), 6.35 (m, 1H), 5.95 (s, 1H), 5.5 (m, 1H), 4.85 (d, 2H), 4.55 (d, 2H). LRMS (ES$^+$) m/z 361 [MH]$^+$

Preparation 43

4,6-bis-benzylamino-5-nitro-pyridine-2-carbaldehyde

N-2,N-4-dibenzyl-3-nitro-6-vinyl-pyridine-2,4-diamine (800 mg, 2 mmol) was dissolved in 10 mL of tetrahydrofuran and 30 mL of water then osmium tetroxide (60 mg, 0.2 mmol) was added followed by sodium metaperiodate (1.2 g, 5.6 mmol).The mixture was stirred at room temperature overnight. The mixture was partitioned in water (30 mL) and ethyl acetate (30 mL), the organic layer was washed with 50 mL of brine, dried over magnesium sulfate and the crude residue was purified by column chromatography on silica gel using 10% ethyl acetate in pentane as the eluant to give 450 mg of the title compound as an orange solid.

$^1$H NMR (CDCl$_3$) ☐ 9.78 (s, 1H), 9.55 (s broad, 1H), 9.3 (s broad, 1H), 7.4-7.2 (m, 10H), 7.62 (s, 1H), 5.5 (m, 1H), 4.9 (d, 2H), 4.6 (d, 2H). LRMS (ES$^+$) m/z 363 [MH]$^+$

Preparation 44

N-2,N-4-dibenzyl-6-morpholin-4-yl-methyl-3-nitro-pyridine-2,4-diamine 4,6-bis-benzylamino-5-nitro-pyridine-2-carbaldehyde (150 mg, 0.41 mmol) was dissolved in 15 mL of dichloromethane at room temperature and 2-methoxy-ethylamine (43 mg, 0.49 mmol) was added followed by acetic acid (25 mg, 0.41 mmol). The mixture was stirred for 5 minutes then sodium-triacetoxyboron hydride (130 mg, 0.62 mmol) was added and the mixture was stirred at room temperature for 1 hour. 20 mL of water was added into the mixture, and then the organic layer was isolated, washed with 20 mL of water then dried over MgSO4. The solvent was removed in vacuo to give 180 mg of the title compound as an orange gum $^1$H NMR (CDCl$_3$) ☐ 9.55 (s broad, 1H), 9.4 (s broad, 1H), 7.4-7.2 (m, 10H), 6.19 (s, 1H), 4.8 (d, 2H), 4.55 (d, 2H), 3.6 (m, 4H), 3.45 (m, 2H), 3.3 (s, 2H), 2.35 (m, 4H). LRMS (ES$^+$) m/z 434 [MH]$^+$ Preparation 45

N-2,N-4-dibenzyl-6-morpholin-4-yl-methyl-pyridine-2,3,4-triamine

N-2,N-4-dibenzyl-6-morpholin-4-yl-methyl-3-nitro-pyridine-2,4-diamine (190 mg, 0.43 mmol) was dissolved in 30 mL of methanol and Raney nickel (40 mg, 20% weight) was added, then the mixture was stirred at room temperature under 80 psi of hydrogen for 1 hour. After completion, the mixture was filtered through arbocel and the solvent was removed in vacuo to give 180 mg of the title compound as a green oil.

$^1$H NMR (CD$_3$OD): ☐ 7.4-7.2 (m, 10H), 6.1 (s, 1H), 4.6 (d, 2H), 4.4 (d, 2H), 3.3 (m, 6H), 2.4-2.2 (s broad, 2H), 2.15 (m, 4H). LRMS (ES$^+$) m/z 417 [MH]$^+$ Preparation 46

N-2,N-4-dibenzyl-6-ethyl-pyridine-2,3,4-triamine

N-2,N-4-dibenzyl-3-nitro-6-vinyl-pyridine-2,4-diamine (300 mg, 0.75 mmol) was dissolved in 20 mL of tetrahydrofuran and Raney nickel (40 mg, 13% weight) was added, then the mixture was stirred at room temperature under 60 psi of hydrogen for 1.5 hour. After completion, the mixture was filtered through arbocel and the solvent was removed in vacuo to give 230 mg of the title compound.

$^1$H NMR (CDCl$_3$): ☐ 7.40-7.20 (m, 5H), 6.0 (s, 1H), 4.90-4.80 (s broad, 2H), 4.65 (d, 2H), 4.35 (d, 2H), 2.55 (q, 2H), 1.20 (t, 3H).

Preparation 47

1-(4,6-bis-benzylamino-5-nitro-pyridin-2-yl)-ethanone

N-2,N-4-dibenzyl-6-bromo-3-nitro-pyridine-2,4-diamine (800 mg, 1.94 mmol) was dissolved in 40 mL of tetrahydrofuran then (1-ethoxyvinyl)-tri-n-butyltin (909 mg, 2.52 mmol) was added followed by palladium acetate (90 mg, W/W) and triphenylphosphine (100 mg, w/w) and the mixture was stirred at 80° C. for 1 hour. Once the reaction was complete, 30 mL of ethyl acetate and 40 mL of a solution of HCl 3N were added. The mixture is vigorously stirred for 30 minutes at 60° C. The organic layer was separated, washed with 50 mL of brine and the solvent was removed in vacuo. The crude residue was purified by column chromatography on silica gel using 10% of ethyl acetate in pentane to give 680 mg of the title compound as a yellow solid.

$^1$H NMR (CDCl$_3$): ☐ 9.55 (s broad, 1H), 9.35 (s broad, 1H), 7.40-7.0 (m, 10H), 6.75 (s, 1H), 5.25 (s, 1H), 4.85 (d, 2H), 4.55 (d, 2H), 2.50 (s, 3H). LRMS (ES$^+$) m/z 377 [MH]$^+$ Preparation 48

N-2,N-4-dibenzyl-6-difluoromethyl-3-nitro-pyridine-2,4-diamine 4,6-bis-benzylamino-5-nitro-pyridine-2-carbaldehyde (250 mg, 0.69 mmol) was dissolved in 15 mL of dichloromethane and cooled down to 0° C. then bis-(2-methoxyethyl)aminosulphur trifluoride (611 mg, 2.76 mmol) was added and the reaction mixture was stirred at room temperature for 3 hours. Once the reaction was complete, 30 mL of water was added into the mixture, and then the organic layer was isolated, washed with 30 mL of a saturated solution of potassium carbonate, and brine then dried over MgSO4. The solvent was removed in vacuo and the crude residue was purified by column chromatography on silica gel using 10% of ethyl acetate in pentane to give 220 mg of the title compound as a yellow solid.

$^1$H NMR (CDCl$_3$) ☐ 9.60 (s broad, 1H), 9.3 (s broad, 1H), 7.4-7.2 (m, 10H), 6.30 (s, 1H), 6.35-6.05 9t, 1H), 6.75 (d, 2H), 6.50 (d, 2H). LRMS (ES$^+$) m/z 385 [MH]$^+$ Preparation 49

4,6-bis-benzylamino-5-nitro-pyridine-2-carbonitrile

N-2,N-4-dibenzyl-6-bromo-3-nitro-pyridine-2,4-diamine (500 mg, 1.21 mmol) was suspended in 10 mL of toluene then tributyltin cyanide (765 mg, 2.42 mmol) was added followed by palladium acetate (60 mg, W/W) and triphenylphosphine (70 mg, w/w) and the mixture was microwaved at 130° C. for 25 minutes. Once the reaction was complete, the solvent was removed in vacuo and the crude residue was purified by column chromatography on silica gel using 10% of ethyl acetate in pentane to give 408 mg of the title compound as a yellow solid.

$^1$H NMR (CDCl$_3$): ☐ 9.65 (s broad, 1H), 9.30 (s broad, 1H), 7.40-7.20 (m, 10H), 6.40 (s, 1H), 4.75 (d, 2H), 4.50 (d, 2H). LRMS (ES$^+$) m/z 360 [MH]$^+$ Preparation 50

(4,6-bis-benzylamino-5-nitro-pyridin-2-yl)-methanol

N-2,N-4-dibenzyl-6-bromo-3-nitro-pyridine-2,4-diamine (315 mg, 0.87 mmol) was suspended in 20 mL of tetrahydrofuran and cooled down to 0° C. then sodium borohydride (40 mg, 1.1 mmol) and the mixture was stirred at 0° C. for 15 minutes. The mixture was partitioned in water (10 mL) and ethyl acetate (10 mL). The organic layer was isolated, washed with 15 mL of brine, dried over magnesium sulfate and the solvent was removed in vacuo to give 315 mg of the title compound as a yellow solid $^1$H NMR (CDCl$_3$): ☐ 9.50 (s broad, 1H), 7.40-7.20 (m, 10H), 5.85 (s, 1H), 4.59 (d, 2H), 4.45 (d, 2H), 4.35 (s, 2H). LRMS (ES$^+$) m/z [MH]$^+$ Preparation 51

N-2,N-4-dibenzyl-6-bromomethyl-3-nitro-pyridine-2,4-diamine (4,6-bis-benzylamino-5-nitro-pyridin-2-yl)-methanol (300 mg, 0.82 mmol) was dissolved in 20 mL of dichloromethane and cooled down to 0° C. then triphenylphosphine (237 mg, 0.91 mmol) was added followed by N-bromosuccinimide (161 mg, 0.82 mmol) and the mixture was stirred at 0° C. for 30 minutes then warmed to room tempereature and stirred for 2 hours. The solvent was removed in vacuo and the crude residue was purified by column chromatography on silica gel using 20% of ethyl acetate in pentane to give 220 mg of the title compound as a yellow solid.

$^1$H NMR (CDCl$_3$): ☐ 9.59 (s broad, 1H), 9.40 (s broad, 1H), 7.40-7.20 (m, 10H), 6.15 (s, 1H), 4.80 (d, 2H), 4.55 (d, 2H), 4.15 (s, 2H). LRMS (ES$^+$) m/z 427,429 [MH]$^+$ Preparation 52

N-2,N-4-dibenzyl-6methoxymethyl-3-nitro-pyridine-2,4-diamine

N-2,N-4-dibenzyl-6-bromomethyl-3-nitro-pyridine-2,4-diamine (100 mg, 0.23 mmol) was dissolved in 10 mL of methanol then sodium methoxide (25 mg, 0.46 mmol) was added followed was stirred at 60° C. overnight. The solvent was removed in vacuo and the crude was partitioned in 10 mL of dichloromethane and 10 mL of water. The organic layer was isolated, dried over magnesium sulfate and the solvent removed in vacuo to give 80 mg of the title compound as a yellow solid.

NMR (CDCl$_3$): ☐ 9.59 (s broad, 1H), 9.40 (s broad, 1H), 7.40-7.20 (m, 10H), 6.20 (s, 1H), 4.80 (d, 2H), 4.55 (d, 2H), 4.25 (s, 2H), 3.35 (s, 3H). LRMS (ES$^+$) m/z 379 [MH]$^+$ Preparation 53

N-2,N-4-Dibenyl-3-nitro-6-pyrazin-2-yl-pyridine-2,4-diamine

N-2,N-4-Dibenyl-6-bromo-3-nitro-pyridine-2,4-diamine (100 mgs/0.242 mmols), 2-Tri-n-butylstannylpyrazine (116 mgs/0.315 mmols), palladium acetate (15 mgs) and triphenylphosphine (20 mgs) were dissolved in toluene (2 mls) and subjected to microwave irradiation at 130° C. for 25 mins in a Biotage Initiator. The reaction was repeated on the same scale on two more occasions. The three reactions were combined, diluted with EtOAc (10 mls), washed with water (5 mls) and concentrated in vacuo. Purification by column chromatography eluting with 10:1 Pentane:EtOAc gave the title compound (105 mgs) as a yellow solid.

$^1$H NMR (CDCl3, 400 MHz) ☐ 4.60-4.65 (d, 2H), 4.90-4.95 (d, 2H), 7.20-7.40 (mult, 10H), 8.55-8.60 (mult, 2H), 9.40-9.50 (mult, 2H), 9.60 (mult, 1H); LRMS (ESCI) m/z 413 [MH]$^+$.

Preparation 54

N-2,N-4-Dibenzyl-6-pyrazin-2-yl-pyridine-2,3,4-triamine

N-2, N-4-Dibenyl-3-nitro-6-pyrazin-2-yl-pyridine-2,4-diamine (105 mgs/0.255 mmols) was dissolved in MeOH (20 mls)/THF (20 mls). Raney Nickel (30 mgs) was added and the reaction placed under 80 psi hydrogen at room temperature for 5 hours. Filtered through celite and concentrated in vacuo to give the title compound (95 mgs) as a pale green oil LRMS (ESCI) m/z 383 [MH]+, 381 [MH]−.

Preparation 55

6-Allyl-N2,N4-dibenzyl-3-nitro-pyridine-2,4-diamine

N*2*,N*4*-Dibenzyl-6-bromo-3-nitro-pyridine-2,4-diamine (1 g, 2.4 mmol) was stirred in anhydrous tetrahydrofuran (20 ml) and the solution degassed with nitrogen prior to the addition of palladium acetate (109 mg, 0.48 mmol) and allyltributyltin (1.1 ml, 3.6 mmol). The reaction mixture was degassed for 10 minutes before heating the suspension at 80° C. for 16 h. The suspension was cooled to ambient temperature, concentrated in vacuo and purified directly by column chromatography on silica, eluting with pentane:EtOAc, 9:1 to afford the title compound as a yellow solid, (696 mg, 77%)

$^1$H NMR (CDCl$_3$) ☐ 3.23-3.25 (d, 2H), 4.47-4.49(d, 2H), 4.81-4.82(d, 2H), 5.07-5.14(m, 2H), 5.89-5.99(m, 1H), 7.29-7.40 (m, 11H); LRMS (ES) m/z 375 [MH]+

Preparation 56

(4,6-Bis-benzylamino-5-nitro-pyridin-2-yl)-acetaldehyde

6-Allyl-N2,N4-dibenzyl-3-nitro-pyridine-2,4-diamine (1.0 g, 2.7 mmol) was suspended in a mixture of 15 ml tetrahydrofuran and 30 ml water. Upon the addition of potassium osmate (148 mg, 0.4 mmol) and sodium periodate (1.17 g, 5.4 mmol), the solution was stirred vigorously at room temperature for 30 minutes. Ethyl acetate (20 ml) was added to the reaction mixture and the phases partitioned, the organic extract dried over magnesium sulphate, concentrated in vacuo and purified by column chromatography on silica, eluting with 100% EtOAc to afford 3-(4,6-Bis-benzylamino-5-nitro-pyridin-2-yl)-propane-1,2-diol (992 mg, 91%). The intermediate diol was stirred in 20 ml acetone in the presence of sodium periodate (1.17 g, 5.5 mmol). After 2 h the solution was partitioned between EtOAc and water, the organic extract dried (MgSO$_4$) and concentrated to give the title compound as an orange oil, (962 mg, 96%).

1H NMR (CDCl$_3$) ☐ 3.49(d, 2H), 4.49-4.50(d, 2H), 4.65-4.66(d, 2H), 7.52-7.90(m, 11H), 10.03(s, 1H); LCMS (APCI+) RT@3.74 min, m/z 409 [MH]+

Preparation 57

2-(4,6-Bis-benzylamino-5-nitro-pyridin-2-yl)-ethanol (4,6-Bis-benzylamino-5-nitro-pyridin-2-yl)-acetaldehyde (250 mg, 0.66 mmol) was stirred in 15 ml dichloromethane. Sodium borohydride (38 mg, 0.99 mmol) was added and the solution stirred at ambient temperature overnight. The reaction mixture was partitioned between DCM and water, the organics dried over magnesium sulphate and concentrated to give a crude solid which was purified by column chromatography on silica, eluting with pentane:EtOAc, 4:1 to 1:1 to afford the title compound as a yellow solid, (134 mg, 53%).

$^1$H NMR (CDCl$_3$) ☐ 2.68-2.70 (t, 2H), 3.83-3.86 (t, 2H), 4.49-4.51 (d, 2H), 4.72-4.74 (d, 2H), 5.86 (s, 1H), 7.29-7.38 (m, 10H), 9.50-9.54 (bd, 2H); LRMS (ES) m/z 379 [MH]+

Preparation 58

N2,N4-Dibenzyl-6-(2-methoxy-ethyl)-3-nitro-pyridine-2,4-diamine 2-(4,6-Bis-benzylamino-5-nitro-pyridin-2-yl)-ethanol (134 mg, 35 mmol), was suspended in a mixture of dichloromethane (15 ml) and triethylamine (59 µl, 0.43 mmol) and the solution cooled to 5° C. in an ice bath. Methanesulphonyl chloride (33 µl, 0.43 mmol) was added and the reaction mixture stirred at ambient temperature for 1 h. A further 10 ml DCM was added, the organics washed with 2×K$_2$CO$_3$ (10% aq solution), dried and concentrated to afford a crude oil. The intermediate mesylate was suspended in acetone (20 ml) and sodium methoxide added (96 mg, 1.7 mmol), heating the mixture at reflux for 1 h. Residual solvent was removed in vacuo, DCM added and the solution washed with 2×H$_2$O. The combined organics were dried over MgSO$_4$, concentrated and purified by column chromatography on silica, eluting with Pent:EtOAc, 8:1 to 4:1 to afford the title compound as a yellow oil, (68 mg, 47%).

$^1$H NMR (CDCl$_3$) ☐ 2.70-2.73(t, 2H), 3.26(s, 3H), 3.64-3.67(t, 2H), 4.49-4.50 (d, 2H), 4.81-4.82(d, 2H), 5.91(s, 1H), 7.29-7.39(m, 10H), 9.40-9.48(bd, 2H); LRMS (ES) m/z 393 [MH]+

Preparation 59

N*2*,N*4*-Dibenzyl-6-(2-methoxy-ethyl)-pyridine-2,3,3-triamine

N*2*,N*4*-Dibenzyl-6-(2-methoxy-ethyl)-3-nitro-pyridine-2,4-diamine (65 mg, 0.17 mmol) was stirred in THF (10 ml) in the presence of Raney Nickel (20% wt, 13 mg). The mixture was stirred at RT, 60 psi H$_2$ for 2 h then filtered through an Arbocel pad, washing with 2×THF. The filtrate was concentrated in vacuo to give the title compound as a brown oil, (47 mg, 78%), which was used immediately in the following step with no further purification.

LRMS (ES) m/z 363 [MH]+

Preparation 60

1-Benzyl-4-benzylamino-6-(2-methoxy-ethyl)-1,3-dihydro-imidazo[4,5-c]pyridine-2-one N*2*,N*4*-Dibenzyl-6-(2-methoxy-ethyl)-pyridine-2,3,3-triamine (47 mg, 0.13 mmol) was stirred in acetonitrile (5 ml). N,N-Carbodiimidazole was added, (105 mg, 0.65 mmol) and the mixture heated at reflux for 16 h. The solution was concentrated in vacuo and purified directly by column chromatography on silica, eluting with 100% DCM to 96:4 to afford the title compound as a pale brown solid, (32 mg, 64%) present as a 3:2 mixture with the isomeric 1-deazapurine.

LRMS (ES) m/z 389 [MH]+

Preparation 61

N2,N4-Dibenzyl-6-[2-(2-methoxy-ethylamino)-ethyl]-3-nitro-pyridine-2,4-diamine

N*2*,N*4*-Dibenzyl-3-nitro-6-vinyl-pyridine-2,4-diamine (50 mg, 0.14 mmol) was suspended in 2-methoxy-ethylamine (1 ml) and the mixture refluxed for 1 h. Excess reagents were removed in vacuo, the residue dissolved in DCM (10 ml), washed with 2×H$_2$O, dried and concentrated. The crude material was purified by column chromatography on silica, eluting with DCM:MeOH, 92:8 to give the title compound as a yellow oil, (58 mg, 96%).

$^1$H NMR (CDCl$_3$) ☐ 2.75-2.80 (m, 4H), 2.96-3.00 (t, 2H), 3.29 (s, 3H), 3.48-3.51 (t, 2H), 4.48-4.49 (d, 2H), 4.76-4.78 (d, 2H), 5.87 (s, 1H), 7.27-7.40 (m, 10H), 9.41-9.51 (dt, 2H); LRMS (ES) m/z 436 [MH]+

Preparation 62

[2-(4,6-Bis-benzylamino-5-nitro-pyridin-2-yl)-ethyl]-(2-methoxy-ethyl)-carbamic acid tert-butyl ester N*2*,N*4*-Dibenzyl-6-[2-(2-methoxy-ethylamino)-ethyl]-3-nitro-pyridine-2,4-diamine (150 mg, 0.34 mmol) was suspended in DCM (10 ml) and the solution cooled to 0° C. before the drop-wise addition of boc anhydride (95 μl, 0.41 mmol) as a solution in 5 ml DCM. The mixture was allowed to warm to room temperature and after 1 h, quenched with 10 ml H$_2$O. The organic extract was dried and concentrated in vacuo to give the title compound as a yellow oil, (170 mg, 92%).

1H NMR (CDCl$_3$) ☐ 1.41 (s, 9H), 2.68(t, 2H), 3.30(s, 3H), 3.42(bs, 2H), 3.50 (m, 4H), 4.47-4.48(d, 2J), 4.80-4.81 (d, 2H), 5.82(s, 1H), 7.24-7.39(m, 10H); LRMS (ES) m/z 536 [MH]+

Preparation 63

N2,N4-Dibenzyl-3-nitro-6-oxazol-2-yl-pyridine-2,4-diamine

Butyl lithium (12.8 ml, 20.5 mmol) was added drop-wise to a stirred solution of oxazole (1.13 ml, 17.1 mmol) in dry THF (20 ml) at −78° C. (dry ice/acetone bath), keeping the addition rate slow so that the reaction temperature did not go above −60° C. The solution was stirred at this temperature for 10 minutes then a solution of zinc chloride (5.00 g, 36.7 mmol) in THF (30 ml) was added drop-wise. The solution was stirred for 15 minutes at −78° C. then the cooling bath was removed and the reaction mixture allowed to warm to RT.

An aliquot (19 ml) of the reaction mixture was added via a syringe to a pre-sealed and nitrogen purged microwave vial (Biotage, 10-20 ml) containing N*2*,N*4*-dibenzyl-6-bromo-3-nitro-pyridine-2,4-diamine (1.11 g, 2.68 mmol) and palladium bis(triphenylphosphine)dichloride (373 mg, 0.53 mmol). The vial was heated under microwave irradiation (Biotage, Initiator 8) for 15 minutes at 130° C. The reaction mixture was concentrated in vacuo then partitioned between 2-methyl THF (80 ml) and saturated ammonium chloride solution (80 ml). The mixture was filtered then transferred to a separating funnel. The layers were separated then the aqueous was extracted with more 2-methyl THF (50 ml). The combined organics were dried (MgSO$_4$) and evaporated. The brown solid obtained was triturated with EtOAc and the solid collected by filtration then washed with EtOAc to yield the product as a brown solid (1.03 g, 96%).

$^1$H NMR (CDCl3) ☐ 4.59 (d, J=5.47 Hz, 2H) 4.91 (d, J=5.47 Hz, 2H) 6.93 (s, 1H) 7.21-7.47 (m, 11H) 7.78 (s, 1H) 9.31-9.44 (m, 1H) 9.54-9.63 (m, 1H). LRMS (ES$^+$) m/z 402 [MH]$^+$

Preparation 64

N2,N4-Dibenzyl-6-oxazol-2-yl-pyridine-2,3,4-triamine

N*2*,N*4*-Dibenzyl-3-nitro-6-oxazol-2-yl-pyridine-2,4-diamine (1.02 g, 2.54 mmol) was dissolved in THF (60 ml) then MeOH (60 ml) was added. The solution was hydrogenated over Raney nickel (210 mg, 0.25 mmol) under a hydrogen atmosphere (80 psi) for 1 hour. The reaction mixture was filtered through a Celite pad then evaporated to yield the title compound as a brown gum (944 mg, 100%). Taken on without further purification due to stability concerns.

LCMS R$_t$=2.41 m/z 372 [MH]$^+$

Preparation 65

N2,N4-Dibenzyl-6-(1-methyl-1H-imidazol-2-yl)-3-nitro-pyridine-2,4-diamine

N-Methylimidazole (0.728 ml, 9.18 mmol) was dissolved in dry THF (25 ml) then the solution was cooled to −15° C. (ice/salt bath). n-Butyl lithium in hexane (6.31 ml, 10.1 mmol) was added drop-wise to the solution (colour changed from colourless to yellow). The solution was left to stir for 1 hour at −15° C. then a solution of anhydrous zinc chloride (5.00 g, 36.7 mmol) in dry THF (35 ml) was adder drop-wise. The solution was stirred at −15° C. for 1 hour then allowed to warm slowly to RT then stirred for 1 more hour.

An aliquot (16 ml) of the solution was added to a pre-sealed and nitrogen purged microwave vial (Biotage, 2.0-5.0 ml), which contained N*2*,N*4*-dibenzyl-6-bromo-3-nitro-pyridine-2,4-diamine (400 mg, 0.968 mmol) and palladium bis(triphenylphosphine)dichloride (136 mg, 0.193 mmol). The vial was heated under microwave irradiation (Biotage Initiator 8) for 15 minutes at 130° C. The reaction mixture was concentrated in vacuo. The residue was partitioned between EtOAc (15 ml) and 2 M ammonia solution (15 ml). The majority of the aqueous phase was removed using a separating funnel (small amount of emulsion between layers). The organic layers were washed with more 2 M ammonia solution (15 ml) then brine (15 ml) then dried ($MgSO_4$) and evaporated. The crude was columned on Isco Companion on a silica column (12 g, Redisep). Eluted with EtOAc:heptane, increasing the gradient linearly from 20:80 to 60:40 over 8 column volumes, then isocratic at 60:40 for 4 column volumes. The desired fractions were combined and evaporated to yield the title compound as a yellow solid (240 mg, 60%).

$^1$H NMR (CD3OD) ☐3.88 (s, 3H) 4.67 (d, J=5.48 Hz, 2H) 4.83 (d, J=5.48 Hz, 2H) 6.92 (d, J=1.17 Hz, 1H) 7.14 (d, J=1.17 Hz, 1H) 7.17 (s, 1H) 7.26-7.42 (m, 10H) 9.43-9.66 (m, 2H). LRMS ($ES^+$) m/z 415 $[MH]^+$

Preparation 66

N2,N4-Dibenzyl-6-(1-methyl-1H-imidazol-2-yl-pyridine-2,3,4-triamine

N*2*,N*4*-Dibenzyl-6-(1-methyl-1H-imidazol-2-yl)-3-nitro-pyridine-2,4-diamine (0.235 g, 0.567 mmol) was dissolved in THF (10 ml) then MeOH (10 ml) was added. The solution was hydrogenated over Raney nickel (0.050 g, 0.58 mmol) under a hydrogen atmosphere (80 psi) for 1 hour. The reaction mixture was filtered through a Celite pad then evaporated to yield the title compound as a pale green solid (218 mg, 100%). Taken on without further purification due to stability concerns.

LCMS $R_t$=2.22 m/z 385 $[MH]^+$

Preparation 67

(2,6-Dibromo-3-nitro-pyridin-4-yl)-carbamic acid ethyl ester

A solution of ethyl chloroformate (5.96 g) in anhydrous 2-methyl THF (50 ml) was added drop-wise to a solution of 2,6-dibromo-3-nitro-pyridin-4-ylamine (15.00 g) and triethylamine (10.1 g) in anhydrous 2-methyl THF (100 ml) at 0° C., keeping the addition rate such that the reaction temperature did not rise above 5° C. The reaction mixture was allowed to warm to room temperature then left to stir under nitrogen for 1 hour. A further portion of ethyl chloroformate (0.54 g) was added and the mixture was left to stir for a further 1 hour. Water (50 ml) was added and the layers separated. The aqueous layer was extracted with EtOAc (50 ml) and the combined organics were dried ($MgSO_4$) and evaporated to a brown solid. This solid was pre-absorbed onto silica (~19 g) then columned on Isco Companion on a silica column (330 g, Redisep), eluting with EtOAc:heptane. The gradient was kept isocractic at 10:90 for 1 column volume (CV), then increased linearly from 10:90 to 30:70 over 6 CVs. This provided the title compound (12.6 g) as a pale yellow foamy solid.

1H NMR (400 MHz, CHLOROFORM-d) δ ppm 1.36 (t, J=7.10 Hz, 3 H), 4.26 (q, =7.10 Hz, 2 H), 7.95 (br, s, 1 H), 8.59 (s, 1 H), LCMS $R_t$=3.22 m/z 368, 370, 372 $[MH]^+$ Preparation 68

(2,6-Dibromo-3-nitro-pyridin-4-yl)-(6-methyl-pyridin-3-ylmethyl)-carbamic acid ethyl ester Potassium carbonate (7.95 g) was added to a stirred solution of (2,6-dibromo-3-nitro-pyridin-4-yl)-carbamic acid ethyl ester (10.62 g) in acetone (100 ml). 5-(chloromethyl)-2-methylpyridine (4.89 g) was then added, followed by sodium iodide (5.18 g). The mixture was left to stir under nitrogen for 18 hours. The reaction mixture was filtered, concentrated in vacuo, and then partitioned between ethyl acetate (100 ml) and water (100 ml). The organics were dried ($MgSO_4$) and evaporated to a dark purple gum, which was columned on Isco Companion on a silica column (330 g, Redisep), eluting with EtOAc:heptane, increasing the gradient linearly from 40:60 to 80:20 over 6 column volumes. This provided the title compound (8.5 g) as a green gum which solidified to a pale green solid on standing.

1H NMR (400 MHz, CHLOROFORM-d) δ ppm 1.24 (t, J=7.10 Hz, 3 H) 2.59 (s, 3 H) 4.19 (q, J=7.10 Hz, 2 H) 4.79 (s, 2 H) 7.17 (s, 1 H) 7.19 (d, J=8.20 Hz, 1 H) 7.57 (dd, J=8.20, 2.34 Hz, 1 H) 8.38 (d, J=2.34 Hz, 1 H), LCMS $R_t$=2.44 m/z 473, 475, 477 $[MH]^+$ Preparation 69

(2-Amino-6-bromo-3-nitro-pyridin-4-yl)-(6-methyl-pyridin-3-ylmethyl)-carbamic acid ethyl ester (2,6-Dibromo-3-nitro-pyridin-4-yl)-(6-methyl-pyridin-3-ylmethyl)-carbamic acid ethyl ester (6.00 g) was dissolved in 2-methyltetrahydrofuran (60 ml). The solution was split equally into 3 sealable vessels (Biotage, 10-20 ml). Aqueous ammonia solution (0.88 g $cm^{-3}$, 20 ml) was added to each vial (60 ml total). The vials were sealed then the bi-phasic mixtures were left to stir vigorously at room temperature overnight. The three reaction mixtures were combined and transferred to a separating funnel. Ethyl acetate (120 ml) and water (120 ml) were added. The phases were separated then the organics were washed with brine (100 ml). The organics were dried ($MgSO_4$) then evaporated to a brown gum. The gum was re-dissolved in diethyl ether, then evaporated to provide the title compound (5.4 g) as a foamy yellow solid.

1H NMR (400 MHz, CHLOROFORM-d) δ ppm 1.16-1.27 (m, 3 H) 2.58 (s, 3 H) 4.10-4.21 (m, 2 H) 4.87 (s, 2 H) 6.34 (s, 2 H) 6.61 (s, 1 H) 7.18 (d, J=8.19 Hz, 1 H) 7.66 (s, 1 H) 8.41 (d, J=2.34 Hz, 1 H), LCMS $R_t$=1.94 m/z 412 $[MH]^+$ Preparation 70

[2-Amino-6-(4-methyl-oxazol-2-yl)-3-nitro-pyridin-4-yl]-(6-methyl-pyridin-3-ylmethyl)-carbamic acid ethyl ester Butyl lithium (1.6 M in hexane, 366 μl) was added drop-wise to a stirred solution of 4-methyloxazole (41 mg) in THF (0.5 ml) in a ReactiVial at −78° C. (dry ice/acetone bath). The solution was stirred at this temperature for 10 minutes then a solution of zinc chloride (199 mg) in THF (1 ml) was added drop-wise. The solution was stirred for 15 minutes at −78° C.

then the cooling bath removed and the reaction mixture allowed to warm to room temperature. This zinc oxazole solution was then added via syringe to a pre-sealed and nitrogen purged microwave vial (Biotage, 0.5-2.0 ml) containing (2-Amino-6-bromo-3-nitro-pyridin-4-yl)-(6-methyl-pyridin-3-ylmethyl)-carbamic acid ethyl ester (100 mg) and palladium bis(triphenylphosphine)dichloride (34 mg). The vial was heated under microwave irradiation (Biotage, Initiator 8) for 15 minutes at 60° C. The reaction mixture was then partitioned between ethyl acetate (10 ml) and a saturated aqueous solution of ammonium chloride (10 ml). The layers were separated and the aqueous extracted with ethyl acetate (10 ml). The combined organics were washed with brine (10 ml) then dried ($MgSO_4$) and evaporated. The crude was columned on Isco Companion on a silica column (12 g, Redisep), eluting with ethyl acetate for 4 column volumes (CV), then the gradient increased linearly from 0-5% methanol in ethyl acetate over 10 CV. This provided the title compound (69 mg) as a yellow gum.

1H NMR (400 MHz, CHLOROFORM-d) δ ppm 1.11-1.25 (m, 3 H) 2.28 (s, 3 H) 2.56 (s, 3 H), 4.13-4.23 (m, 2 H) 4.96 (s, 2 H) 6.37 (s, 2 H) 7.16 (d, J=7.80 Hz, 1 H) 7.26 (s, 1 H) .53 (s, 1 H) 7.65-7.78 (m, 1 H) 8.43 (s, 1 H), LCMS $R_t$=1.86 m/z 413 $[MH]^+$ Preparation 71

5-Ethyl-oxazole

Ethyl-5-ethyloxazole-4-carboxylate (3.5 g) was dissolved in ethanol (45 ml) and a solution of sodium hydroxide (2.07 g) in water (18 ml) added. The reaction was stirred at room temperature for 16 hours. The reaction mixture was reduced to ~20 ml, and then concentrated hydrochloric acid added to give a pH of ~1-2. The reaction mixture was extracted with $CH_2Cl_2$ 3×30 ml. The combined organic extracts were washed with saturated brine, dried over $Na_2SO_4$, filtered and evaporated to give a pale yellow solid. This was taken up in quinoline (3 ml) and 100 mg of copper (II) oxide was added. The reaction was then heated (oil bath 160° C.) under slightly reduced pressure and a clear liquid distilled over at ~60-70° C. This provided the title compound (790 mg) as a clear oil.

1H NMR (400 MHz, CHLOROFORM-d) δ ppm 1.2 (t, 3 H), 2.6 (q, 2 H), 6.65 (s, 1 H), 7.7 (s, 1 H)

Preparation 72

[2-Amino-6-(5-ethyl-oxazol-2-yl)-3-nitro-pyridin-4-yl]-(6-methyl-pyridin-3-ylmethyl)-carbamic acid ethyl ester The title compound was prepared following the example in preparation 70, using 5-ethyl-oxazole (47 mg) and (2-amino-6-bromo-3-nitro-pyridin-4-yl)-(6-methyl-pyridin-3-ylmethyl)-carbamic acid ethyl ester (100 mg), giving the product (79 mg) as a yellow gum.

1H NMR (400 MHz, CHLOROFORM-d) δ ppm 1.13-1.25 (m, 3 H) 1.33 (t, J=7.61 Hz, 3 H) 2.56 (s, 3 H) 2.80 (q, J=7.41 Hz, 2 H) 4.13-4.22 (m, 2 H) 4.96 (s, 2 H) 6.31-6.45 (m, 2 H) 6.97 (s, 1 H) 7.16 (d, J=7.80 Hz, 1 H) 7.26 (s, 1 H) 7.63-7.79 (m, 1 H) 8.43 (s, 1 H), LCMS $R_t$=2.16 m/z 427 $[MH]^+$ Preparation 73

5-Isopropyl-oxazole-4-carboxylic acid ethyl ester

Ethyl isocyanoacetate (4.52 g) was added drop-wise to a stirred suspension of KOtBu in THF (35 ml) at 0° C. under nitrogen. After complete addition, the dark brown solution was stirred for 30 minutes and then a solution of isobutyryl chloride (2.1 ml) in THF (15 ml) added drop-wise, keeping the temperature below ~10° C. The reaction was stirred for 1 hour then evaporated to dryness. The residue was treated with acetic acid (1.14 ml) and water (25 ml), and then extracted with ether (3×30 ml). The combined ether extracts were washed with saturated brine, dried over sodium sulfate, filtered and evaporated to give a brown oil that was purified by column chromatography, eluting with 1% MeOH in dichloromethane. This gave the title compound (1.91 g) as a colourless oil.

1H NMR (400 MHz, CHLOROFORM-d) δ ppm 1.25 (d, 6 H), 1.38 (t, 3 H), 3.8 (m, 1 H), 4.35 (q, 2 H), 7.7 (s, 1 H), LRMS m/z (API) 184 $[MH]^+$, 367 $[2MH]^+$ Preparation 74

5-Isopropyl-oxazole

5-Isopropyl-oxazole-4-carboxylic acid ethyl ester (1.89 g) was taken up in a solution of 1N sodium hydroxide (10 ml) and ethanol (0.5 ml) and the mixture stirred at room temperature for 16 hours. A solution of 1N HCl (approx 9 mll) was added and the mixture stirred for a few minutes. A white solid crystallized out and was collected by filtration. After drying, this solid was taken up in quinoline (3 ml) and copper oxide (120 mg) added. The reaction was heated under vacuum, slowly increasing the oil bath temperature to ~170° C. A clear liquid distilled out giving a mixture of the desired product and quinoline. This oil was then re-distilled at lower pressure (~180 mBar) and temperature (70° C.) providing the title compound (260 mg) as a clear oil.

1H NMR (400 MHz, CHLOROFORM-d) δ ppm 1.24 (d, 6 H), 2.96 (m, 1 H), 6.7 (s, 1 H), 7.7 (s, 1 H)

Preparation 75

[2-Amino-6-(5-isopropyl-oxazol-2-yl)-3-nitro-pyridin-4-yl]-(6-methyl-pyridin-3-ylmethyl)-carbamic acid ethyl ester The title compound was prepared following the example in preparation 70, using 5-isopropyl-oxazole (54 mg) and (2-amino-6-bromo-3-nitro-pyridin-4-yl)-(6-methyl-pyridin-3-ylmethyl)-carbamic acid ethyl ester (100 mg), giving the product (48 mg) as a yellow gum.

1H NMR (400 MHz, CHLOROFORM-d) δ ppm 1.13-1.26 (m, 3 H) 1.34 (d, J=6.63 Hz, 6 H) .56 (s, 3 H) 3.04-3.15 (m, 1 H) 4.10-4.23 (m, 2 H) 4.96 (s, 2 H) 6.39 (s, 2 H) 6.94 (s, 1 H) 7.16 (d, J=7.80 Hz, 1 H) 7.21 (s, 1 H) 7.63-7.76 (m, 1 H) 8.43 (s, 1 H), LCMS $R_t$=2.30 m/z 441 $[MH]^+$ Preparation 76

[2-Amino-6-(4,5-dimethyl-oxazol-2-yl)-3-nitro-pyridin-4-yl]-(6-methyl-pyridin-3-ylmethyl)-carbamic acid ethyl ester The title compound was prepared following the example in preparation 70, using 4,5-dimethyl-oxazole (47 mg) and (2-amino-6-bromo-3-nitro-pyridin-4-yl)-(6-methyl-pyridin-3-ylmethyl)-carbamic acid ethyl ester (100 mg), giving the product (75 mg) as a yellow gum.

1H NMR (400 MHz, CHLOROFORM-d) δ ppm 1.03-1.26 (m, 3 H) 2.19 (s, 3 H) 2.37 (s, 3 H) 2.56 (s, 3 H) 4.09-4.26 (m, 2 H) 4.95 (s, 2 H) 6.40 (s, 2 H) 7.16 (d, J=7.80 Hz, 1 H) 7.21 (s, 1H) 7.62-7.83 (m, 1 H) 8.42 (s, 1 H), LCMS $R_t$=2.12 m/z 427 [MH]$^+$

Preparation 77

Oxazol-4-yl-methanol

DIBAL-H (56 ml of a 1.0 M solution in toluene) was added drop-wise over 15 minutes to a solution of oxazole-4-carboxylic acid ethyl ester (7.50 g, 53.1 mmol) in THF (140 ml) at −78° C. The resulting solution was stirred at −78° C. for 30 min and then further DIBAL-H (56 mL of a 1.0 M solution in toluene, 56.0 mmol) was added over 15 minutes. The reaction was then left to slowly warm from −78° C. to room temperature for 16 hours. The resulting bright yellow solution was cooled to 0° C. in an ice bath and Na2SO4.10 H2O (15.9 g—equal weight to DIBAL-H added) was added in small portions (CARE—slow addition to prevent exotherm) to cause precipitation of aluminium salts. The mixture was left to warm to room temperature and after stirring for 90 mins the resulting suspension was filtered through a layer of celite. The celite plug was rinsed with dichloromethane (3×100 mL) and methanol (2×100 mL) and the filtrates were combined. The solvent was removed under reduced pressure, providing the title compound (4.8 g) as a brown oil.

1H NMR (400 MHz, CHLOROFORM-d) δ ppm 4.60 (s, 2 H), 7.6 (s, 1 H), 7.9 (s, 1 H)

Preparation 78

4-Methoxymethyl-oxazole

Oxazol-4-yl-methanol (750 mg) was dissolved in anhydrous THF (38 mL) and the solution cooled to 0° C. Sodium hydride (365 mg, 9.1 mmol) was then added in small portions over 4 minutes, and after complete addition, the reaction was warmed to room temperature for 30 minutes. The reaction was re-cooled to 0° C. and methyltosylate (2.11 g) added in small portions. After complete addition the reaction was warmed to room temperature and stirred for 16 hours. The crude reaction mixture was pre-absorbed onto silica gel and then purified by ISCO combi-flash chromatography (SiO2; gradient elution of MeOH, 2 to 5% in DCM, 1% NH3) to afford the title compound (473 mg) as a pale yellow liquid.

1H NMR (400 MHz, CHLOROFORM-d) δ ppm 3.41 (s, 3 H), 4.40 (s, 2 H), 7.61 (s, 1 H), 7.85 (s, 1 H)

Preparation 79

[2-Amino-6-(4-methoxymethyl-oxazol-2-yl)-3-nitro-pyridin-4-yl]-(6-methyl-pyridin-3-ylmethyl)-carbamic acid ethyl ester The title compound was prepared following the example in preparation 70, using 4-methoxymethyl-oxazole (110 mg), (2-amino-6-bromo-3-nitro-pyridin-4-yl)-(6-methyl-pyridin-3-ylmethyl)-carbamic acid ethyl ester (200 mg) and palladium bis(triphenylphosphine)dichloride (68 mg), giving the product (107 mg) as a yellow gum.

1H NMR (400 MHz, CHLOROFORM-d) δ ppm 1.11-1.29 (m, 3 H) 2.54 (s, 3 H) 3.47 (s, 3 H) 4.09-4.24 (m, 2 H) 4.49 (s, 2 H) 4.96 (s, 2 H) 6.34 (s, 2 H) 7.13 (d, J=7.81 Hz, 1 H) 7.32 (s, 1 H) 7.63-7.72 (m, 1 H) 7.76 (s, 1 H) 8.42 (s, 1 H), LCMS $R_t$=1.62 m/z 443 [MH]$^+$

Preparation 80

(2-Amino-3-nitro-6-thiazol-2-yl-pyridin-4-yl)-(6-methyl-pyridin-3-ylmethyl)-carbamic acid ethyl ester The title compound was prepared following the example in preparation 70, using thiazole (42 mg) and (2-amino-6-bromo-3-nitro-pyridin-4-yl)-(6-methyl-pyridin-3-ylmethyl)-carbamic acid ethyl ester (100 mg), giving the product (79 mg) as a yellow gum.

1H NMR (400 MHz, CHLOROFORM-d) δ ppm 1.06-1.30 (m, 3 H) 2.56 (s, 3 H) 4.07-4.25 (m, 2 H) 4.99 (s, 2 H) 6.26 (s, 2 H) 7.16 (d, J=7.80 Hz, 1 H) 7.46 (s, 1 H) 7.54 (d, J=3.12 Hz, 1 H) 7.64-7.84 (m, 1H) 7.96 (d, J=3.12 Hz, 1 H) 8.35-8.50 (m, 1 H), LCMS $R_t$=2.11 m/z 415 [MH]$^+$

Preparation 81

2-Chloro-3-oxo-pentanoic acid ethyl ester

Sulphuryl chloride (6.50 ml) was added drop-wise to ethyl propionyl acetate (11.70 g) at room temperature and the reaction stirred for 16 hours. The reaction mixture was placed under vacuum for an hour to remove highly volatile material, then the residue was distilled under 'high' vacuum to give an oil that distilled at 75-79° C. with a vacuum of 6 Mbar (=4.5 mmHg), thus providing the title compound (13.54 g) as a clear oil.

1H NMR (400 MHz, CHLOROFORM-d) δ ppm 1.11 (t, 3 H), 1.31 (t, 3 H), 2.75 (q, 2 H), 4.25 (q, 2H), 4.80 (s, 1 H)

Preparation 82

4-Ethyl-oxazole-5-carboxylic acid ethyl ester

2-Chloro-3-oxo-pentanoic acid ethyl ester (13.5 g) was dissolved in 75 ml of 95% formic acid. Ammonium formate (27.6 g) was added and the reaction heated at reflux under nitrogen for 6 hours. After cooling to room temperature the reaction mixture was evaporated and the residue extracted with ether (3×50 ml). Combined ether extracts were washed with water and brine, dried (MgSO$_4$), filtered and evaporated to give a crude oil (9 g). The oil was purified by chromatography on silica gel, eluting with CH$_2$Cl$_2$/MeOH 99:1, providing the title compound (3.77 g) as a pale brown oil.

1H NMR (400 MHz, CHLOROFORM-d) δ ppm 1.25 (t, 3 H), 1.41 (t, 3 H), 2.90 (q, 2 H), 4.41 (q, 2 H), 7.85 (s, 1 H)

Preparation 83

4-Ethyl-oxazole-5-carboxylic acid

4-Ethyl-oxazole-5-carboxylic acid ethyl ester (4.6 g) was stirred in a solution of 1N NaOH (25 ml) and ethanol (1 ml). The reaction mixture was then stirred at room temperature for 16 hours. Diethyl ether (25 ml) was added, and then the aqueous layer separated and acidified with 1N HCl (26 ml). A yellow solid formed that was collected by filtration, washed with water, then with n-pentane, providing the title compound (2.6 g) as a white solid.

1H NMR (400 MHz, CHLOROFORM-d) δ ppm 1.30 (t, 3 H), 2.95 (q, 2 H), 8.0 (s, 1 H)

Preparation 84

4-Ethyl-oxazole

4-Ethyl-oxazole-5-carboxylic acid (1.2 g) was taken up in quinoline (3 ml) and CuO (50 mg) added. The reaction was then heated to 215-20° C. and a colourless distilate was collected, thus providing the title compound (621 mg) as a cloudy oil.

1H NMR (400 MHz, CHLOROFORM-d) δ ppm 1.21 (t, 3 H), 2.55 (q, 2 H), 7.4 (s, 1 H), 7.8 (s, 1 H)

Preparation 85

[2-Amino-6-(4-ethyl-oxazol-2-yl)-3-nitro-pyridin-4-yl]-(6-methyl-pyridin-3-ylmethyl)-carbamic acid ethyl ester The title compound was prepared following the example in preparation 70, using 4-ethyl-oxazole (47 mg) and (2-amino-6-bromo-3-nitro-pyridin-4-yl)-(6-methyl-pyridin-3-ylmethyl)-carbamic acid ethyl ester (100 mg), giving the product (74 mg) as a yellow gum.

1H NMR (400 MHz, CHLOROFORM-d) δ ppm 1.09-1.22 (m, 3 H) 1.25 (t, J=7.42 Hz, 3 H) 2.50 (s, 3 H) 2.56-2.68 (m, 2 H) 4.04-4.21 (m, 2 H) 4.92 (s, 2 H) 6.33 (s, 2 H) 7.10 (d, J=7.81 Hz, 1 H) 7.23 (s, 1 H) 7.46-7.49 (m, 1 H) 7.59-7.69 (m, 1 H) 8.39 (s, 1 H), LCMS $R_t$=2.07 m/z 427 [MH]$^+$

Preparation 86

1-Bromo-3-methyl-butan-2-one

A solution of 3-methyl-2-butanone (5 g) in methanol (55 mL) was cooled to −30° C. Bromine (2.97 uL) was then added dropwise, and once the addition was complete, the reaction was allowed to warm to room temperature and stirred for 3.5 hours. The reaction was then poured into water (100 mL) and extracted with diethyl ether (2×100 mL), the combined extracts were dried (MgSO$_4$), filtered and concentrated. Upon standing the oily residue formed two layers as two different oils which were separated. The bottom layer was retained, thus providing the title compound (5.14 g) as a pale golden oil.

1H NMR (400 MHz, CHLOROFORM-d) δ ppm 1.15 (d, 6 H), 2.95 (m, 1 H), 3.95 (s, 1 H)

Preparation 87

4-Isopropyl-oxazole

1-Bromo-3-methyl-butan-2-one (1.0 g) was added to formamide (3.0 ml) and the reaction mixture heated to 110° C. for 6 hours. After cooling to room temperature the reaction mixture was diluted with a 40% solution of potassium hydroxide (10 ml), stirred for a few minutes and then extracted with diethyl ether (3×10 ml). The ether extracts were combined and carefully evaporated. The resultant brown mobile oil was triturated with n-pentane and the solvent decanted. This process was repeated (×2), and then residual pentane evaporated, to provide the title compound (65 mg) as a light brown oil.

1H NMR (400 MHz, CHLOROFORM-d) δ ppm 1.30 (d, 6 H), 2.85 (m, 1 H), 4.41 (q, 2 H), 7.35 (s, 1 H), 7.80 (s, 1 H)

Preparation 88

[2-Amino-6-(4-isopropyl-oxazol-2-yl)-3-nitro-pyridin-4-yl]-(6-methyl-pyridin-3-ylmethyl)-carbamic acid ethyl ester The title compound was prepared following the example in preparation 70, using 4-isopropyl-oxazole (54 mg) and (2-amino-6-bromo-3-nitro-pyridin-4-yl)-(6-methyl-pyridin-3-ylmethyl)-carbamic acid ethyl ester (100 mg), giving the product (71 mg) as a yellow gum.

1H NMR (400 MHz, CHLOROFORM-d) δ ppm 1.10-1.22 (m, 3 H) 1.27 (d, J=6.64 Hz, 6 H) 2.50 (s, 3 H) 2.82-2.97 (m, 1 H) 3.96-4.27 (m, 2 H) 4.92 (s, 2 H) 6.34 (s, 2 H) 7.10 (d, J=7.81 Hz, 1 H) 7.23 (s, 1 H) 7.45 (s, 1 H) 7.59-7.70 (m, 1 H) 8.39 (s, 1 H), LCMS $R_t$=2.23 m/z 441 [MH]$^+$

Preparation 89

Benzyl-(2,6-dibromo-3-nitro-pyridin-4-yl)-carbamic acid ethyl ester

Potassium carbonate (5.57 g) was added to a stirred solution of (2,6-dibromo-3-nitro-pyridin-4-yl)-carbamic acid ethyl ester (7.44 g) in acetone (100 ml) then benzyl bromide (2.87 ml) was added, followed by sodium iodide (3.63 g). The mixture was left to stir under nitrogen for 36 hours. The reaction mixture was filtered to remove precipitated white solids, concentrated in vacuo, and then partitioned between ethyl acetate (100 ml) and water (100 ml). The organics were dried (MgSO$_4$) and evaporated to a yellow oil. This crude oil was adsorbed onto silica gel and then purified by chromatography on Isco Companion on a silica column (80 g, Redisep) eluting with EtOAc:heptane, increasing the gradient linearly from 10:90 to 50:50. This provided the title compound (7.50 g) as a yellow oil.

1H NMR (400 MHz, CHLOROFORM-d) δ ppm 1.20 (t, 3 H), 4.18 (q, 2 H), 4.8 (br, s, 2 H), 7.0 (s, 1 H), 7.20 (m, 2 H), 7.35 (m, 3 H), LRMS m/z (API) 458, 460, 462 [MH]$^+$

Preparation 90

(2-Amino-6-bromo-3-nitro-pyridin-4-yl)-benzyl-carbamic acid ethyl ester

Benzyl-(2,6-dibromo-3-nitro-pyridin-4-yl)-carbamic acid ethyl ester (7.50 g) was dissolved in 2-methyl-tetrahydrofuran (15 ml) and the solution placed in a sealable vessel. Concentrated aqueous ammonia solution (15 ml) was added and the vial was then sealed and the bi-phasic mixture left to stir vigorously at room temperature for 36 hours. The reaction mixture was then transferred to a separating funnel and ethyl acetate (120 ml) and water (120 ml) were added. The phases were separated, and then the organics washed with brine (100 ml), dried (MgSO$_4$), and evaporated to a yellow oil. Upon standing, a yellow solid crystallised. This was collected by filtration and washed with pentane, providing the title compound (6.64 g) as a yellow solid.

1H NMR (400 MHz, CHLOROFORM-d) δ ppm 1.21 (t, 3 H), 4.19 (q, 2 H), 4.82 (br, s, 2 H), 6.25 (br, s, 2 H), 6.55 (s, 1 H), 7.20-7.35 (m, 5 H), LRMS m/z (API) 395, 397 [MH]$^+$

Preparation 91

[2-Amino-6-(4-methoxymethyl-oxazol-2-yl)-3-nitro-pyridin-4-yl]-benzyl-carbamic acid ethyl ester The title compound was prepared following the example in preparation 70, using 4-methoxymethyl-oxazole (114 mg), (2-amino-6-bromo-3-nitro-pyridin-4-yl)-benzyl-carbamic acid ethyl ester (200 mg) and palladium bis(triphenylphosphine)dichloride (71 mg), giving the product (160 mg) as a yellow gum.

1H NMR (400 MHz, CHLOROFORM-d) δ ppm 1.20 (t, J=7.03 Hz, 3 H) 3.46 (s, 3 H) 4.12-4.22 (m, 2 H) 4.47 (s, 2 H) 4.92-5.03 (m, 2 H) 6.32 (s, 2 H) 7.28-7.35 (m, 6 H) 7.74 (s, 1 H), LCMS $R_t$=3.08 m/z 428 [MH]$^+$

Preparation 92

Dimethyl-oxazol-4-ylmethyl-amine

Thionyl chloride (5.51 ml) was added dropwise to a cooled solution (0° C.) of oxazol-4-yl-methanol (1.51 g) in dichloromethane (50 ml) over 5 minutes. The resulting cloudy solution was stirred for 5 minutes at room temperature and then heated to reflux. On heating the solution became clear and a deep yellow colour. After 10 minutes at reflux the solution was allowed to cool to room temperature and the excess thionyl chloride and solvent were then removed under reduced pressure to afford the corresponding chloride compound that was used without further purification.

Dimethylamine (38 ml of a 2.0 M solution in THF) was cooled to 0° C. in an ice-bath and a solution of the chloride (1.74 g) in dry THF (50 ml) was added in small portions over 10 mins. The resulting suspension was then left to react for 16 hours. The solvent was removed to afford a dark brown/black solid that was then pre-absorbed onto silica and purified by ISCO combi-flash chromatography on silica gel eluting with 5 to 15% MeOH in dichloromethane with 10% NH3. This provided the title compound (335 mg) as a dark brown viscous oil.

1H NMR (400 MHz, CHLOROFORM-d) δ ppm 2.35 (s, 6 H), 3.50 (s, 2 H), 7.62 (s, 1 H), 7.85 (s, 1 H)

Preparation 93

[2-Amino-6-(4-dimethylaminomethyl-oxazol-2-yl)-3-nitro-pyridin-4-yl]-benzyl-carbamic acid ethyl ester The title compound was prepared following the example in preparation 70, using dimethyl-oxazol-4-ylmethyl-amine (128 mg), (2-amino-6-bromo-3-nitro-pyridin-4-yl)-benzyl-carbamic acid ethyl ester (200 mg) and palladium bis(triphenylphosphine)dichloride (71 mg), giving the product (99 mg) as a yellow gum.

1H NMR (400 MHz, CHLOROFORM-d) δ ppm 1.20 (t, J=7.03 Hz, 3 H) 2.32 (s, 6 H) 3.49 (s, 2 H) 4.13-4.23 (m, 2 H) 4.92-5.03 (m, 2 H) 6.33 (s, 2 H) 7.28-7.36 (m, 6 H) 7.68 (s, 1 H), LCMS $R_t$=1.86 m/z 441 [MH]$^+$

Preparation 94

{2-Amino-3-nitro-6-[1-(2-trimethylsilanyl-ethoxymethyl)-1H-imidazol-2-yl]-pyridin-4-yl}-benzyl-carbamic acid ethyl ester The title compound was prepared following the example in preparation 70, using 1-(2-trimethylsilanyl-ethoxymethyl)-1H-imidazole (201 mg), (2-amino-6-bromo-3-nitro-pyridin-4-yl)-benzyl-carbamic acid ethyl ester (200 mg) and palladium bis(triphenylphosphine)dichloride (71 mg), giving the product (174 mg) as a yellow gum.

1H NMR (400 MHz, CHLOROFORM-d) δ ppm −0.04 (s, 9 H) 0.87-0.94 (m, 2 H) 1.19 (t, J=7.03 Hz, 3 H) 3.49-3.59 (m, 2 H) 4.10-4.22 (m, 2 H) 4.98 (s, 2 H) 5.93 (s, 2 H) 6.18 (s, 2 H) 7.18 (s, 1H) 7.23 (s, 1 H) 7.28-7.38 (m, 5 H) 7.53 (s, 1 H)

Preparation 95

(2-Amino-6-methylsulfanyl-3-nitro-pyridin-4-yl)-benzyl-carbamic acid ethyl ester Sodium methanethiolate (180 mg) was added portion-wise to a stirred suspension of (2-amino-6-chloro-3-nitro-pyridin-4-yl)-benzyl-carbamic acid ethyl ester (300 mg) in methanol:THF (3:1, 4 ml). The mixture was sealed in a ReactiVial then left to stir at room temperature for 2 hours. The reaction mixture was diluted with methanol then pre-absorbed directly onto silica gel. The crude was columned on Isco Companion on a silica column (12 g, Redisep), eluting with EtOAc:heptane, increasing the gradient linearly from 30:70 to 50:50 over 6 column volumes. The desired fractions were combined and evaporated to provide the title compound (297 mg) as a yellow gum.

1H NMR (400 MHz, METHANOL-d$_4$) δ ppm 1.04-1.22 (m, 3 H) 2.43 (s, 3 H) 3.96-4.24 (m, 2 H) 4.35-4.55 (m, 1 H) 5.03-5.17 (m, 1 H) 6.13 (s, 2 H) 7.12-7.47 (m, 6 H), LCMS $R_t$=3.29 m/z 363 [MH]$^+$

Preparation 96

[2-Amino-6-(2-fluoro-phenyl)-3-nitro-pyridin-4-yl]-benzyl-carbamic acid ethyl ester 2-Fluoro-phenylboronic acid (34 mg), copper (I) thiophene-2-carboxylate (79 mg) and palladium bis(triphenylphosphine)dichloride (19 mg) were added to a microwave vial. The vial was then flushed with nitrogen and sealed. A solution of (2-amino-6-methylsulfanyl-3-nitro-pyridin-4-yl)-benzyl-carbamic acid ethyl ester (42 mg) in anhydrous THF (0.5 ml) was then added to the vial and the mixture heated under microwave irradiation (CEM) for 10 minutes at 100° C. The reaction mixture was then diluted with methanol and filtered through Arbocel directly onto a cation-exchange cartridge (Bakerbond, sulphonic acid bonded-phase, 1 g). The cartridge was washed with methanol (2×5 ml) to remove impurities and then the product was released by eluting with ammonia in methanol (2 M, 5 ml). The desired fractions were combined and evaporated to yield the title compound (31 mg) as a yellow gum.

1H NMR (400 MHz, CHLOROFORM-d) δ ppm 1.03-1.31 (m, 3 H) 4.16 (s, 2 H) 4.91 (br. s., 1 H) 6.20 (s, 2 H) 6.95 (s, 1 H) 7.07 (dd, J=11.71, 8.20 Hz, 1 H) 7.16-7.22 (m, 1 H) 7.21-7.42 (m, 7 H) 7.84-7.93 (m, 1 H), LCMS $R_t$=3.50 m/z 411 [MH]$^+$

Preparation 97

[2-Amino-6-(3-fluoro-phenyl)-3-nitro-pyridin-4-yl]-benzyl-carbamic acid ethyl ester The title compound was prepared following the example in preparation 96 using 3-fluoro-phenylboronic acid, providing the product (18 mg) as a yellow gum.

1H NMR (400 MHz, CHLOROFORM-d) δ ppm 1.08-1.35 (m, 3 H) 4.19 (s, 2 H) 5.29 (br. s., 2 H) 6.29 (s, 2 H) 6.66 (s, 1

H) 7.04-7.17 (m, 1 H) 7.28-7.40 (m, 7 H) 7.43-7.55 (m, 1 H), LCMS $R_t$=3.53 m/z 411 $[MH]^+$

Preparation 98

[2-Amino-6-(4-fluoro-phenyl)-3-nitro-pyridin-4-yl]-benzyl-carbamic acid ethyl ester The title compound was prepared following the example in preparation 96 using 4-fluoro-phenylboronic acid, providing the product (28 mg) as a yellow gum.

1H NMR (400 MHz, CHLOROFORM-d) δ ppm 1.19 (s, 3 H) 4.19 (s, 2 H) 5.33 (br. s., 2 H) 6.31 (s, 2 H) 6.63 (s, 1 H) 7.03-7.13 (m, 2 H) 7.29-7.38 (m, 5 H) 7.68-7.77 (m, 2 H), LCMS $R_t$=3.52 m/z 411 $[MH]^+$ Preparation 99

(2-Amino-6-methoxy-3-nitro-pyridin-4-yl)-benzyl-carbamic acid ethyl ester

Sodium hydride (9 mg) was dissolved carefully in methanol (0.5 ml) and this solution then added to a solution of (2-amino-6-bromo-3-nitro-pyridin-4-yl)-benzyl-carbamic acid ethyl ester (50 mg) in THF (0.5 ml) at room temperature. The reaction was stirred under nitrogen for 2 hours then the solution pre-absorbed directly onto silica gel. The mixture was purified by chromatography on an Isco Companion, eluting with ethyl acetate:heptane, increasing the gradient linearly from 20:80 to 60:40 over several column volumes. The desired fractions were combined and evaporated to provide the title compound (23 mg) as a yellow gum.

1H NMR (400 MHz, CHLOROFORM-d) δ ppm 1.15 (s, 3 H) 3.84 (s, 3 H) 3.97-4.32 (m, 2 H) 4.42 (d, J=15.05 Hz, 1 H) 5.21 (d, J=15.05 Hz, 1 H) 5.77 (s, 1 H) 6.61 (br. s., 2 H) 7.23-7.38 (m, 5 H), LCMS $R_t$=3.19 m/z 347 $[MH]^+$ Preparation 100

(2-Amino-6-ethoxy-3-nitro-pyridin-4-yl)-benzyl-carbamic acid ethyl ester

The title compound was prepared following the example in preparation 99 using ethanol and giving the product (31 mg) as an off-white solid.

1H NMR (400 MHz, CHLOROFORM-d) δ ppm 1.10-1.28 (m, 3 H) 1.31 (t, J=7.03 Hz, 3 H) 3.97-4.32 (m, 4 H) 4.43 (d, J=15.83 Hz, 1 H) 5.20 (d, J=15.83 Hz, 1 H) 5.70-5.86 (m, 1 H) 6.61 (br. s., 2 H) 7.26-7.36 (m, 5 H), LCMS $R_t$=3.36 m/z 361 $[MH]^+$ Preparation 101

(2-Amino-6-propoxy-3-nitro-pyridin-4-yl)-benzyl-carbamic acid ethyl ester

The title compound was prepared following the example in preparation 99 using propanol and giving the product (30 mg) as an off-white solid.

1H NMR (400 MHz, CHLOROFORM-d) δ ppm 0.95 (t, J=7.42 Hz, 3 H) 1.07-1.33 (m, 3 H) 1.62-1.79 (m, 2 H) 3.95-4.29 (m, 4 H) 4.44 (d, J=15.63 Hz, 1 H) 5.20 (d, J=15.63 Hz, 1 H) 5.67-5.90 (m, 1 H) 6.61 (br. s., 2 H) 7.25-7.41 (m, 5 H), LCMS $R_t$=3.51 m/z 375 $[MH]^+$ Preparation 102

(2-Amino-6-methylamino-3-nitro-pyridin-4-yl)-benzyl-carbamic acid ethyl ester

Methylamine (40% solution in water) (0.055 ml) was added to a solution of (2-amino-6-bromo-3-nitro-pyridin-4-yl)-benzyl-carbamic acid ethyl ester (50 mg) in THF (0.5 ml) at room temperature. The reaction was stirred under nitrogen for 16 hours then the solution pre-absorbed directly onto silica gel. The mixture was purified by chromatography on an Isco Companion, eluting with ethyl acetate:heptane, increasing the gradient linearly from 20:80 to 60:40 over several column volumes. The desired fractions were combined and evaporated to provide the title compound (30 mg) as a yellow gum.

1H NMR (400 MHz, CHLOROFORM-d) δ ppm 1.04-1.40 (m, 3 H) 2.82 (s, 3 H) 3.97-4.33 (m, 3 H) 4.75-5.04 (m, 1 H) 5.22-5.49 (m, 2 H) 6.79 (br. s., 2 H) 7.28-7.39 (m, 5 H), LCMS $R_t$=2.83 m/z 346 $[MH]^+$ Preparation 103

(2-Amino-6-ethylamino-3-nitro-pyridin-4-yl)-benzyl-carbamic acid ethyl ester

The title compound was prepared following the example in preparation 102 using ethylamine (70% solution in water) (0.051 ml) and giving the product (35 mg) as a yellow gum.

1H NMR (400 MHz, CHLOROFORM-d) δ ppm 1.05-1.37 (m, 6 H) 3.23 (s, 2 H) 3.93-4.35 (m, 3 H) 4.84 (s, 1 H) 5.17-5.52 (m, 2 H) 6.75 (br. s., 2 H) 7.29-7.42 (m, 5 H), LCMS $R_t$=3.0 m/z 360 $[MH]^+$ Preparation 104

(2-Amino-6-propylamino-3-nitro-pyridin-4-yl)-benzyl-carbamic acid ethyl ester

The title compound was prepared following the example in preparation 102 using n-propylamine (0.052 ml) and giving the product (35 mg) as a yellow gum.

1H NMR (400 MHz, CHLOROFORM-d) δ ppm 0.91 (t, J=7.42 Hz, 3 H) 1.06-1.38 (m, 3 H) 1.44-1.55 (m, 2 H) 3.14 (s, 2 H) 3.93-4.30 (m, 3 H) 4.75-5.07 (m, 1 H) 5.22-5.48 (m, 2 H) 6.77 (br. s., 2 H) 7.28-7.37 (m, 5 H), LCMS $R_t$=3.16 m/z 374 $[MH]^+$ Preparation 105

(2-Amino-6-butylamino-3-nitro-pyridin-4-yl)-benzyl-carbamic acid ethyl ester

The title compound was prepared following the example in preparation 102 using n-butylamine (0.063 ml) and giving the product (39 mg) as a yellow gum.

1H NMR (400 MHz, CHLOROFORM-d) δ ppm 0.92 (t, J=7.42 Hz, 3 H) 1.12-1.37 (m, 5 H) 1.41-1.51 (m, 2 H) 3.17 (s, 2 H) 3.98-4.31 (m, 3 H) 4.84 (s, 1 H) 5.26-5.47 (m, 2 H) 6.75 (br s., 2 H) 7.28-7.36 (m, 5 H), LCMS R$_t$=3.31 m/z 388 [MH]$^+$

Preparation 106

[2-Amino-6-(2-methoxy-ethylamino)-3-nitro-pyridin-4-yl]-benzyl-carbamic acid ethyl ester The title compound was prepared following the example in preparation 102 using 2-methoxyethylamine (1.0 ml) and (2-amino-6-bromo-3-nitro-pyridin-4-yl)-benzyl-carbamic acid ethyl ester (150 mg), giving the product (121 mg) as a yellow gum.

1H NMR (400 MHz, DMSO-d$_6$) δ ppm 1.21 (t, 3 H), 3.35 (s, 3 H), 3.45 (m, 4 H), 4.20 (q, 2 H), 5.25 (br, s, 2 H), 7.20-7.35 (m, 5 H), LRMS m/z (API) 390 [MH]$^+$, 388 [MH]$^-$

Preparation 107

(2,6-Dibromo-3-nitro-pyridin-4-yl)-(6-trifluoromethyl-3-ylmethyl)-carbamic acid ethyl ester The title compound was prepared following the example in preparation 68 using potassium carbonate (1.50 g), (2,6-dibromo-3-nitro-pyridin-4-yl)-carbamic acid ethyl ester (2.0 g) in acetone (40 ml), 5-(chloromethyl)-2-trifluoromethylpyridine (1.06 g) and sodium iodide (0.98 g). This gave the product (2.79 g) as a yellow oil.

1H NMR (400 MHz, DMSO-d$_6$) δ ppm 1.20 (t, 3 H), 4.20 (q, 2 H), 4.85 (s, 2 H), 7.28 (s, 1 H), 7.71 (d, 1 H), 7.88 (dd, 1 H), 8.61 (d, 1 H)

Preparation 108

(2-Amino-6-bromo-3-nitro-pyridin-4-yl)-(6-trifluoromethyl-pyridin-3-ylmethyl)-carbamic acid ethyl ester The title compound was prepared following the example in preparation 69 using (2,6-dibromo-3-nitro-pyridin-4-yl)-(6-trifluoromethyl-pyridin-3-ylmethyl)-carbamic acid ethyl ester (2.75 g), aqueous ammonia (11 ml), and 2-methyl-THF (11 ml). This gave the product (1.92 g) as a yellow oil.

1H NMR (400 MHz, DMSO-d$_6$) δ ppm 1.21 (t, 3 H), 4.11 (q, 2 H), 4.95 (br, s, 2 H), 6.41 (br, s, 2 H), 6.60 (s, 1 H), 7.65 (d, 1 H), 7.95 (m, 1 H), 8.65 (m, 1 H)

Preparation 109

(3-Cyano-benzyl )-(2,6-dibromo-3-nitro-pyridin-4-yl)-carbamic acid ethyl ester

The title compound was prepared following the example in preparation 68 using potassium carbonate (1.50 g), (2,6-dibromo-3-nitro-pyridin-4-yl)-carbamic acid ethyl ester (2.0 g) in acetone (40 ml), 3-chloromethyl-benzonitrile (0.82 g) and sodium iodide (0.98 g). This gave the product (2.62 g) as a yellow oil.

1H NMR (400 MHz, DMSO-d$_6$) δ ppm 1.20 (t, 3 H), 4.15 (q, 2 H), 4.80 (br, s,2 H), 7.15 9s, 1 H), 7.5 (m, 2 H), 7.61 (m, 1 H), 7.65 (m, 1 H)

Preparation 110

(2-Amino-6-bromo-3-nitro-pyridin-4-yl)-(3-cyano-benzyl)-carbamic acid ethyl ester The title compound was prepared following the example in preparation 68 using (3-cyano-benzyl)-(2,6-dibromo-3-nitro-pyridin-4-yl)-carbamic acid ethyl ester (2.32 g), aqueous ammonia (10.2 ml), and 2-methyl-THF (10.2 ml). This gave the product (1.51 g) as a yellow solid.

1H NMR (400 MHz, DMSO-d$_6$) δ ppm 1.20 (t, 3 H), 4.21 (q, 2 H), 4.95 (br, s, 2 H), 6.35 (br, s, 2 H), 6.59 (s, 1 H), 7.5 (m, 1 H), 7.6 (m, 3 H)

Preparation 111

(2-Amino-3-nitro-6-oxazol-2-yl-pyridin-4-yl)-(6-trifluoromethyl-pyridin-3-ylmethyl)-carbamic acid ethyl ester The title compound was prepared following the example in preparation 70, using oxazole (30 mg), (2-amino-6-bromo-3-nitro-pyridin-4-yl)-(6-trifluoromethyl-pyridin-3-ylmethyl)-carbamic acid ethyl ester (100 mg) and palladium bis(triphenylphosphine)dichloride (30 mg), giving the product (61 mg) as a yellow solid 1H NMR (400 MHz, CHLOROFORM-d) δ ppm 1.10-1.31 (m, 3 H) 4.02-4.30 (m, 2 H) 5.07 (s, 2 H) 6.39 (s, 2 H) 7.32 (s, 1 H) 7.35 (s, 1 H) 7.69 (d, J=7.82 Hz, 1 H) 7.84 (s, 1 H) 8.01 (d, J=5.47 Hz, 1 H) 8.70 (s, 1 H), LCMS R$_t$=3.02 m/z 453 [MH]$^+$

Preparation 112

[2-Amino-6-(4-methyl-oxazol-2-yl)-3-nitro-pyridin-4-yl]-(6-trifluoromethyl-pyridin-3-ylmethyl)-carbamic acid ethyl ester The title compound was prepared following the example in preparation 70, using 4-methyl-oxazole (36 mg), (2-amino-6-bromo-3-nitro-pyridin-4-yl)-(6-trifluoromethyl-pyridin-3-ylmethyl)-carbamic acid ethyl ester (100 mg) and palladium bis(triphenylphosphine)dichloride (30 mg), giving the product (44 mg) as a yellow solid.

1H NMR (400 MHz, CHLOROFORM-d) δ ppm 1.10-1.25 (m, 3 H) 2.28 (s, 3 H) 4.09-4.25 (m, 2 H) 5.06 (s, 2 H) 6.41 (s, 2 H) 7.25 (s, 1 H) 7.55 (d, J=1.17 Hz, 1 H) 7.69 (d, J=8.21 Hz, 1 H) 8.01 (d, J=7.03 Hz, 1 H) 8.70 (s, 1 H), LCMS R$_t$=3.13 m/z 467 [MH]$^+$

Preparation 113

(2-Amino-3-nitro-6-oxazol-2-yl-pyridin-4-yl)-(3-cyano-benzyl)-carbamic acid ethyl ester The title compound was prepared following the example in preparation 70, using oxazole (33 mg), (2-amino-6-bromo-3-nitro-pyridin-4-yl)-(3-cyano-benzyl)-carbamic acid ethyl ester (100 mg) and palladium bis(triphenylphosphine)dichloride (33 mg), giving the product (67 mg) as a yellow solid.

1H NMR (400 MHz, CHLOROFORM-d) δ ppm 1.20 (t, J=7.03 Hz, 3 H) 4.17 (s, 2 H) 4.99 (s, 2 H) 6.36 (s, 2 H) 7.26 (s, 1 H) 7.34 (s, 1 H) 7.46 (t, J=7.62 Hz, 1 H) 7.59 (d, J=7.42 Hz, 1 H) 7.62-7.68 (m, 2 H) 7.82 (s, 1 H), LCMS R$_t$=2.93 m/z 409 [MH]$^+$

Preparation 114

[2-Amino-6-(4-methyl-oxazol-2-yl )-3-nitro-pyridin-4-yl]-(3-cyano-benzyl)-carbamic acid ethyl ester The title compound was prepared following the example in preparation 70, using 4-methyl-oxazole (40 mg), (2-amino-6-bromo-3-nitro-pyridin-4-yl)-(3-cyano-benzyl)-carbamic acid ethyl ester (100 mg) and palladium bis(triphenylphosphine)dichloride (30 mg), giving the product (65 mg) as a yellow solid.

1H NMR (400 MHz, CHLOROFORM-d) □ ppm 1.10-1.25 (m, 3 H) 2.28 (s, 3 H) 4.10-4.23 (m, 2 H) 4.99 (s, 2 H) 6.39 (s, 2 H) 7.20 (s, 1 H) 7.46 (t, J=7.62 Hz, 1 H) 7.54 (d, J=1.17 Hz, 1 H) 7.60 (d, J=7.42 Hz, 1 H) 7.63-7.69 (m, 2 H), LCMS R$_t$=3.04 m/z 423 [MH]$^+$ Preparation 115

4-Amino-1-benzyl-6-bromo-1,3-dihydro-imidazo[4,5-c]pyridin-2-one (2-Amino-6-bromo-3-nitro-pyridin-4-yl)-benzyl-carbamic acid ethyl ester (50 mg, 0.13 mmol) was dissolved in AcOH (3 ml). Fe powder (43 mg, 0.76 mmol) was added and the mixture was vigorously stirred at room temperature for 24 h. The reaction mixture diluted with EtOAc (20 ml) and water (10 ml). The mixture was filtered through celite, washing through with EtOAc (20 ml). The layers were separated and the organic layer was washed with water (10 ml), sat. NaHCO$_3$ $_{(aq)}$ (2×10 ml) and brine (10 ml), dried over MgSO$_4$ and concentrated in vacuo. The crude was triturated in pentane, filtered and dried in vacuo at 40° C. to give the title compound (15 mg) as a beige solid.
$^1$H NMR (d6-DMSO) δ 10.47 (br s, 1H), 7.36-7.26 (m, 5H), 6.70 (s, 1H), 6.05 (br s, 2H), 4.94 (s, 2H); LRMS (APCI and ES) m/z 319/321 [MH]$^+$.

Preparation 116

Benzyl-(2,3-diamino-6-pyrazol-1-yl-pyridin-4-yl)-carbamic acid ethyl ester (2-Amino-3-nitro-6-pyrazol-1-yl-pyridin-4-yl)-benzyl-carbamic acid ethyl ester (65.4 mg, 0.171 mmol) was dissolved in methanol (5 mL) and hydrogenated over Raney Nickel (25 mg) at room temperature, 80 psi for 1 hour. The reaction mixture was filtered through a short plug of Arbocel and the filtrate was then evaporated in vacuo to afford 58mg of the title compound as a brown residue.
$^1$H NMR (CDCl$_3$) □ 1.15 (m, 3H), 2.90 (s br, 2H), 3.50 (m, 2H), 4.12 (d, 2H), 4.20 (s br, 2H), 6.28 (s br, 1H), 7.10 (s br, 1H), 7.20-7.35 (m, 5H), 7.85 (s, 1H), 8.30 (s, 1H). LRMS (ES$^+$) m/z 353 (MH$^+$).

Preparation 117

(2-Amino-3-nitro-6-[1,2,4]triazol-1-yl-pyridin-4-yl)-benzyl-carbamic acid ethyl ester The title compound was prepared following the example in preparation 116.
$^1$H NMR (CDCl$_3$) □ 1.20 (t, 3H), 4.19 (quart, 2H), 5.00 (s br, 2H), 6.37 (s br, 2H), 7.09 (s, 1H), 7.27-7.37 (m, 5H), 8.03 (s, 1H), 9.00 (s, 1H). LRMS (ES$^+$) m/z 384 (MH$^+$).

Preparation 118

(ai) (2-Amino-3-nitro-6-[1,2,3]triazol-2-yl-pyridin-4-yl)-benzyl-carbamic acid ethyl ester and (bi) (2-Amino-3-nitro-6-[1,2,3]triazol-1-yl-pyridin-4-yl)-benzyl-carbamic acid ethyl ester (ai)

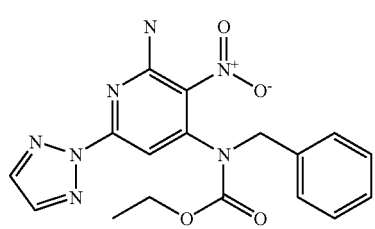

(bi)

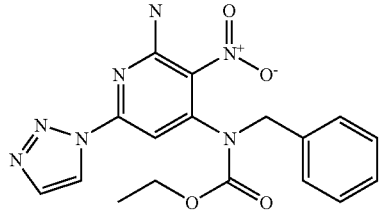

(2-Amino-6-chloro-3-nitro-pyridin-4-yl)-benzyl-carbamic acid ethyl ester (100 mg, 0.285 mmol) was dissolved in acetonitrile (10 mL) and 1,2,3-triazole (39.4 mg, 0.570 mmol), followed by potassium carbonate (78.8 mg, 0.570 mmol) were added. The yellow solution was stirred at 70° C. for 18 hours under an atmosphere of nitrogen. The resulting dark orange reaction mixture was evaporated in vacuo and the residue was dissolved in EtOAc and extracted with water. The organic extracts were combined, dried over anhydrous magnesium sulphate and concentrated in vacuo. The 2 structural isomers were isolated by autopurification (chiralpak column, 50:50 methanol:ethanol) to afford 48.1 mg of (ai) (2-Amino-3-nitro-6-[1,2,3]triazol-2-yl-pyridin-4-yl)-benzyl-carbamic acid ethyl ester and 34.9 mg of (bi) (2-Amino-3-nitro-[1,2,3]triazol-1-yl-pyridin-4-yl)-benzyl-carbamic acid ethyl ester; both as yellow solids.
$^1$H NMR (CDCl$_3$) (ai) □ 1.19 (t, 3H), 4.18 (d, 2H), 5.00 (s br, 2H), 6.62 (s br, 2H), 7.25-7.36 (m, 6H), 7.87 (s, 1 H). LRMS (ES$^+$) m/z 384 (MH$^+$). $^1$H NMR (CDCl$_3$) (bi) □ 1.21 (t, 3H), 4.20 (q, 2H), 5.02 (s br, 2H), 6.35 (s br, 2H), 7.24-7.40 (m, 6H), 7.77 (s, 1H), 8.40 (d, 1H). LRMS (ES$^+$) m/z 384 (MH$^+$).

Preparation 119

[2-Amino-6-(4-fluoro-pyrazol-1-yl)-3-nitro-pyridin-4-yl]-benzyl-carbamic acid ethyl ester (2-Amino-6-chloro-3-nitro-pyridin-4-yl)-benzyl-carbamic acid ethyl ester (100mg, 0.285 mmol), 4-fluoropyrazole (24.5 mg, 0.285 mmol) and potassium carbonate (118 mg 0.855 mmol) were stirred together in 5 mL of acetonitrile, under nitrogen. Heated the reaction to reflux for 3 hours and then allowed to cool to ambient temperature over night.
The solvent was evaporated and the dichloromethane soluble portion of the residue was purified by chromatography on silica, eluted with 1% methanol in dichloromethane. Combined and evaporated fractions containing clean material with an Rf of 0.66 in same eluent to give the title compound (106mg) as a yellow gum.
$^1$H NMR (CDCl$_3$, 400 MHz) □ 1.20 (broad singlet, 3H), 4.17 (broad singlet, 2H), 4.95 (broad doublet, 2H) 6.38 (broad singlet, 2H) 7.15 (s, 1H) 7.35 (m, 5H) 7.58 (d, 1H) 8.23 (d,1H). LRMS (ES+) m/z 401 (MH+)
The following compounds were prepared using an identical method to that described in Preparation 119.

Preparation 120

[2-Amino-6-(3,5-dimethyl-pyrazol-1-yl)-3-nitro-pyridin-4-yl]-benzyl-carbamic acid ethyl ester $^1$H NMR (CDCl$_3$, 400 MHz) □ 1.19 (broad singlet, 3H), 2.24 (s, 3H) 2.62 (s, 3H) 4.16 (broad singlet, 2H), 4.94 (broad doublet, 2H) 5.98 (s, 1H) 6.36 (broad singlet, 2H) 7.21 (s,1H) 7.32 (m, 5H). LRMS (ES+) m/z 411 (MH+).

Preparation 121

[2-Amino-6-(4-methyl-pyrazol-1-yl)-3-nitro-pyridin-4-yl]-benzyl-carbamic acid ethyl ester $^1$H NMR (CDCl$_3$, 400 MHz) ☐ 1.20 (broad singlet, 3H), 2.14 (s, 3H) 4.16 (broad singlet, 2H), 4.95 (broad doublet, 2H) 6.39 (broad singlet, 2H) 7.16 (s,1H) 7.36 (m, 5H). 7.53 (s, 1H) 8.15 (s,1H). LRMS (ES+) m/z 397(MH+)

Preparation 122

[2-Amino-6-(3-trifluoromethyl-pyrazol-1-yl)-3-nitro-pyridin-4-yl]-benzyl-carbamic acid ethyl ester $^1$H NMR (CDCl$_3$, 400 MHz) ☐ 1.22 (broad singlet, 3H), 4.20 (broad singlet, 2H), 5.00 (broad doublet, 2H), 6.33 (broad singlet, 2H) 6.69 (d, 1H), 7.22 (s,1 H), 7.35 (m, 5H), 8.45 (d,1 H). LRMS (ES+) m/z 451 (MH+)

Preparation 123

[2-Amino-6-(5-methyl-3-trifluoromethyl-pyrazol-1-yl)-3-nitro-pyridin-4-yl]-benzyl-carbamic acid ethyl ester $^1$H NMR (CDCl$_3$, 400 MHz) ☐ 1.22 (broad singlet, 3H), 2.69 (s, 3H), 4.20 (broad singlet, 2H), 5.00 (broad, 2H), 6.29 (broad singlet, 2H), 6.41 (s, 1H), 7.19 (s,1 H), 7.33 (m, 5H). LRMS (ES+) m/z 465 (MH+).

Preparation 124

{2-Amino-6-[4-(2-hydroxy-ethyl)-pyrazol-1-yl]-3-nitro-pyridin-4-yl}-benzyl-carbamic acid ethyl ester $^1$H NMR (CDCl$_3$, 400 MHz) ☐ 1.20 (broad singlet, 3H), 2.78 (t, 2H), 3.85 (q, 2H) 4.18 (braod singlet, 2H), 4.98 (broad, 2H), 6.37 (broad singlet, 2H), 7.17 (s,1H), 7.33 (m, 5H), 7.61 (s, 1H), 8.28 (s, 1H). LRMS (ES+) m/w 427 (MH+)

Preparation 125

1-Benzyl-4-benzylamino-2-oxo-2,3-dihydro-1H-imidazo[4,5-c]pyridine-6-carboxylic acid-(1-hydroxyimino-ethyl)-amide CDI (52 mg, 0.32 mmol) was added to a solution of 1-benzyl-4-benzylamino-2-oxo-2,3-dihydro-1H-imidazo[4,5-c] pyridine-6-carboxylic acid (80 mg, 0.21 mmol) and Hunnigs base (83 µl, 0.64 mmol) in dry DMF in a ReactiVial. The vial was sealed and the mixture was stirred at room temperature for 15 minutes. N-Hydroxyacetamidine (24 mg, 0.32 mmol) was added and mixture heated to 60° C. in an aluminium block. The mixture was left to stir at this temperature for 3 hrs then allowed to cool and concentrated in vacuo. The residue was partitioned between EtOAc (15 ml) and water (5 ml). The layers were separated and the organic phase was washed with brine (5 ml). At this point, some solid precipitated and was left inside the separating funnel. This was washed into the organic phase with MeOH then the organics were dried (MgSO$_4$) and evaporated to yield the final product as a white solid (120 mg, 130%). Material probably contains inorganic material, but taken on with a view to purification after next step.

$^1$H NMRCD3OD ☐ 1.94 (s, 3H) 4.54 (s, 2H) 5.16 (s, 2H) 7.16-7.46 (m, 11H). LCMS R$_t$=3.47 m/z 431 [MH]$^+$

Preparation 126

N2,N2-Dibenzyl-6-bromo-3-nitro-pyridine-2,4-diamine 2,6-Dibromo-4-amino-5-nitro-pyridine (3.52 g) was dissolved in 2-methyl THF (40 ml) and the solution was cooled to <5° C. in an ice bath. A solution of dibenzylamine (2.39 ml) and triethylamine (2.48 ml) in 2-methyl THF (20 ml) was added drop-wise to the dibromopyridine solution and the reaction mixture allowed to warm to RT and left to stir under nitrogen for 16 h. Additional dibenzylamine (684 µl) and triethylamine (496 µl) was added and the mixture was left to stir at RT for a further 5 hours, then further dibenzylamine (684 µl) and triethylamine (496 µl) was added and the mixture was left to stir at RT for an additional 16 h.

The mixture was transferred to a separating funnel then water (60 ml) added. Layers were separated and the aqueous then re-extracted with EtOAc (60 ml). The combined organics were dried (MgSO$_4$) and evaporated to an orange gum. The gum was crystallised from MeOH:water (90:10, ~200 ml) to give a solid that was filtered and washed with MeOH: water (90:10) then dried under vacuum to yield the title compound as an orange crystalline solid (3.6 g).

$^1$H NMR (CDCl$_3$, 400 MHz) ☐ 4.45 (s, 4H), 5.95 (br, s, 2H), 6.22 (s, 1H), 7.05-7.15 (m, 4H), 7.21-7.35 (m, 6H). LCMS R$_t$=3.73 m/z 415 [MH]$^+$

Preparation 127

N2,N2-Dibenzyl-6-bromo-N4-(6-methyl-pyridin-3-ylmethyl)-3-nitropyridine-2,4-diamine Potassium tert-butoxide (448 mg) was added portion-wise to a cooled solution (−18° C.—salt/ice bath) of N2,N2-dibenzyl-6-bromo-3-nitro-pyridine-2,4-diamine (1500 mg, 3.63 mmol) in THF (40 ml) under nitrogen. The solution changed from yellow to deep red/orange on addition of base. The solution was left to stir in the cooling bath for 5 minutes.

5-Bromomethyl-2-methyl-pyridine hydrobromide (1160 mg) was partitioned between saturated NaHCO$_3$ solution (20 ml) and 2-Me THF (20 ml). The phases were separated and the aqueous was re-extracted with 2-Me THF (20 ml). The combined organics were dried (MgSO$_4$) then added drop-wise to the aminopyridine and KOtBu mixture drop-wise via a dropping funnel. The colour changed from red/orange to yellow/orange. The mixture was left to warm slowly to RT in the cooling bath then left to stir at RT under nitrogen for 48 h. The reaction mixture was cooled back down to −18° C. (ice/salt bath) then KOtBu (102 mg) was added followed by tetra-n-butylammonium iodide (670 mg). The cooling bath was removed and the mixture allowed to warm to RT then stirred for a further 4 h. The reaction mixture was pre-absorbed directly onto silica then columned on Isco Companion on a silica column (80 g, Redisep), eluting with EtOAc:heptane, increasing the gradient linearly from 40:60 to 80:20 over 10 column volumes. The desired fractions were combined and evaporated to give the title compound as a yellow solid (0.99 g).

$^1$H NMR (CDCl$_3$, 400 MHz) ☐ 2.58 (s, 3H), 4.38 (d, 2H), 4.45 (s, 4H), 6.19 (s, 1H) 7.05-7.15 (m, 4H), 7.18 (d, 1H), 7.21-7.35 (m, 6H), 7.49 (dd, 1H), 7.99 (t, 1H), 8.42 (d, 1H). LCMS R$_t$3.12 m/z 520 [MH]$^+$

Preparation 128

N2,N2-Dibenzyl-N4-(6-methyl-pyridin-3-ylmethyl)-3-nitro-6-oxazol-2-yl-pyridine-2,4-diamine Butyl lithium (2.9 ml) was added drop-wise to a stirred solution of oxazole (0.251 ml) in THF (5 ml) at −78° C. (dry ice/acetone bath), keeping the addition rate such that the reaction temperature did not go above −60° C. The solution was stirred at this temperature for 10 minutes then a solution of zinc chloride (1.56 g) in THF (7 ml) was added drop-wise. The solution was stirred for 15 minutes at −78° C. then the cooling bath removed and the reaction mixture allowed to warm to RT. An aliquot (1.2 ml) of the zinc oxazole solution was added via a syringe to a pre-sealed and nitrogen purged microwave vial (Biotage, 0.5-2.0 ml) containing N2,N2-dibenzyl-6-bromo-N4-(6-methyl-pyridin-3-ylmethyl)-3-nitropyridine-2,4-diamine (90 mg) and palladium bis(triphenylphosphine)dichloride (24 mg). The vial was heated under microwave irradiation (Biotage, Initiator 8) for 15 minutes at 130° C. Nine further aliquots of the zinc oxazole solution were reacted with the bromopyridine in the microwave in an analogous fashion.

All of the reaction mixtures were combined and concentrated in vacuo to a brown gum. The gum was partitioned between EtOAc (20 ml) and 2M ammonia solution (20 ml). The aqueous was re-extracted with EtOAc (20 ml), and the combined organics washed with brine (20 ml), then dried (MgSO$_4$) and evaporated to a brown gum. The crude was purified on Isco Companion on a silica column (120 g, Redisep), eluting with EtOAc:heptane, increasing the gradient linearly from 80:20 to 100:0 over 6 column volumes then isocratic at 100% EtOAc for 18 column volumes. The desired fractions were combined and evaporated to give the title compound as a yellow foamy solid (0.43 g).

$^1$H NMR (CDCl$_3$, 400 MHz) ☐ 2.60 (s, 3H), 4.55 (d, 2H), 4.60 (s, 4H), 6.99 (s, 1H) 7.05-7.15 (m, 4H), 7.20-7.22 (d, 2H), 7.22-7.35 (m, 6H), 7.59 (dd, 1H), 7.79 (s, 1H), 8.09 (t, 1H), 8.55 (d, 1H). LCMS R$_t$=2.87 m/z 507 [MH]$^+$

Preparation 129

N2,N2-Dibenzyl-N4-(6-methyl-pyridin-3-ylmethyl)-6-oxazol-2-yl-pyridine-2,3,4-triamine N2,N2-Dibenzyl-N4-(6-methyl-pyridin-3-ylmethyl)-3-nitro-6-oxazo-2-yl-pyridine-2,4-diamine (425 mg) was dissolved in THF (60 ml) then MeOH (60 ml) added. The solution was hydrogenated over Raney nickel (40 mg) under a hydrogen atmosphere (80 psi) for 1 h. The reaction mixture was filtered through a Celite pad then evaporated to yield the title compound as a crude yellow gum which was used directly in the next step.

LCMS R$_t$=2.42 m/z 477 [MH]$^+$

Preparation 130

(2,6-Dichloro-3-nitro-pyridin-4-yl)-carbamic acid ethyl ester

A solution of ethyl chloroformate (2.75 ml) in 2-methyl THF (10 ml) was added drop-wise to a cooled (ice bath) solution of 2,6-dichloro-4-amino-5-nitro-pyridine (5.00 g) and triethylamine (4.02 ml) in 2-methyl THF (50 ml). The rate of addition was such that the reaction temperature did not rise above 5° C. A precipitate formed on addition of the ethyl chloroformate. The suspension was allowed to warm to RT then left to stir under nitrogen for 16 h. The suspension was transferred to a separating funnel and water (50 ml) added. The layers were separated and the organics were washed with brine (50 ml) then dried (MgSO$_4$) and evaporated to an orange gum which solidified to a yellow solid on standing. The solid was re-crystallised from MeOH:water (70:30) providing the title compound as white needles that were collected by filtration (6.7 g).

$^1$H NMR (CDCl$_3$, 400 MHz) ☐ 1.25 (t, 3H), 4.31 (q, 2H), 8.10 (br, s, 1H), 8.40 (s, 1H). LCMS R$_t$=4.16 m/z 280 [MH]$^+$

Preparation 131

Benzyl-(2,6-dichloro-3-nitro-pyridin-4-yl)-carbamic acid ethyl ester

Benzyl bromide (2.33 ml) was added drop-wise to a stirred suspension of (2,6-dichloro-3-nitro-pyridin-4-yl)-carbamic acid ethyl ester (4.57 g) in acetonitrile (40 ml). The mixture was left to stir at RT under nitrogen for 16 h. The mixture was concentrated in vacuo then partitioned between EtOAc (50 ml) and water (50 ml). The layers were separated and the organics were washed with saturated NH$_4$Cl (50 ml), water (50 ml) and brine (50 ml). The organics were dried (MgSO$_4$) and evaporated to a yellow oil. This material was pre-absorbed onto silica then columned on Isco Companion on a silica column (330 g, Redisep) eluting with EtOAc:heptane, isocratic at 10:90 for 1 column volume (CV) then increasing the gradient from 10:90 to 30:70 over 6 CVs. The desired fractions were combined and evaporated to provide the title compound as a yellow oil (6.05 g).

$^1$H NMR (CDCl$_3$, 400 MHz) ☐ 1.25 (t, 3H), 4.19 (q, 2H), 4.81 (s, 2H), 6.88 (s, 1H), 7.20-7.28 (m, 2H), 7.30-7.40 (m, 3H). LCMS R$_t$=3.62 m/z 372 [MH]$^+$

Preparation 132

(2-Amino-6-chloro-3-nitro-pyridin-4-yl)-benzyl-carbamic acid ethyl ester

Benzyl-(2,6-dichloro-3-nitro-pyridin-4-yl)-carbamic acid ethyl ester (500 mg) was dissolved in THF (3 ml) in a ReactiVial. Ammonia (7M in MeOH, 1 ml) was added, the vial was sealed, and the reaction left to stir at RT for 48 h. The reaction mixture was then pre-absorbed directly onto silica and columned on Isco Companion on a silica column (40 g, Redisep), eluting with EtOAc:heptane, increasing the gradient linearly from 10:90 to 40:60 over 10 column volumes. The desired fractions were combined and evaporated to provide the title compound as a yellow gum which solidified on scratching (305 mg)

$^1$H NMR (CDCl$_3$, 400 MHz) ☐ 1.05 (t, 3H), 4.02 (q, 2H), 4.87 (br, s, 2H), 6.58 (s, 1h), 7.20-7.36 (m, 5H), 7.61 (br, s, 1H). LCMS R$_t$=3.24 m/z 351 [MH]$^+$

Preparation 133

[2-Amino-6-(2-methoxy-ethoxy)-3-nitro-pyridin-4-yl]-benzyl-carbamic acid ethyl ester Sodium hydride (21 mg) was added portion-wise to 2-methoxyethanol (0.5 ml). The resultant solution was added drop-wise to a solution of (2-amino-6-chloro-3-nitro-pyridin-4-yl)-benzyl-carbamic acid ethyl ester (100 mg) in THF (1.0 ml). The reaction mixture changed from yellow to deep red/orange solution and was left to stir at RT for 1 h. The orange mixture was concentrated in vacuo then partitioned between EtOAc (10 ml) and saturated NH$_4$Cl solution (10 ml). The layers were separated and the organics were washed with water (10 ml) and brine (10 ml) then dried (MgSO$_4$) and evaporated to provide the title compound as a crude yellow gum (111 mg). This was used directly in the next step with no further purification.

LCMS R$_t$=3.13 m/z 391 [MH]$^+$

Preparation 134

4-benzylamino-3-nitro-pyridin-2-ol 4-chloro-3-nitro-2-pyridone (5 g, 28.65 mmol) was suspended in 150 mL of acetonitrile then benzylamine (3.15 mL, 28.65 mmol) was added followed by potassium carbonate (4 g, 28.65 mmol) and the mixture was stirred at 60° C. overnight. The solvent was removed in vacuo and the residue was suspended in water (200 mL). A solution of HCl 2M was added until pH~6. The precipitate was filtered and dried in vacuo to give 4.75g of the title compound as a beige solid. A second crop from the mother liquids provided 1.4 g of the title compound.

$^1$H NMR (d6 DMSO) □: 11.20 (s broad, 1H), 9.35 (t, 1H), 7.40-7.20 (m, 6H), 5.85 (d, 1H), 4.60 (d, 2H). LRMS (ES$^+$) m/z 246 [MH]$^+$ Preparation 135

Benzyl-(2-chloro-3-nitro-pyridin-4-yl)-amine 4-benzylamino-3-nitro-pyridin-2-ol (6.15 g, 25.07 mmol) was suspended in 100 mL of acetonitrile then phosphorus oxychloride (12 mL, 125.40 mmol) was added followed by tetraethyl ammonium chloride (4.15 g, 25.07 mmol) and the mixture was stirred at 85° C. overnight. The solvent was removed in vacuo and the residue was suspended in water (300 mL) and extracted with dichloromethane (2×200 mL). The organic layer was dried over magnesium sulfate and the solvent was removed in vacuo to give 5.9 g of the title compound as a yellow solid.

$^1$H NMR (CDCl$_3$) □: 8.0 (d, 1H), 7.40-7.20 (m, 5H), 6.9 (s broad, 1H), 6.60 (d, 1H), 4.5 (d, 2H). LRMS (ES$^+$) m/z 264 [MH]$^+$ Preparation 136

N-2,N-2,N-4,tribenzyl-3-nitro-pyridine-2,4-diamine

Benzyl-(2-chloro-3-nitro-pyridin-4-yl)-amine (3.95 g, 14.99 mmol) was suspended in 50 mL of acetonitrile then dibenzylamine (2.9 mL, 14.99 mmol) was added followed by potassium carbonate (2 g, 14.99 mmol) and the mixture was stirred at 80° C. overnight. The solvent was removed in vacuo and the residue was suspended in water (100 mL) and extracted with ethyl acetate (2×100 mL). The organic layer was dried over magnesium sulfate and the solvent was removed in vacuo. The crude residue was purified by column chromatography on silica gel using 15% ethyl acetate in pentane to give 6 g of the title compound as a yellow oil.

$^1$H NMR (d6 DMSO) □: 8.1 (s broad, 1H), 7.9 (d, 1H), 7.40-7.10 (m, 15H), 6.10 (d, 1H), 4.55 (s, 4H), 4.5 (d, 2H). LRMS (ES$^+$) m/z 425 [MH]$^+$ Preparation 137

N-2,N-2,N-4,tribenzyl-pyridine-2,3,4-triamine

N-2,N-2,N-4,tribenzyl-3-nitro-pyridine-2,4-diamine (6 g, 14.13 mmol) was suspended in 150 mL of ethanol and Raney nickel (1.2 g, 20% weight) was added, then the mixture was stirred at room temperature under 50 psi of hydrogen for 3 hours. After completion, the mixture was filtered through arbocel and the solvent was removed in vacuo to give 5 g of the title compound as a pale purple gum.

$^1$H NMR (CDCl$_3$) □: 7.80 (d, 1H), 7.40-7.15 (m, 15H), 6.35 (d, 1H), 4.35 (d, 2H), 4.15 (s, 4H).3.5-3.25 (s broad, 2H). LRMS (ES$^+$) m/z 395 [MH]$^+$ Preparation 138

1-benzyl-4-dibenzylamino-1,3-dihydro-imidazo[4,5,c]pyridine-2-one

N-2,N-2,N-4,tribenzyl-pyridine-2,3,4-triamine (5 g, 12.67 mmol) was dissolved in 100 mL of acetonitrile then 1,1'-carbonyldiimidazole (3 g, 19.701 mol) was added and the reaction was stirred at 80° C. overnight. The mixture was cooled down to room temperature and the precipitate was filtered and washed with acetonitrile then dried in vacuo to give 4.3 g of the title compound as a light purple solid.

$^1$H NMR (d6 DMSO) □: 10.9 (s, 1H), 7.75 (d, 1H), 7.40-7.10 (m, 15H), 6.70 (d, 1H), 4.9 (s, 2H), 4.6 (s, 4H). LRMS (ES$^+$) m/z 421 [MH]$^+$

Preparation 139

1-benzyl-7-bromo-4-dibenzylamino-1,3-dihydro-imidazo[4,5,c]pyridine-2-one 1-benzyl-4-dibenzylamino-1,3-dihydro-imidazo[4,5,c]pyridine-2-one (1 g, 2.4 mmol) was suspended in 20 mL of acetic acid then sodium acetate (195 mg, 2.4 mmol) was added followed by bromine (456 mg, 2.85 mmol) dropwise. The mixture was stirred at room temperature for 15 minutes. A heavy precipitate was formed. The mixture was diluted in water (50 mL) and the solid was filtered and washed with water. It was then diluted in ethyl acetate (20 mL), dried over magnesium sulfate and the solvent was removed in vacuo to give 1.29 g of the title compound as a light orange solid.

$^1$H NMR (d6 DMSO) □: 11.5 (s, 1H), 7.85 (s, 1H), 7.40-7.10 (m, 15H), 5.30 (s, 2H), 4.55 (s, 4). LRMS (ES$^+$) m/z 499,501 [MH]$^+$

Preparation 140

1-benzyl-4-dibenzylamino-2-oxo-2,3-dihydro-1H-imidazo[4,5,c]pyridine-7-carboxylic acid methyl ester 1-benzyl-7-bromo-4-dibenzylamino-1,3-dihydro-imidazo[4,5,c]pyridine-2-one (500 mg, 1 mmol) was suspended in 30 mL of methanol then triethylamine (203 mg, 2 mmol) was added followed by (1,1'bis(diphenylphosphino)ferrocene) dichloro palladium (82 mg, 0.1 mmoml) and the mixture was stirred at 100° C. under 100 psi of CO overnight. The mixture was cooled down to room temperature, filtered through Arbocel and washed with methanol. The solvent was removed in vacuo and the residue was purified by column chromatography on silica gel using 1% of methanol in dichloromethane to give 21 mg of the title compound as a white solid.

¹H NMR (CDCl₃) □: 8.4 (s, 1H), 8.0 (s broad, 1H), 7.40-7.00 (m, 15H), 5.45 (s, 2H), 4.80 (s, 4H), 3.7 (s, 3H). LRMS (ES⁺) m/z 479 [MH]⁺

Preparation 141

1-benzyl-4-dibenzylamino-2-oxo-2,3-dihydro-1H-imidazo[4,5,c]pyridine-7-carboxylic acid cyclopropylmethyl-amide 1-benzyl-4-dibenzylamino-2-oxo-2,3-dihydro-1H-imidazo[4,5,c]pyridine-7-carboxylic acid methyl ester (50 mg, 0.1 mmol) was suspended in 2 mL of (aminomehtyl) cyclopropane and the mixture was stirred at 120° C. overnight. The excess of amine was removed in vacuo and the gum was partitioned in water (20 mL) and ethyl acetate (50 mL), the organic layer was isolated, dried over MgSO4 and the solvent was removed in vacuo. The residue was purified by column chromatography on silica gel using 5% of methanol in dichloromethane to give 10 mg of the title compound as a yellow gum.

LRMS (ES⁺) m/z 518 [MH]⁺

Preparation 142

6-Chloro-2,4-dihydroxy-5-methyl-pyridine

Malonyl dichloride (10 g, 71 mmol) and propionitrile (12 mL) were combined and stirred at room temperature for 16 h under a nitrogen atmosphere. To the resulting heterogenous mixture was added 50 mL dioxan, and the resulting precipitate was collected by filtration and washed with cold dioxan. The collected solid was dissolved in a few mL's of methanol and precipitated once more with dioxan. The solid was collected by filtration, washed with dioxan and dried in vacuo to give the title compound as a white solid (6 g, 53%).

LRMS: (ES⁺) m/z 160 [MH]⁺.

Preparation 143

6-Chloro-2,4-dihydroxy-5-methyl-3-nitro-pyridine

6-Chloro-2,4-dihydroxy-5-methyl-pyridine (500 mg, 3.1 mmol) was taken up in acetic acid (1 mL), cooled to 0° C. and nitric acid added (4 mL) dropwise with stirring. After the addition was complete, the ice bath was removed, and the reaction mixture was allowed to warm to room temperature over 16 h. Ice was added to the mixture to provide a precipitate, which was collected by filtration and dried in vacuo to give the title compound as a yellow solid (180 mg, 28%).

LRMS: (ES+) m/z 205 [MH]+

Preparation 144

Diphenyl malonate

Malonic acid (11 g, 106 mmol) was mixed with phenol (20 g, 212 mmol) at 0° C. under nitrogen and phosphorus oxychloride (11.5 mL, 123 mmol) was added dropwise to the solid mixture. The resulting mixture was stirred at 0° C. for 5 mins, and then heated at reflux for 5 h, causing the solid to melt and an orange solution to form. The reaction was cooled to room temperature, and then poured onto 100 mL water and extracted with diethyl ether (3×75 mL). The combined organics were washed with brine, dried over MgSO₄, concentrated in vacuo to an orange oil of the title compound. (27 g, 99%).

¹HNMR (CDCl₃, 400 MHz) 3.86 (s, 2H), 7.17 (m, 4H), 7.27 (m, 2H), 7.41 (m, 4H). LRMS (ES) m/z 257 [MH]+

Preparation 145

Cyclopentanone-tert-butyl imine

Cyclopentanone (13.3 mL, 150 mmol) and tert-butylamine (47.4 mL, 450 mmol) were combined in 110 mL diethyl ether under a nitrogen atmosphere and were then cooled to −55° C. in a dry ice/acetonitrile bath. Titanium tetrachloride (8.2 mL, 75 mmol) was taken up in 70 mL pentane and added dropwise to the above solution, being careful to maintain the temperature at −40° C. the reaction was then stirred at −40° C. for 6 h and was then allowed to warm to room temperature overnight. The reaction mixture was filtered through a short plug of celite and washed with diethyl ether. The filtrate was evaporated in vacuo to yield 15.9 g (76%) of the title product as a clear oil.

¹HNMR (CDCl₃, 400 MHz) 1.26 (s, 9H), 1.67 (m, 2H), 1.82 (m, 2H), 2.29 (t, 2H), 2.36 (t, 2H).

Preparation 146

6,7-Dihydro-5H-[1]pyridine-2,4-diol

Cyclopentanone-tert-butyl imine (2.78 g, 20 mmol) and diphenyl malonate (5.12 g, 20 mmol) were combined in 40 mL triglyme and heated at 100 C for 4 h, and then at 200 C for 2 h. The reaction was then allowed to cool to room temperature before pouring into 200 mL diethyl ether and storing in the freezer in a sealed flask for 4 days. The resulting precipitate was filtered, washed with diethyl ether and dried in vacuo to yield the title compound (1.45 g, 50%) as a light brown solid.

¹HNMR (CD₃OD, 400 MHz) 2.12 (m, 2H), 2.70 (t, 2H), 2.82 (t, 2H), 5.64 (s, 1H).

Preparation 147

5,6-Dimethyl-pyridin-2,4-diol 5,6-Dimethyl-4-hydroxy-2-oxo-2H-pyran (J. Chem. Soc. Perkin Trans 1, 1980, 2272) (10 g, 71 mmol) was dissolved in 66 mL of dioxan and 33 mL of 0.88 NH₃ solution and the mixture refluxed for 3 h. The resulting suspension was then allowed to cool to room temperature overnight, filtered and the solid collected and dried in vacuo to provide the title compound as a white crystalline solid (6.5 g). The filtrate was concentrated to approximately 10 mL in vacuo, and a second crop of solid collected by filtration (1.0 g). Both crops were combined and used in the next synthetic step.

¹H NMR (DMSO, 400 MHz): δ 1.77 (s, 3H), 2.06 (s, 3H), 5.42 (s,1 H). LRMS m/z (APCI⁺) 140 [MH]⁺.

Preparation 148

5,6-Dimethyl-3-nitro-pyridin-2,4-diol 5,6-Dimethyl-pyridin-2,4-diol (6.5 g, 47 mmol) was stirred in 30 mL sulphuric acid and then cooled to 0° C. in an ice bath. Fuming nitric acid (10 mL) was added dropwise, and the mixture allowed to stir for 1 h after complete addition. The reaction mixture was poured onto crushed ice and the resulting yellow solid collected by filtration to give the title compound (3.9 g, 46%).

¹H NMR (MeOD, 400 MHz): δ 2.04 (s, 3H), 2.31 (s, 3H). LRMS m/z (APCI⁺) 185 [MH]⁺.

Preparation 149

2,4-Dichloro-5,6-Dimethyl-3-nitro-pyridine 5,6-Dimethyl-3-nitro-pyridin-2,4-diol (3.9 g, 21 mmol) was dissolved in acetonitrile (150 mL) and firstly tetraethylammonium chloride (7.1 g, 42 mmol) and then phosphorus oxychloride (19.9 mL, 210 mmol) were added and the whole heated at 70C for 16 h. The reaction mixture was poured into crushed ice and extracted with DCM (2×30 mL). The combined extracts were dried over MgSO₄, filtered and concentrated in vacuo to afford a brown solid. This solid was taken up in 2 mL DCM and filtered through a short plug of silica gel eluting with 2:1 pentane:EtOAc. The filtrate was then evaporated to afford the title compound as a light brown solid (3.5 g, 75%).
¹H NMR (CDCl₃, 400 MHz): δ 2.61 (s, 3H), 2.41 (s, 3H)

Preparation 150

Benzyl-(2-chloro-5,6-dimethyl-3-nitro-pyridin-4-yl)-amine 2,4-Dichloro-5,6-Dimethyl-3-nitro-pyridine (2 g, 9 mmol) was dissolved in acetonitrile (100 mL) and benzylamine (1.0 mL, 9.5 mmol). Potassium carbonate (1.3 g, 9.5 mmol) was added in one portion, and the whole was heated at 55° C. for 16 h. The reaction mixture was diluted with EtOAc and washed with 50 mL water. The aqueous was re-extracted with EtOAc, the organics were combined and then dried over MgSO₄ and evaporated to a dark red residue. This residue was purified by column chromatography on silica gel using 8:1 pentane:EtOAc as eluant to afford the title compound as a bright orange solid (1.2 g, 45%).
1H NMR (CDCl₃, 400 MHz): δ 2.09 (s, 3H), 2.47 (s, 3H), 4.25-4.27 (d, 2H), 4.52 (bs, 1H), 7.28-7.30 (m, 2H), 7.35-7.41 (m, 3H) LRMS m/z (APCI⁺) 292 [MH]⁺.

Preparation 151

N2,N2-Diallyl-N4-benzyl-5,6-dimethyl-3-nitro-pyridine-2,4-diamine

Benzyl-(2-chloro-5,6-dimethyl-3-nitro-pyridin-4-yl)-amine (1.2 g, 4.1 mmol) was dissolved in ethoxyethanol (60 mL) and diisopropylethylamine (1.1 mL, 6.2 mmol) and diallylamine (0.76 mL, 6.2 mmol) added in one portion. The reaction mixture was heated in a sealed vessel at 100° C. overnight, and then concentrated in vacuo to an orange residue. This residue was purified directly by column chromatography on silica gel, using a gradient of 8:1→1:1 pentane:EtOAc as eluant to provide the title compound as a bright orange oil (938 mg, 65%).
¹H NMR (CDCl₃, 400 MHz): δ 2.16 (s, 3H), 2.34 (s, 3H), 3.90-3.92 (d, 4H), 4.33-4.34 (d, 2H), 5.13-5.21 (m, 4H), 5.77-5.87 (m, 2H), 6.37-6.40 (bt, 1 H), 7.35-7.28 (m, 5H). LRMS m/z (APCI⁺) 353 [MH]⁺

Preparation 152

N2,N2-Diallyl-N4-benzyl-5,6-dimethyl-pyridine-2,3,4-triamine

N2,N2-Diallyl-N4-benzyl-5,6-dimethyl-3-nitro-pyridine-2,4-diamine (828 mg, 2.4 mmol) was dissolved in ethanol (15 mL) and 2N HCl (15 mL) and iron powder (527 mg, 9.6 mmol) was added in one portion. The reaction mixture was heated at 70° C. for 2 h, and then cooled to room temperature and poured into 50 mL water. The resulting solution was neutralised with 1N NaOH solution to give a dark green suspension, which was extracted with EtOAc (2×25 mL) and the combined organics were dried over MgSO₄, filtered and evaporated to give the title compound as a dark green oil (559 mg, 74%).
¹H NMR (CDCl₃, 400 MHz): δ 1.95 (s, 3H), 2.32 (s, 3H), 3.73-3.74 (d, 4H), 4.21 (s, 2H), 5.07-5.23 (m, 4H), 5.86-5.96 (m, 2H), 7.26-7.32 (m, 5H). LRMS m/z (APCI⁺) 323 [MH]⁺

Preparation 153

1-Benzyl-4-diallylamino-6,7-dimethyl-1,3-dihydro-imidazo[4,5-c]pyridin-2-one

N2,N2-Diallyl-N4-benzyl-5,6-dimethyl-pyridine-2,3,4-triamine (559 mg, 1.7 mmol) was taken up in acetonitrile (50 mL), and 1,1-carbonyldiimidazole (2.8 g, 17 mmol) was added in one portion, and the whole refluxed for 2 h. The reaction mixture was allowed to cool to room temperature, and was then concentrated in vacuo and purified directly by column chromatography on silica gel using a gradient of 8:1→4:1 pentane:EtOAc as eluant to afford the title compound as a white solid (258, 59%).
¹H NMR (CDCl₃, 400 MHz): δ 2.12 (s, 3H), 2.34 (s, 3H), 3.99-4.01 (dt, 4H), 5.25-5.28 (m, 4H), 5.34-5.40 (d, 2H), 6.01-6.10 (m, 2H), 7.11-7.13 (d, 2H), 7.24-7.32 (m, 3H), 7.66(bs, 1H). LRMS m/z (ESCI⁺) 349 [MH]⁺

Preparation 154

4-Methyl-3-oxo-pentanoic acid

Ethyl isobutyrylacetic acid (21 g, 132 mmol) was taken up in a 1.5M sodium hydroxide solution (15 g in 250 mL water) and stirred at room temperature over 16 h. The solution was cooled to 0° C. in an ice bath and was then acidified with 35 mL conc. Hydrochloric acid to pH 1-2. The resulting solution was saturated with sodium chloride and was then extracted with ethyl acetate (3×300 mL). The combined extracts were dried over sodium sulfate and then filtered and concentrated in vacuo to give the title compound as a clear oil (16.4 g, 95%).
¹HNMR (CDCl₃, 400 MHz, approx. 4:1 mixture of keto and enol tautomers) ☐(major keto form) 1.15-1.16 (d, 6H), 2.75-2.71 (m, 1H), 3.56 (s, 2H).

Preparation 155

4-Hydroxy-3-isobutyryl-6-isopropyl-pyran-2-one

4-Methyl-3-oxo-pentanoic acid (16.4 g, 126 mmol) was taken up in THF (200 mL) at room temperature under a nitrogen atmosphere, and 1,1-carbonyldiimidazole (22.4 g, 138 mmol) was added in one portion. The reuslting yellow solution was stirred at room temperature for 16 h, and then concentrated in vacuo and the residue diluted with DCM (200 mL). The solution was washed with 2N HCl (100 mL) and water (100 mL) and the aqueous was re-extracted with DCM (50 mL). The combined organics were dried over sodium sulfate and were then concentrated in vacuo to give the title compound as a yellow oil (11.7 g, 80%).
¹HNMR (CDCl₃, 400 MHz) ☐1.16-1.18 (d, 6H), 1.25-1.27 (d, 6H), 2.71-2.74 (m, 1H), 3.94-3.97 (m, 1H), 5.92 (s, 1H). LRMS (APCI+) m/z 225 [MH]+

Preparation 156

4-Hydroxy-6-isopropyl-pyran-2-one

4-Hydroxy-3-isobutyryl-6-isopropyl-pyran-2-one (11.7 g, 52 mmol) was taken up in conc. Sulfuric acid (40 mL) and stirred at 130° C. for 15 mins. The dark oil obtained was left to cool to room temperature and was then cooled further to 0° C. in an ice bath before the addition of 200 mL crushed ice with stirring. The resulting solution was extracted with ethyl acetate (3×200 mL) and the combined organics were dried over sodium sulfate, filtered and evaporated in vacuo to a light brown oil that was purified by column chromatography using a gradient of pentane in ethyl acetate 3:1→30:70 as eluant to provide the title compound as a light brown oil which solidified on standing (6.1 g, 77%).

$^1$HNMR (CDCl$_3$, 400 MHz) ☐ 1.20-1.22 (d, 6H, 2.70-2.80 (m, 1H), 5.58 (s, 1H), 5.99 (s, 1H). LRMS (APCI+) m/z 155 [MH]+

Preparation 157

Ethyl-2,4-diaminobenzyl-6-methyl-3-carboxylate

Ethyl-2,4-dichloro-6-methyl-3-carboxylate (100 mg, 0.43 mmol) was dissolved in acetonitrile (2 ml) and treated firstly with triethylamine (240 ☐l, 1.70 mmol) and then with benzylamine (112 ☐l, 1.02 mmol) and the reaction mixture stirred at 40° C. for 18 hours under nitrogen. After cooling to room temperature, the reaction was poured into water and the mixture extracted with ethyl acetate (3×5 ml). Combined organics were dried (MgSO$_4$), and evaporated to give a crude oil that was purified by column chromatography on silica gel, eluting with pentane: ethyl acetate, 20:1 to 5:1. The title compound was obtained as a clear oil, (98 mg, 61%).

$^1$H-NMR (CDCl$_3$, 400 MHz): ☐1.21 (t, 3H), 2.25 (s, 3H), 4.29 (q, 2H), 4.40, (d, 2H), 4.78 (d, 2H), 5.81 (s, 2H), 7.21-7.42 (m, 10H), 8.10 (brs, 1H), 8.30 (brs, 1H). LRMS m/z (ESI) 376 [MH]$^+$ Preparation 158

2,4-Diaminobenzyl-6-methyl-3-carboxylic acid

Ethyl-2,4-diaminobenzyl-6-methyl-3-carboxylate (40 mg, 0.11 mmol) was dissolved in methanol (1 ml) and treated with a 2N solution of sodium hydroxide (60 ☐l, 0.12 mmol) and the reaction mixture stirred at 65° C. for 5 hours under nitrogen. After cooling to room temperature, the reaction was poured into water, the pH adjusted to 6-7 using 2N hydrochloric acid, and the mixture extracted with ethyl acetate (3×5 ml). Combined organics were dried (MgSO$_4$), and evaporated to provide the title compound as an off-white solid, (37 mg, quant).

$^1$H-NMR (DMSO, 400 MHz): ☐2.22 (s, 3H), 4.59, (d, 2H), 4.64, (d, 2H), 6.20 (s, 2H), 7.20-7.39 (m, 10H). LRMS m/z (ESI) 348 [MH]$^+$, 346 [M−H]$^−$

Preparation 159

6-Benzylamino-9-benzyl-2-methyl-8-oxo-8,9-dihydro-7H-purine and 4-Benzylamino-9-benzyl-6-methyl-8-oxo-8,9-dihydro-7H-purine

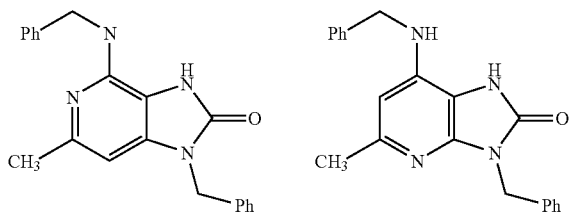

2,4-Diaminobenzyl-6-methyl-3-carboxylic acid (30 mg, 0.09 mmol), diphenylphosphoryl azide (25 mg, 0.09 mmol) and triethylamine (14 ☐l, 0.10 mmol) were combined in toluene and the reaction heated at 111° C. for 16 hours under nitrogen. After cooling to room temperature, the reaction was poured into water and the mixture extracted with ethyl acetate (3×5 ml). Combined organics were dried (MgSO$_4$), to give a crude oil that was purified by column chromatography on silica gel, eluting with pentane : ethyl acetate, 1:1, providing the separate title compounds both as clear oils, (10 mg (I), 11 mg (II), 68% combined yield).

$^1$H-NMR (CDCl$_3$, 400 MHz): (I) ☐2.39 (s, 3H), 4.7, (s, 4H), 6.04 (s, 2H), 7.15-7.39 (m, 10H). LRMS m/z (ESI) 354 [MH]$^+$; (II) ☐2.39 (s, 3H), 4.39, (d, 2H), 5.01, (s, 2H), 6.19 (s, 2H), 7.15-7.39 (m, 10H). LRMS m/z (ESI) 354 [MH]$^+$

Preparation 160

1-Benzyl-2-bromo-1H-imidazole-5-iodo-4-carbonitrile

5-Amino-1-benzyl-2-bromo-1H-imidazole-4-carbonitrile (50 mg, 0.18 mmol) was dissolved in diiodomethane (1 ml) and the mixture heated to 100° C. Isoamyl nitrite (97 ☐l, 0.72 mmol) was then added dropwise via syringe to the heated reaction mixture. Gas evolution was observed. Following 30 minutes the reaction was allowed to cool to room temperature and solvents were removed under high vacuum. The remaining crude red residue was purified by column chromatography over silica gel eluting with 100% pentane to 7:3 pentane: ethyl acetate. This provided the title compound as a yellow oil (40 mg, 60%).

$^1$H-NMR (CDCl$_3$, 400 MHz): ☐5.22 (s, 2H), 6.71 (s, 2H), 7.09 (m, 2H), 7.28-7.40 (m, 3H). LRMS m/z (ESI) 388/390 [MH]$^+$

Preparation 161

1-Benzyl-2-bromo-5-(4-hydroxybut-1-yne)-1H-imidazole-4-carbonitrile (I) and 2-(4-Amino-1-benzyl-2-bromo-1H-imidazo[4,5-c]pyridin-6-yl)-ethanol (II)

1-Benzyl-2-bromo-1H-imidazole-5-iodo-4-carbonitrile (39 mg, 0.1 mmol) was dissolved in acetonitrile (1 ml) and the mixture treated with triethylamine (20 ☐l, 0.15 mmol), Pd(PhCN)$_2$Cl$_2$ (3.8 mg, 0.01 mmol), and but-1-yn-4-ol (9 ☐l, 0.12 mmol). The reaction was then heated in a sealed tube at 100° C. for 2 hours. The reaction was allowed to cool to room temperature and solvents were removed under vacuum. A 7N solution of ammonia in methanol was then added to the remaining crude brown residue and the reaction heated in a sealed tube at 120° C. for 18 hours. Volatile components were then removed under vacuum providing a crude brown oil. LRMS of this material showed that the major component was the cyclised material (II), m/z (ESI) 347/349 [MH]$^+$. This oil was then purified by column chromatography over silica gel eluting with 10% pentane in ethyl acetate, providing the title compound (I) as a yellow oil (6 mg). Compound (II) was not recovered from the silica gel column.

$^1$H-NMR (CDCl$_3$, 400 MHz): (I) ☐2.75 (t, 2H), 3.79 (t, 2H), 5.2 (s, 2H), 7.18 (m, 2H), 7.22-7.38 (m, 3H). LRMS m/z (ESI) 330/332 [MH]$^+$

Preparation 162

1-Benzyl-5-(-but-4-hydroxy-2-keto-1-yl)-1H-imidazole-2-methoxy-4-carbonitrile

1-Benzyl-2-bromo-5-(4-hydroxybut-1-yne)-1H-imidazole-4-carbonitrile (6 mg, 0.02 mmol) was dissolved in methanol (1 ml) and the mixture treated with sodium methoxide (5 mg, xs). The reaction was then heated at 65° C. for 12 hours. The reaction was allowed to cool to room temperature and solvents were removed under vacuum. A 2N solution of hydrochloric acid was then added to the remaining crude residue and the reaction stirred at room temperature for 2 hours. Volatile components were then removed under vacuum providing a crude white solid containing mostly the title compound.

LRMS m/z (ESI) 300 [MH]+.

Preparation 163

2,6-Dichloro-4-(N-nitro)amino-pyridine 2,6-Dichloro-4-amino pyridine (1.58 g) was taken up in sulfuric acid (20 mL) at 0° C. under a nitrogen atmosphere and nitric acid (2.5 mL) added dropwise. After 30 mins, the reaction turned to an orange colour and was poured slowly into ice water. The precipitate was filtered, washed with water and then dissolved in ethyl acetate. The organic solution was then dried over $MgSO_4$, filtered and evaporated in vacuo to give the title compound (1.7 g) as a yellow solid.

$^1$H NMR ($CDCl_3$, 400 MHz) ☐ 7.40 (s, 2H), 10.4 (s, 1H).

Preparation 164

2,6-Dichloro-4-amino-5-nitro-pyridine 2,6-Dichloro-4-(N-nitro)amino-pyridine (1.7 g) Was taken up in sulfuric acid (10 mL) and heated at 90° C. for 30 mins. The reaction mixture was cooled to room temperature, then poured into ice water to produce a precipitate. The yellow solid was filtered off, collected, dissolved in ethyl acetate and then washed with an aqueous $Na_2CO_3$ solution. The organics were then further washed with brine, then dried over $MgSO_4$, filtered and evaporated in vacuo to give the title compound (1.45 g) as a yellow solid.

$^1$H NMR ($CDCl_3$, 400 MHz) ☐ 5.70 (s, 2H), 6.70 (s, 1H). LRMS (ES+) m/z 209 [MH]+

Preparation 165

2,6-Dibromo-4-amino-5-nitro-pyridine 2,6-Dichloro-4-amino-5-nitro-pyridine (2 g) Was taken up in a 33% solution of HBr in acetic acid (20 mL) and heated at 90° C. in a Teflon-lined bomb for 72 h. The reaction mixture was cooled to room temperature, poured into ice water to produce a precipitate. The resulting solid was filtered off, collected, dissolved in ethyl acetate and then washed with an aqueous $K_2CO_3$ solution. The organics were then further washed with brine, then dried over $MgSO_4$, filtered and evaporated in vacuo to give the title compound (2 g) as a pale yellow solid.

$^1$H NMR ($CDCl_3$, 400 MHz) ☐ 5.60 (s, 2H), 6.90 (s, 1H). LRMS (ES+) m/z 295, 297, 299 [MH]+

Preparation 166

2,6-Dibromo-4-chloro-5-nitro-pyridine 2,6-Dibromo-4-amino-5-nitro-pyridine (3 g) was taken up in concentrated hydrochloric acid (20 mL) and cooled to 0° C. Sodium nitrite (3.5 g) was added and the reaction mixture was allowed to stir at 0° C. for 1 h. The ice bath was removed and the reaction allowed to warm to room temperature over 3 h, and was then quenched by the addition of ethyl acetate (50 mL) and water (100 mL). The organic layer was separated, dried over $MgSO_4$ and filtered and evaporated in vacuo to a pale yellow oil, which was purified by column chromatography using 35:1 pentane:EtOAc as eluant to give the title compound (2.2 g) as a white solid.

$^1$H NMR ($CDCl_3$, 400 MHz) ☐ 7.65 (s, 1H).

Preparation 167

N-2,N-4-Dibenzyl-6-bromo-3-nitro-pyridine-2,4-diamine 2,6-Dibromo-4-amino-5-nitro-pyridine (1.53 g) Was taken up in THF (20 mL) and firstly solid $K_2CO_3$ (100 mg) and then benzylamine (1.1 mL) were added in one portion each. The reaction mixture was then heated at 70° C. for 16 h. The solvent was removed in vacuo, and the crude residue was purified by column chromatography on silica gel using 10% ethyl acetate in pentane as the eluant to give the title compound (1.2 g) as a yellow oil.

$^1$H NMR ($CDCl_3$, 400 MHz) ☐ 4.45 (d, 2H), 4.78 (d, 2H), 6.20 (s, 1H), 7.20-7.41 (m, 10H), 9.41 (s, 1H), 9.50 (s, 1H). LRMS (ES+) m/z 413, 415 [MH]+

Preparation 168

4,6-Bis-benzylamino-5-nitro-pyridine-2-carboxyli acid methyl ester

N-2,N-4-Dibenzyl-6-bromo-3-nitro-pyridine-2,4-diamine (1 g) Was taken up in a mixture of methanol and DMF (2:1, 15 mL), and firstly triethylamine (0.7 mL), then triphenylphosphine (30 mg), and finally palladium acetate (27 mg) was added and the mixture was heated at 60° C. and 100 psi carbon monoxide pressure for 16 h. The reaction mixture was cooled to room temperature, filtered through a short plug of Arbocel and evaporated in vacuo to give a yellow residue. This residue was purified by column chromatography on silica gel using a gradient of 8:1→2:1 pentane in ethyl acetate as the eluant to give the title compound (0.5 g) as a pale yellow solid.

$^1$H NMR ($CDCl_3$, 400 MHz) ☐ 3.91 (s, 2H), 4.58 (s, 1H), 4.85 (d, 2H), 6.85 (s, 1H), 7.05-7.25 (m, 10H), 9.3 (t, 1H), 9.55 (t, 1H). LRMS (ES+) m/z 393 [MH]+

Preparation 169

5-Amino-4,6-benzylamino-pyridin-2-carboxylic acid methyl ester 4,6-Bis-benzylamino-5-nitro-pyridine-2-carboxyli acid methyl ester (800 mg) Was taken up in methanol (30 mL), and Raney nickel (80 mg) was added in one portion and the mixture was stirred at room temperature for 3 h under 60 psi hydrogen pressure. The reaction mixture was filtered through a short plug of Arbocel and the filtrate was evaporated in vacuo to give a yellow residue of the title compound (0.75 g) which was used with no further purification.

LRMS (ES+) m/z 363 [MH]+

Preparation 170

1-Benzyl-4-benzylamino-2-oxo-2,3-dihydro-1H-imidazo[4,5-c]pyridine-6-carboxylic acid methyl ester 5-Amino-4,6-benzylamino-pyridin-2-carboxylic acid methyl ester (0.75 g) Was taken up in acetonitrile (40 mL), and 1,1-carbonyldiimidazole (500 mg) added in one portion and the mixture heated at 80° C. for 6 h. The reaction mixture was evaporated in vacuo to give a residue which was purified by column chromatography on silica gel using 1:1 pentane in ethyl acetate as the eluant to give the title compound (100 mg) as a white solid.

$^1$H NMR (d6-DMSO, 400 MHz) ☐ 3.75 (s, 3H), 4.45 (d, 2H), 4.98 (s, 2H), 6.48 (t, 1H), 7.18 (s, 1H), 7.22-7.47 (m, 10H). LRMS (ES+) m/z 389 [MH]+

Preparation 171

1-Benzyl-4-benzylamino-2-oxo-2,3-dihydro[4,5-c] pyridine-6-carboxylic acid

1-Benzyl-4-benzylamino-2-oxo-2,3-dihydro-1H-imidazo [4,5-c]pyridine-6-carboxylic acid methyl ester (0.03 g) Was taken up in methanol (1 mL), and 1N NaOH solution (2 mL) and the mixture was stirred at 40C. After 2 h, 2 mL of 2N HCl was added, which caused a solid to precipitate out. This solid was filtered off and dried in vacuo to give the title compound (25 mg) as a white solid.

$^1$H NMR (CDCl$_3$, 400 MHz) ☐ 4.30 (s, 2H), 4.90 (s, 2H), 7.10-7.35 (m, 11H), 10.80 (s, 1H). LRMS (ES+) m/z 375 [MH]+

Preparation 172

1-benzyl-4-benzylamino-2-oxo-2,3-dihydro-1H-imidazo[4,5-c]pyridine-6-carboxylic acid cyclopropylmethylamide 1-Benzyl-4-benzylamino-2-oxo-2,3-dihydro-1H-imidazo [4,5-c]pyridine-6-carboxylic acid methyl ester (0.05 g) Was taken up in cyclopropylmethylamine (1 mL) and heated in a ReactiVial at 80° C. for 3 h. The solvent was removed in vacuo and diethyl ether was added which caused a solid to precipitate out. This solid was filtered off and dried in vacuo to give 40 mg of a white solid. This solid was purified by preparative HPLC using mixtures of acetonitrile, water and diethylamine as the eluant to give the title compound as a white solid (18 mg).

$^1$H NMR (CDCl$_3$, 400 MHz) ☐ 0.22 (q, 2H), 0.55 (q, 2H), 1.05 (m, 1H), 3.22 (t, 2H), 4.35 (d, 2H), 4.90 (s, 2H), 5.90 (t, 1H), 7.10-7.35 (m, 11H), 7.85 (t, 1H). LRMS (ES+) m/z 428 [MH]+

Preparation 173

4-Bromo-2-chloro-6-trifluoromethyl-pyridin-3-ylamine

6-Trifluoromethyl-pyridin-3-ylamine (150 g, 925 mmol) was suspended in 500 ml acetonitrile. Added to the solution was N-Chlorosuccinimide (124 g, 925 mmol) and the mixture heated at 80° C. for 2 h after which N-bromosuccinimide (165 g, 925 mmol) was added and the mixture heated at 80° C. for a further 3 h. The rm was cooled to ambient temperature, concentrated in vacuo and triturated in 100 ml diethyl ether, removing the precipitate by filtration. The resulting filtrate was concentrated in vacuo and purified by column chromatography on silica, eluting with Hept:EtOAc, 4:1 to give the title compound as a dark red oil (220 g, 86%).

$^1$H NMR (CDCl$_3$) ☐ 4.90 (bs, 2H), 7.67(s, 1H); LRMS (ES) m/z 275/277 [MH]+

Preparation 174

N*4*-Benzyl-2-chloro-6-trifluoromethyl-pyridine-3, 4-diamine

4-Bromo-2-chloro-6-trifluoromethyl-pyridin-3-ylamine (84 g, 300 mmol) was stirred in 500 ml DMSO in the presence of caesium fluoride (46.3 g, 305 mmol) and benzylamine (66.6 ml, 610 mmol). The resulting brown suspension was heated at 150° C. for 16 h. Added to the cooled suspension was 1500ml water and the mixture extracted with 2×500 ml diethyl ether. The combined organic extracts were dried (MgSO$_4$), concentrated in vacuo and purified by column chromatography on silica, eluting with Hept:EtOAc, 4:1 to 2:1 to give the title compound (15.8 g, 17%) as a pale brown solid. The undesired isomer was similarly isolated as a brown oil (51.0 g, 48%).

$^1$H NMR (CDCl$_3$) ☐ 3.76(bs, 2H), 4.39-4.41(d, 2H), 4.53 (bs, 1H), 6.85(s, 1H), 7.34-7.40(m, 5H); LRMS (ES) m/z 302 [MH]+.

Preparation 175

4,6-dihydroxy-2-trifluoromethyl-nicotinic acid ethyl ester

In a three necked flask, potassium tert-butoxide (5.8 g, 51.9 mmol) was suspended in 100 mL of tetrahydrofuran and a solution of diethyl-1,3-acetonedicarboxylate (10 g, 49.5 mmol) in 30 mL of tetrahydrofuran was slowly added. Once the addition was complete, the mixture was stirred at room temperature for 30 minutes. In a second three necked flask set up with a gas outlet linked to the first three necked flask, 2,2,2-trifluoroacetamide (11.2 g, 98.9 mmol) was dissolved in 80 mL of pyridine and a premixed solution of trifluoroacetic anhydride (20.8 g, 98.9 mmol) in 30 mL of pyridine was added slowly, the gas formed (2,2,2-trifluoromethylacetonitrile) was directly bubbled through the first three necked flask. Once the addition was complete, the mixture in the second three necked flask was stirred at room temperature for 30 minutes then the solvent was removed in vacuo and the residue was poured into 100 mL of a 4M HCl. The mixture was extracted with 150 mL of ethyl acetate. The organic layer was isolated, dried over magnesium sulfate and the solvent was removed in vacuo. The residue was triturated in dichloromethane and the precipitate was filtered to give 3 g of the title compound as a solid.

$^1$H NMR (MeOD): 12.5 (s, 1H), 12.4 (s broad, 1H), 7.1 (s, 1H), 5.05 (q, 2H), 2.05 (t, 3H). LRMS (ES$^+$) m/z 252 [MH]$^+$ Preparation 176

4,6-dihydroxy-5-nitro-2-trifluoromethyl-nicotinic acid ethyl ester 4,6-dihydroxy-2-trifluoromethyl-nicotinic acid ethyl ester (1 g, 3.9 mmol) was dissolved in 10 mL of concentrated sulfuric acid and 2 mL of fuming nitric acid was added dropwise at room temperature. Once the addition was complete, the mixture was stirred at room temperature for 30 minutes. The mixture was then poured into crushed ice and the white precipitate was collected, dissolved in 50 mL of ethyl acetate, washed with 50 mL of water and 50 mL of brine, dried over magnesium sulfate and the solvent was removed in vacuo to give 1.1 g of the title compound as a white solid.

¹H NMR (d6 DMSO): 4.25 (q, 2H), 1.20 (t, 3H).

Preparation 177

6-trifluoromethyl-pyridine-2,4-diol 4,6-dihydroxy-2-trifluoromethyl-nicotinic acid ethyl ester (15 g, 59.7 mmol) was dissolved in 250 mL of concentrated HCl and the mixture was stirred at 115° C. for 3 days. The mixture was cooled down to 0° C. and 0.88 ammonia was added until pH~7. The solid formed was filtered, washed with water, azeotroped with toluene and dried in vacuo to give 9 g of the title compound as a white solid.

¹H NMR (d6 DMSO): 6.7 (s, 1H), 6.1 (s, 1H). LRMS (ES⁺) m/z 180 [MH]⁺

Preparation 178

(2-Amino-3-nitro-6-vinyl-pyridin-4-yl)-(6-methyl-pyridin-3-ylmethyl)-carbamic acid ethyl ester (2-Amino-6-chloro-3-nitro-pyridin-4-yl)-(6-methyl-pyridin-3-ylmethyl)-carbamic acid ethyl ester (715 mgs/1.955 mmols), potassium vinyltrifluoroborate (415 mgs/3.098 mmols), [1,1'-Bis(diphenylphosphino)ferrocene]dichloropalladium(II).CH$_2$Cl$_2$ (90 mgs/0.11 mmols) and triethylamine (0.28 mls/2.0 mmols) were combined in 'PrOH (8.0 mls) and heated at 50° C. under N$_2$ for 24 hrs. Preadsorbed directly onto silica and purified by column chromatography to give title compound (270 mgs) as a purple resin ¹H NMR (CD3OD, 400 MHz) ☐ 1.15-1.20 (mult, 3H), 2.50 (s, 3H), 4.05-4.15 (mult, 2H), 4.90-4.95 (mult, 2H), 5.60 (d, 1H), 6.20-6.30 (mult, 1H); 6.55-6.65 (mult, 2H), 7.20-7.25 (d/1H), 7.70 (mult/1H), 8.35 (s/1H); LRMS (ES) m/z 358 [MH]+.

Preparation 179

(2-Amino-6-formyl-3-nitro-pyridin-4-yl)-(6-methyl-pyridin-3-ylmethyl)-carbamic acid ethyl ester (2-Amino-3-nitro-6-vinyl-pyridin-4-yl)-(6-methyl-pyridin-3-ylmethyl)-carbamic acid ethyl ester (270 mgs/0.755 mmols) was dissolved in acetone (5 mls)/water (5 mls) and osmium tetroxide (2.5% wt in 'BuOH) (0.10 mls/0.008 mmols) was added. Stirred for 5 mins to give brown solution then added sodium metaperiodate (500 mgs/3.47 mmols). Orange suspension stirred for 1 hour. Partitioned between EtOAc (100 mls) and sodium thiosulfate pentahydrate (20% wt in H$_2$O) (50 mls). Organic collected, washed with brine, dried over Na$_2$SO$_4$, filtered and concentrated to a brown resin. Purification by column chromatography eluting with EtOAc gave the title compound (220 mgs) as a yellow oil.

¹H NMR (CDCl3, 400 MHz) ☐ 1.15-1.20 (mult, 3H), 2.55 (s, 3H), 4.10-4.20 (mult, 2H), 4.95 (s, 2H), 6.06-6.15 (br s, 2H), 7.05 (s, 1H); 7.10-7.15 (d, 1H), 7.60 (d/1H), 8.35-8.40 (s/1H); LRMS (AP) m/z 360 [MH]+.

Preparation 180

(2-Amino-3-nitro-6-oxazol-5-yl-pyridin-4-yl)-(6-methyl-pyridin-3-ylmethyl)-carbamic acid ethyl ester (2-Amino-6-formyl-3-nitro-pyridin-4-yl)-(6-methyl-pyridin-3-ylmethyl)-carbamic acid ethyl ester (190 mgs/0.529 mmols) was dissolved in MeOH (5 mls). Added (4-tolylsulphonyl)methylisocyanide (124 mgs/0.634 mmols) followed by anhydrous potassium carbonate (200 mgs/1.45 mmols). Stirred under N$_2$ for 1 hr then concentrated in vacuo. Partitioned between EtOAc (100 mls) and H$_2$O (50 mls). Organic collected, washed with brine, dried over Na$_2$SO$_4$, filtered and concentrated to a black resin. Purification by column chromatography eluting with 90:10 DCM/MeOH gave the title compound (135 mgs) as a crude brown solid.

LRMS (ES) m/z 399 [MH]+.

Biological Data

The ability of the compounds of formula (I) and their pharmaceutically acceptable salts, solvates and polymorphs to modulate TLR7 receptor activity is demonstrated by a PBL/HCV replicon bioassay as detailed below, in which the following abbreviations may be used:

EMCV: Encephalomyocarditis virus
IRES: Internal ribosmomal entry site
Huh: Huh-7 human hepatoma cell line 7 (parental cells used to generate HCV replicon cell lines)
luc: luciferase
ubi: ubiquitin
neo: neomycin
ET: glutamic acid, threonine (cell culture adaptive mutations in the replicon used in the assay)
RPMI-FCS: Roswell Park Memorial Institute (cell culture medium for PBL)—Foetal Calf Serum
PBL: peripheral blood lymphocytes PBL contain as a subpopulation plasmacytoid dendritic cells which are the natural interferon producing cells during an infection and as such are an excellent model in which to profile interferon inducers. As an extremly sensitive antiviral bioassay, supernatant taken from PBL is assayed for antiviral activity in the HCV replicon system. Antiviral EC50 values are defined as the concentration of a test compound applied to PBL that results in a 50% reduction of HCV replicon levels on transfer of a defined amount of PBL culture medium to a HCV replicon containing cell line. Although HCV replicon containing cells are fully responsive to PBL conditioned medium they do not respond directly to known TLR agonists such as Resiquimod and Imiquimod.

The HCV replicon (Huh-5-2[I389luc-ubi-neo-NS3-3'/ET]) is an in vitro model of HCV replication in which the luciferase reporter is incorporated into HCV sequences and stably maintained in the human hepatoma cell line Huh-7. The firefly luciferase reporter is expressed as a luciferase-ubiquitin-neomycin phosphotransferase fusion protein which is cleaved by host proteases to release luciferase. The replicon also contains an internal EMCV IRES, which drives translation of HCV NS3-5B polyprotein, which harbour cell culture adapted mutations to permit high cloning efficiency. The luciferase output has been shown to be directly proportional to the level of HCV RNA present in the host cell. Firefly luciferase activity is detected using a Bright-Glo™ Luciferase Assay System manufactured by Promega.

Typically, 1-3 mg of test compound is dissolved in 100% (v/v) DMSO to a final concentration of usually 1, 4 or 10 mM, or higher depending on the starting concentration required in the assay. An initial 3 fold serial dilution series of compounds in 100% DMSO is prepared from stocks. The dilution series is then further diluted 100 fold with complete RPMI-FCS. The final concentration of DMSO in the assay is thus 0.1% and that of the test compound is 1/1000 in the 100% DMSO dilution series. PBL are prepared seeded at 5×10⁵/well/90 μl into the previously prepared compound containing assay plates (96 well clear bottomed TC grade) and incubated for 24 h.

LucUbiNeo HCV replicon cells are seeded at 10⁴/well/90 μl. These are incubated for 24 h. After 24 h, 10 μl of medium is transferred from the PBL assay plates to the HCV replicon plates and incubated for a further 48 h.

| | Example No | | | | | | | | | | | |
|---|---|---|---|---|---|---|---|---|---|---|---|---|
| | 1 | 2 | 3 | 4 | 12 | 15 | 16 | 17 | 18 | 19 | 20 | 21 | 22 |
| $EC_{50}$ (nM) | 933 | 1540 | 266 | 497 | 240 | 252 | 104 | 955 | 107 | 355 | 700 | 215 | 450 |

| | Example No | | | | | | | | | | | |
|---|---|---|---|---|---|---|---|---|---|---|---|---|
| | 23 | 24 | 25 | 26 | 27 | 31 | 32 | 34 | 36 | 37 | 38 | 39 | 40 |
| $EC_{50}$ (nM) | 1080 | 1600 | 1000 | 926 | 453 | 3260 | 1710 | 1300 | 368 | 786 | 848 | 2200 | 427 |

| | Example No | | | | | | | | | | |
|---|---|---|---|---|---|---|---|---|---|---|---|
| | 49 | 50 | 54 | 55 | 56 | 60 | 61 | 70 | 78 | 82 | 83 | 86 |
| $EC_{50}$ (nM) | 2170 | 1970 | 302 | 2002 | 1300 | 445 | 1680 | 656 | 100 | 127 | 470 | 550 |

It is desirable that the compounds of the invention have selectivity for the TLR7 receptor over one or more other known Toll-like Receptors. It is also desirable that the compounds of the invention have selectivity for the TLR7 receptor over one or more cellular kinases and/or one or more purinergic receptors such as adenosine or phosphodiesterase receptors.

Examples 1, 2, 12 and 15 were tested and found to be selective for the TLR7 receptor over all other known Toll-like Receptors.

In addition, examples 1, 2, 12 and 15 were tested and found to be selective for the TLR7 receptor over the following targets: MEK (mitogen-activated protein kinase/extracellular signal-regulated kinase kinase), CDK1 (cyclin-dependent kinase-1), CDK2 (cyclin-dependent kinase-2) JNK (stress-activated protein kinase), MSK (mitogen and stress-activated protein kinase), MSK-1, SGK, AMPK, MLCK, CHK-2 and phosphodiesterase enzymes PDE3, PDE4 and PDE5.

In addition, examples 12 and 15 were tested and found to be selective for the TLR7 receptor over MAP (mitogen-activated protein kinase).

Furthermore, example 15 was tested and found to be selective for the TLR7 receptor over all known adenosine receptors A1, A2a, A2b and A3.

We claim:

1. A compound of formula (I)

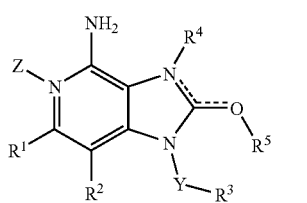

(I)

or a tautomer thereof, wherein:
(a) Y is a direct bond, and $R^3$ is selected from aryl, and —$(C_1$-$C_4)$alkylene-O—$(C_1$-$C_4)$alkyl; or
(b) Y is $(C_1$-$C_4)$alkylene, and $R^3$ is selected from aryl, $(C_3$-$C_7)$cycloalkyl and a 3 to 10-membered heterocyclyl;
Z is an oxygen or absent;
$R^1$ is selected from H, halo, OH, CN, $(C_1$-$C_6)$alkyl, $(C_3$-$C_7)$cycloalkyl, $(C_1$-$C_6)$alkoxy, —$NHSO_2R^6$, —$NR^6R^7$, —$C(O)R^6$, —$CO_2R^6$, —$C(O)NR^6R^7$, —$C(O)NR^6SO_2R^8$, aryl and 3 to 10-membered heterocyclyl;
$R^2$ is selected from H, halo, OH, $(C_1$-$C_6)$alkyl, $(C_3$-$C_7)$cycloalkyl, $(C_1$-$C_6)$alkoxy, —$NR^6R^7$, —$CO_2R^6$, —$C(O)NR^6R^7$, —$C(O)NR^6SO_2R^8$, and 3 to 10-membered heterocyclyl; or
$R^1$ and $R^2$ may be joined to form a $(C_2$-$C_5)$alkylene link, said link optionally incorporating 1 or 2 heteroatoms each independently selected from N, O and S;
$R^5$ is absent and $R^4$ is selected from H, $(C_3$-$C_7)$cycloalkyl, aryl, —$(CH_2)$aryl, —$C(O)R^9$, —$CO_2R^9$, —$(C_1$-$C_6)$alkylene-O—$C(O)R^9$, —$(C_1$-$C_6)$alkylene-O—$CO_2R^9$), —$C(O)NR^9R^{10}$, —$(C_1$-$C_6)$alkylene-O—$C(O)NR^9R^{10}$ and —$(C_1$-$C_6)$alkylene-O—$P(O)(OH)_2$; or
$R^4$ is absent and $R^5$ is selected from $R^9$, —$C(O)R^9$, —$CO_2R^9$, —$(C_1$-$C_6)$alkylene-O—$C(O)R^9$, —$(C_1$-$C_6)$alkylene-O—$CO_2R^9$, —$C(O)NR^9R^{10}$, —$(C_1$-$C_6)$alkylene-O—$C(O)NR^9R^{10}$ and —$(C_1$-$C_6)$alkylene-O—$P(O)(OH)_2$;
$R^6$ and $R^7$ are each independently selected from H, $(C_1$-$C_6)$alkyl, $(C_3$-$C_7)$cycloalkyl, and —$(C_1$-$C_6)$alkylene$(C_3$-$C_7)$cycloalkyl; or $R^6$ and $R^7$ taken together with the nitrogen to which they are attached form a 3 to 6 membered saturated heterocycle optionally containing a further one or two heteroatoms selected from N, O and S;
$R^8$ is selected from $(C_1$-$C_6)$alkyl, $(C_3$-$C_7)$cycloalkyl and phenyl;
$R^9$ and $R^{10}$ are each independently selected from H, $(C_1$-$C_6)$alkyl, $(C_3$-$C_7)$cycloalkyl, aryl, —$(CH_2)$aryl and 3 to 10-membered heterocyclyl; or $R^9$ and $R^{10}$, taken together with the nitrogen to which they are attached, form a 3 to 10-membered heterocyclyl group; and
$R^{11}$ and $R^{12}$ are independently selected from H and $(C_1$-$C_6)$alkyl; or $R^{11}$ and $R^{12}$ together with the N to which they are attached form a 3 to 6 membered saturated heterocyclyl optionally containing a further one or two heteroatoms selected from N, O and S;
wherein said alkyl, cycloalkyl, alkoxy, aryl and heterocyclyl groups being optionally substituted by one or more atoms or groups independently selected from halo, OH, oxo, $CF_3$, CN, $(C_1$-$C_6)$alkyl, $(C_3$-$C_7)$cycloalkyl, $(C_1$-$C_6)$alkoxy, —$(C_1$-$C_6)$alkylene-O—$(C_1$-$C_6)$alkyl, —$(C_1$-$C_6)$alkylene-OH, —$NR^{11}R^{12}$, —$(C_1$-$C_6)$alkylene-$NR^{11}R^{12}$, aryl and 3 to 10-membered heterocyclyl; or
a pharmaceutically acceptable salt thereof.

2. A compound according to claim 1 wherein $R^1$ is selected from:
(a) H;
(b) CN;
(c) halo
(d) $(C_1-C_6)$alkyl optionally substituted by one to three halo atoms;
(e) tetrahydrofuranoxy;
(f) $(C_1-C_6)$alkyl substituted by a 3 to 6 membered saturated heterocyclyl containing 1 to 3 hetero atoms independently selected from N, O and S wherein said heterocyclyl is optionally substituted by one to three groups independently selected from $CF_3$, $(C_1-C_6)$alkyl, $(C_1-C_6)$alkoxy and $-(C_1-C_6)$alkylene-O-$(C_1-C_6)$alkyl;
(g) $-(C_1-C_4)$alkylene-O-$(C_1-C_6)$alkyl;
(h) $-(C_1-C_4)$alkylene-N(H)-$(C_1-C_4)$alkylene-O-$(C_1-C_4)$alkyl;
(i) $(C_1-C_6)$alkoxy optionally substituted by OH or cyclopropyl;
(j) $(C_3-C_7)$cycloalkyl;
(k) $-(C_1-C_4)$alkylene$(C_3-C_7)$cycloalkyl;
(l) $-C(O)NR^6R^7$;
(m) $-CO_2R^6$;
(n) $-C(O)R^6$;
(o) a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; or a 6-membered aromatic heterocyclyl comprising 1 to 3 nitrogen atoms, said 5 and 6 membered aromatic heterocyclyl being optionally substituted by one to three atoms or groups independently selected from halo, OH, $CF_3$, $(C_1-C_6)$alkyl, $(C_1-C_6)$alkoxy, $-(C_1-C_6)$alkylene-O-$(C_1-C_6)$alkyl, $-(C_1-C_6)$alkylene-OH, $-NR^{11}R^{12}$ and $-(C_1-C_6)$alkylene-$NR^{11}R^{12}$;
(p) phenyl optionally substituted by 1 to 3 halo atoms;
(q) $-NR^6R^7$; and
(r) $-NH-(C_1-C_4)$alkylene-O-$(C_1-C_6)$alkyl; or a pharmaceutically acceptable salt thereof, wherein $R^6$, $R^7$, $R^{11}$ and $R^{12}$ are as defined in claim 1.

3. A compound according to claim 1, wherein $R^1$ is selected from methyl or ethyl substituted by one to three fluoro atoms; cyclopropyl; $-(C_1-C_2)$alkylene-O-$(C_1-C_2)$alkyl; $(C_1-C_4)$alkoxy optionally substituted by OH or cyclopropyl; $-COCH_3$; $-CH_2OCH_3$; and $-CO_2CH_3$; or a pharmaceutically acceptable salt thereof.

4. A compound according to claim 1, wherein $R^1$ is cyclopropyl or $CF_3$, or a pharmaceutically acceptable salt thereof.

5. A compound according to claim 1, wherein $R^1$ is a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom, said 5 membered aromatic heterocyclyl being optionally substituted by one to three atoms or groups independently selected from halo, OH, $CF_3$, $(C_1-C_6)$alkyl, $(C_1-C_6)$alkoxy, $-(C_1-C_3)$alkylene-O-$(C_1-C_4)$alkyl, $-(C_1-C_4)$alkylene-OH, $-NR^{11}R^{12}$ and $-(C_1-C_3)$alkylene-$NR^{11}R^{12}$, or a pharmaceutically acceptable salt thereof, wherein $R^{11}$ and $R^{12}$ are as defined in claim 1.

6. A compound according to claim 5, wherein $R^1$ is selected from imadazolyl, oxazolyl, oxadiazolyl, triazole, pyrazole and thiazole, all of which are optionally substituted by by one to three atoms or groups independently selected from halo, OH, $CF_3$, $(C_1-C_6)$alkyl, $(C_1-C_6)$alkoxy, $-(C_1-C_3)$alkylene-O-$(C_1-C_4)$alkyl, $-(C_1-C_4)$alkylene-OH and $-(C_1-C_3)$alkylene-$NR^{11}R^{12}$, or a pharmaceutically acceptable salt thereof.

7. A compound according to claim 6, wherein $R^1$ is selected from unsubstituted oxazolyl, triazole, pyrazole and thiazole, or a pharmaceutically acceptable salt thereof.

8. A compound according to claim 1, wherein $R^2$ is selected from:
(a) H;
(b) halo;
(c) $(C_1-C_6)$alkyl optionally substituted by one to three halo atoms;
(d) tetrahydrofuranoxy;
(e) $(C_1-C_6)$alkyl substituted by a 3 to 6 membered saturated heterocyclyl containing 1 to 3 hetero atoms independently selected from N, O and S wherein said heterocyclyl is optionally substituted by one to three groups independently selected from $CF_3$, $(C_1-C_6)$alkyl, $(C_1-C_6)$alkoxy and $-(C_1-C_6)$alkylene-O-$(C_1-C_6)$alkyl;
(f) $-(C_1-C_4)$alkylene-O-$(C_1-C_6)$alkyl;
(g) $-(C_1-C_4)$alkylene-N(H)-$(C_1-C_4)$alkylene-O-$(C_1-C_4)$alkyl;
(h) $(C_1-C_6)$alkoxy optionally substituted by OH or cyclopropyl;
(i) $(C_3-C_7)$cycloalkyl;
(j) $-(C_1-C_4)$alkylene$(C_3-C_7)$cycloalkyl;
(k) $-C(O)NR^6R^7$;
(l) $-CO_2R^6$;
(m) $-C(O)R^6$;
(n) a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; or a 6-membered aromatic heterocyclyl comprising 1 to 3 nitrogen atoms, said 5 and 6 membered aromatic heterocyclyl being optionally substituted by one to three atoms or groups independently selected from halo, OH, $CF_3$, $(C_1-C_6)$alkyl, $(C_1-C_6)$alkoxy, $-(C_1-C_6)$alkylene-O-$(C_1-C_6)$alkyl, $-(C_1-C_6)$alkylene-OH, $-NR^{11}R^{12}$ and $-(C_1-C_6)$alkylene-$NR^{11}R^{12}$;
(o) phenyl optionally substituted by 1 to 3 halo atoms;
(p) $-NR^6R^7$; and
(q) $-NH-(C_1-C_4)$alkylene-O-$(C_1-C_6)$alkyl; or a pharmaceutically acceptable salt thereof, wherein $R^6$, $R^7$, $R^{11}$ and $R^{12}$ are as defined in claim 1.

9. A compound according to claim 1, wherein $R^2$ is H or methyl, or a pharmaceutically acceptable salt thereof.

10. A compound according to claim 1, wherein $R^2$ is H, or a pharmaceutically acceptable salt thereof.

11. A compound according to claim 1, wherein Y is methylene; and $R^3$ is selected from aryl; a 5 membered aromatic heterocyclyl comprising (i) 1 to 4 nitrogen atoms, or (ii) 1 to 2 nitrogen atoms and 1 oxygen or sulphur atom, or (iii) 1 oxygen or sulphur atom; and a 6-membered aromatic heterocyclyl comprising 1 to 3 nitrogen atoms; said aryl and aromatic heterocycle being optionally substituted by one to three atoms or groups independently selected from halo, OH, oxo, $CF_3$, CN, $(C_1-C_6)$alkyl, $(C_3-C_7)$cycloalkyl, $(C_1-C_6)$alkoxy, $-(C_1-C_6)$alkylene-O-$(C_1-C_6)$alkyl, $-(C_1-C_6)$alkylene-OH, $-NR^{11}R^{12}$, $-(C_1-C_6)$alkylene-$NR^{11}R^{12}$, aryl and 3 to 10-membered heterocyclyl, or a pharmaceutically acceptable salt thereof, wherein $R^{11}$ and $R^{12}$ are as defined in claim 1.

12. A compound according to claim 1, wherein Y is methylene; and $R^3$ is selected from phenyl, pyridyl, pyrimidyl, pyridizinyl and pyrazinyl, each of which are optionally substituted by one to three atoms or groups independently selected from halo, $(C_{1-4})$alkyl, $(C_1-C_4)$alkoxy and $CF_3$, or a pharmaceutically acceptable salt thereof.

13. A compound according to claim 1, wherein Y is methylene; and $R^3$ is selected from phenyl, pyridin-3-yl and 6-methyl-pyridin-3-yl, or a pharmaceutically acceptable salt thereof.

14. A compound according to claim 1, wherein $R^5$ is absent; and
$R^4$ is selected from —$(C_1$-$C_6)$alkylene-O—C(O)$R^9$, —$(C_1$-$C_6)$alkylene-O—CO$_2R^9$, —$(C_1$-$C_6)$alkylene-O—C(O)NR$^9R^{10}$ and —$(C_1$-$C_6)$alkylene-O—P(O)(OH)$_2$, or a pharmaceutically acceptable salt thereof, wherein $R^9$ and $R^{10}$ are as defined in claim 1.

15. A compound according to claim 1, wherein $R^4$ is H and $R^5$ is absent, or a pharmaceutically acceptable salt thereof.

16. A compound according to claim 1, wherein $R^4$ is absent; and
$R^5$ is selected from —$(C_1$-$C_6)$alkylene-O—C(O)$R^9$, —$(C_1$-$C_6)$alkylene-O—CO$_2R^9$), —$(C_1$-$C_6)$alkylene-O—C(O)NR$^9R^{10}$ and —$(C_1$-$C_6)$alkylene-O—P(O)(OH)$_2$, or a pharmaceutically acceptable salt thereof, wherein $R^9$ and $R^{10}$ are as defined in claim 1.

17. A compound according to claim 1 wherein:
Y is methylene;
$R^1$ is selected from CF$_3$, cyclopropyl, and oxazole;
$R^2$ is H;
$R^3$ is selected from phenyl, pyridin-3-yl and 6-methyl-pyridin-3-yl.
$R^4$ is H; and
$R^5$ is absent; or
or a pharmaceutically acceptable salt thereof.

18. A compound of formula (Ic)

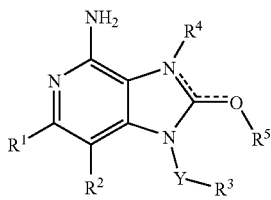

(Ic)

or a tautomer thereof, wherein:
Y is a methylene;
$R^1$ and $R^2$ are each independently selected from H, halo, OH, $(C_1$-$C_6)$alkyl, $(C_3$-$C_7)$cycloalkyl, $(C_1$-$C_6)$alkoxy, —NR$^6R^7$, —CO$_2R^6$, —C(O)NR$^6R^7$, —C(O)NR$^6$SO$_2R^8$, aryl and 3 to 10-membered heterocyclyl; or
$R^1$ and R may be joined to form a $(C_2$-$C_5)$alkylene link, said link optionally incorporating 1 or 2 heteroatoms each independently selected from N, O and S;
$R^3$ is selected from $(C_1$-$C_6)$alkyl, $(C_3$-$C_7)$cycloalkyl, aryl and 3 to 10-membered heterocyclyl;
$R^4$ is selected from $R^9$, —C(O)$R^9$, —CO$_2R^9$ and —C(O)NR$^9R^{10}$, and $R^5$ is absent; or
$R^5$ is selected from $R^9$, —C(O)$R^9$, —CO$_2R^9$ and —C(O)NR$^9R^{10}$, and $R^4$ is absent;
$R^6$ and $R^7$ are each independently selected from H and $(C_1$-$C_6)$alkyl;
$R^8$ is selected from $(C_1$-$C_6)$alkyl, $(C_3$-$C_7)$cycloalkyl and phenyl; and
$R^9$ and $R^{10}$ are each independently selected from H, $(C_1$-$C_6)$alkyl, $(C_3$-$C_7)$cycloalkyl, aryl, —(CH$_2$)aryl and 3 to 10-membered heterocyclyl; or
$R^9$ and $R^{10}$, taken together with the nitrogen to which they are attached, form a 3 to 10-membered heterocyclyl group;

wherein said alkyl, cycloalkyl, alkoxy, aryl and heterocyclyl groups being optionally substitued by one or more groups independently selected from halo, OH, oxo, CF$_3$, CN, $(C_1$-$C_6)$alkyl, $(C_3$-$C_7)$cycloalkyl, $(C_1$-$C_6)$alkoxy, —$(C_1$-$C_6)$alkylene-O—$(C_1$-$C_6)$alkyl, —NH$(C_1$-$C_6)$alkyl, —N$((C_1$-$C_6)$alkyl$)_2$, aryl and 3 to 10-membered heterocyclyl; or
or a pharmaceutically acceptable salt thereof,
with the proviso that when $R^1$ and $R^2$ are H; Z and R5 are absent, then
(a) $R^4$ is not methyl when Y—$R^3$ is ethyl; and
(b) $R^4$ is not H or methyl when Y—$R^3$ is methyl.

19. A compound according to claim 1, selected from:
4-Amino-1-benzyl-6-cyclopropyl-1,3-dihydro-imidazo [4,5-c]pyridin-2-one;
4-Amino-1-benzyl-6-oxazol-2-yl-1,3-dihydro-imidazo[4,5-c]pyridin-2-one; and
4-Amino-1-benzyl-6-trifluoromethyl-1,3-dihydro-imidazo[4,5-c]pyridine-2-one ; or
a pharmaceutically acceptable salt thereof.

20. A pharmaceutical composition, comprising a compound of the formula

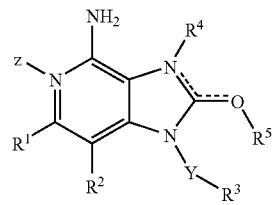

or a tautomer thereof, wherein:
(a) Y is a direct bond, and $R^3$ is selected from aryl, $(C_1$-$C_6)$alkyl and —$(C_1$-$C_4)$alkylene-O—$(C_1$-$C_4$alkyl; or
(b) Y is $(C_1$-$C_4)$alkylene, and $R^3$ is selected from aryl, $(C_3$-$C_7)$cycloalkyl and a 3 to 10-membered heterocyclyl;
Z is an oxygen or is absent;
$R^1$ is selected from H, halo, OH, CN, $(C_1$-$C_6)$alkyl, $(C_3$-$C_7)$cycloalkyl, $(C_1$-$C_6)$alkoxy, —NHSO$_2R^6$, —NR$^6R^7$, —C(O)$R^6$, —CO$_2R^6$, —C(O)NR$^6R^7$, —C(O)NR$^6$SO$_2R^8$, aryl and 3 to 10-membered heterocyclyl;
$R^2$ is selected from H, halo, OH, $(C_1$-$C_6)$alkyl, $(C_3$-$C_7)$cycloalkyl, $(C_1$-$C_6)$alkoxy, —NR$^6R^7$, —CO$_2R^6$, —C(O)NR$^6R^7$, —C(O)NR$^6$SO$_2R^6$, and 3 to 10-membered heterocyclyl; or
$R^1$ and $R^2$ may be joined to form a $(C_2$-$C_5)$alkylene link, said link optionally incorporating 1 or 2 heteroatoms each independently selected from N, O and S;
$R^5$ is absent and $R^4$ is selected from H, $(C_3$-$C_7)$cycloalkyl, aryl, —(CH$_2$)aryl, —C(O)$R^9$, —CO$_2R^9$, —$(C_1$-$C_6)$ alkylene-O—C(O) $R^9$, —$(C_1$-$C_6)$alkylene-O—CO$_2R^9$), —C(O)NR$^9R^{10}$, —$(C_1$-$C_6)$alkylene-O—C(O)NR$^9R^{10}$ and —$(C_1$-$C_6)$alkylene-O—P(O)(OH)$_2$; or
$R^4$ absent and $R^5$ is selected from $R^9$, —C(O)$R^9$, —CO$_2R^9$, —$(C_1$-$C_6)$alkylene-O—C(O)$R^9$, —$(C_1$-$C_6)$alkylene-O—CO$_2R^9$, —C(O)NR$^9R^{10}$, —$(C_1$-$C_6)$alkylene-O—C(O)NR$^9R^{10}$ and —$(C_1$-$C_6)$alkylene-O—P(O)(OH)$_2$;
$R^6$ and $R^7$ are each independently selected from H, $(C_1$-$C_6)$ alkyl, $(C_3$-$C_7)$cycloalkyl, and —$(C_1$-$C_6)$alkylene$(C_3$-$C_7)$cycloalkyl; or $R^6$ and $R^7$ taken together with the nitrogen to which they are attached form a 3 to 6 membered saturated heterocycle optionally containing a further one or two heteroatoms selected from N, O and S;

$R^8$ is selected from $(C_1-C_6)$, $(C_3-C_7)$cycloalkyl and phenyl;

$R^9$ and $R^{10}$ are each independently selected from H, $(C_1-C_6)$alkyl, $(C_3-C_7)$cycloalkyl, aryl, —$(CH_2)$aryl and 3 to 10-membered heterocyclyl; or $R^9$ and $R^{10}$, taken together with the nitrogen to which they are attached, form a 3 to 10-membered heterocyclyl group; and $R^{11}$ and $R^{12}$ are independently selected from H and $(C_1-C_6)$alkyl; or $R^{11}$ and $R^{12}$ together with the N to which they are attached form a 3 to 6 membered saturated heterocyclyl optionally containing a further one or two heteroatoms selected from N, O and S;

wherein said alkyl, cycloalkyl, alkoxy, aryl and heterocyclyl groups being optionally substituted by one or more atoms or groups independently selected from halo, OH, oxo, $CF_3$, CN, $(C_1-C_6)$alkyl, $(C_3-C_7)$cycloalkyl, $(C_1-C_6)$alkoxy, —$(C_1-C_6)$alkylene-O—$(C_1-C_6)$alkyl, —$(C_1-C_6)$alkylene-OH, —$NR^{11}R^{12}$, —$(C_1-C_6)$alkylene-$NR^{11}R^{12}$, aryl and 3 to 10-membered heterocyclyl; or a pharmaceutically acceptable salt thereof, and one or more pharmaceutically acceptable excipients, with the proviso that when $R^1$ and $R^2$ are H, and Z and $R^5$ are absent, then (a) $R^4$ is not methyl when Y—$R^3$ is ethyl; and (b) $R^4$ is not H or methyl when Y—$R^3$ is methyl.

21. A pharmaceutical composition according to claim 20, further comprising one or more additional therapeutic agents.

22. A pharmaceutical composition according to claim 21, wherein said additional therapeutic agent is selected from inhibitors of HCV NS3A protein, HCV NS5A protein, HCV NS4B protein, HCV polymerase, HCV metalloprotease, HCV serine protease, HCV helicase and p7 protein.

* * * * *